(12) United States Patent
Breinlinger et al.

(10) Patent No.: US 9,879,016 B2
(45) Date of Patent: Jan. 30, 2018

(54) INDAZOLONES AS MODULATORS OF TNF SIGNALING

(71) Applicant: AbbVie Inc., North Chicago, IL (US)

(72) Inventors: Eric Breinlinger, Charlton, MA (US); Andrew Burchat, Shrewsbury, MA (US); Justin Dietrich, Lindenhurst, IL (US); Michael Friedman, Brookline, MA (US); David Ihle, Worcester, MA (US); David Kinsman, Ashland, MA (US); Kelly Mullen, Charlton, MA (US); Augustine Osuma, Lindenhurst, IL (US); Anil Vasudevan, Union Grove, WI (US); Noel Wilson, Kenosha, WI (US)

(73) Assignee: AbbVie Inc., North Chicago, IL (US)

(*) Notice: Subject to any disclaimer, the term of this patent is extended or adjusted under 35 U.S.C. 154(b) by 0 days.

(21) Appl. No.: 15/130,323

(22) Filed: Apr. 15, 2016

(65) Prior Publication Data
US 2016/0304526 A1  Oct. 20, 2016

Related U.S. Application Data

(60) Provisional application No. 62/149,336, filed on Apr. 17, 2015.

(51) Int. Cl.
*C07D 487/04* (2006.01)
*C07D 498/04* (2006.01)
*C07D 519/00* (2006.01)

(52) U.S. Cl.
CPC ......... *C07D 487/04* (2013.01); *C07D 498/04* (2013.01); *C07D 519/00* (2013.01)

(58) Field of Classification Search
CPC ... C07D 487/04; C07D 498/04; C07D 519/00
USPC ...................................... 514/228.2
See application file for complete search history.

(56) References Cited

U.S. PATENT DOCUMENTS

| | | |
|---|---|---|
| 2007/0021337 A1 | 1/2007 | Lee et al. |
| 2007/0213337 A1 | 9/2007 | Zhao et al. |
| 2008/0287448 A1 | 11/2008 | Zoller et al. |
| 2010/0029616 A1 | 2/2010 | Kinney et al. |
| 2010/0204214 A1 | 8/2010 | Chytil et al. |
| 2014/0235675 A1 | 8/2014 | Papeo et al. |
| 2016/0039811 A1 | 2/2016 | Yoshida et al. |

FOREIGN PATENT DOCUMENTS

| | | | |
|---|---|---|---|
| BE | WO 2015086527 A1 * | 6/2015 | ........... C07D 471/04 |
| JP | 2009035531 A | 2/2009 | |
| WO | WO-2004/063163 A1 | 7/2004 | |
| WO | WO-2004/093872 A1 | 11/2004 | |
| WO | WO-2005/100353 A1 | 10/2005 | |
| WO | 2005121096 | 12/2005 | |
| WO | WO-2006/047516 | 5/2006 | |
| WO | 2006108948 | 10/2006 | |
| WO | 2007042178 | 4/2007 | |
| WO | WO-2007/110216 A1 | 10/2007 | |
| WO | 2007126122 | 11/2007 | |
| WO | 2007126128 | 11/2007 | |
| WO | WO-2008/008432 A2 | 1/2008 | |
| WO | 2008051403 | 5/2008 | |
| WO | 2008051493 | 5/2008 | |
| WO | 2008141385 | 11/2008 | |
| WO | WO-2010/054278 A2 | 5/2010 | |
| WO | 2010084402 | 7/2010 | |
| WO | 2010115491 | 10/2010 | |
| WO | WO-2011/062864 A2 | 5/2011 | |
| WO | 2011119565 | 9/2011 | |
| WO | WO-2011/116356 A2 | 9/2011 | |
| WO | 2012072019 | 6/2012 | |
| WO | 2012088124 | 6/2012 | |
| WO | 2013000994 | 1/2013 | |
| WO | WO-2013/186229 A1 | 12/2013 | |
| WO | 2014009295 | 1/2014 | |
| WO | WO-2014/009296 A1 | 1/2014 | |
| WO | WO-2014/157569 A1 | 10/2014 | |

(Continued)

OTHER PUBLICATIONS

Database CAPLUS in STN, Acc. No. 2009:1290752, Vidal'-Khuan et al., RU 2370496 C2 (Oct. 20, 2009) (abstract).
Database CAPLUS in STN, Acc. No. 2008:276955, Cappelli et al., Journal of Medicinal Chemistry (2008),51(7), pp. 2137-2146 (abstract).
Database CAPLUS in STN, Acc. No. 2005:1154552, Vidal et al., WO 2005/100353 A 1 (Oct. 27, 2005) (abstract).
Chimirri et al, "Synethsis der Pharmazie, and Antitumour Activity of 1 H,3H-thiazolo[3,4-a]benzimidazole Derivatives", Archiv der Pharmazie, vol. 334, No. 6, Jun. 1, 2001, pp. 203-208.
U.S. Appl. No. 15/130279, filed Apr. 15, 2016.
U.S. Appl. No. 15/130362, filed Apr. 15, 2016.
Kumar K.S., et al., "A New Three-Component Reaction: Green Synthesis of Novel Soindolo[2,1-a]quinazoline Derivatives as Potent Inhibitors of TNF-α," Chemical Communications, 2011, vol. 47 (17), pp. 5010-5012.

(Continued)

*Primary Examiner* — Yong Chu
(74) *Attorney, Agent, or Firm* — Dana M. Gordon; Foley Hoag LLP

(57) ABSTRACT

The disclosure provides compounds of Formula (I)

Formula (I)

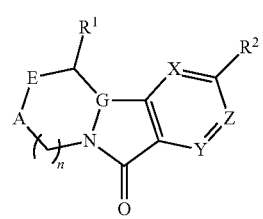

pharmaceutically acceptable salts, pro-drugs, biologically active metabolites, stereoisomers and isomers thereof wherein the variable are defined herein. The compounds of the disclosure are useful for treating immunological and oncological conditions.

26 Claims, No Drawings

(56) References Cited

FOREIGN PATENT DOCUMENTS

| WO | 2015086525 | 6/2015 |
|---|---|---|
| WO | 20015086526 | 6/2015 |
| WO | 20015086527 | 6/2015 |
| WO | WO-2015/086496 A1 | 6/2015 |
| WO | WO-2015/086498 A1 | 6/2015 |
| WO | WO-2015/086499 A1 | 6/2015 |
| WO | WO-2015/086500 A1 | 6/2015 |
| WO | WO-2015/086501 A1 | 6/2015 |
| WO | WO-2015/086502 A1 | 6/2015 |
| WO | WO-2015/086503 A1 | 6/2015 |
| WO | WO-2015/086504 A1 | 6/2015 |
| WO | WO-2015/086505 A1 | 6/2015 |
| WO | WO-2015/086506 A1 | 6/2015 |
| WO | WO-2015/086507 A1 | 6/2015 |
| WO | WO-2015/086508 A1 | 6/2015 |
| WO | WO-2015/086509 A1 | 6/2015 |
| WO | WO-2015/086511 A1 | 6/2015 |
| WO | WO-2015/086512 A1 | 6/2015 |
| WO | WO-2015/086513 A1 | 6/2015 |
| WO | WO-2015/086519 A1 | 6/2015 |
| WO | WO-2015/086520 A1 | 6/2015 |
| WO | WO-2015/086521 A1 | 6/2015 |
| WO | WO-2015/086523 A1 | 6/2015 |
| WO | WO-2016/050975 A1 | 4/2016 |
| WO | WO-2016/149436 A1 | 9/2016 |
| WO | WO-2016/149437 A1 | 9/2016 |
| WO | WO-2016/149439 A1 | 9/2016 |
| WO | WO-2016/168633 A1 | 10/2016 |
| WO | WO-2016/168638 A1 | 10/2016 |
| WO | WO-2016/168641 A1 | 10/2016 |
| WO | WO-2016/198398 A1 | 12/2016 |
| WO | WO-2016/198400 A1 | 12/2016 |
| WO | WO-2016/198401 A1 | 12/2016 |
| WO | WO-2016/202411 A1 | 12/2016 |
| WO | WO-2016/202412 A1 | 12/2016 |
| WO | WO-2016/202413 A1 | 12/2016 |
| WO | WO-2016/202414 A1 | 12/2016 |
| WO | WO-2016/202415 A1 | 12/2016 |
| WO | WO-2017/023902 A1 | 2/2017 |
| WO | WO-2017/023905 A1 | 2/2017 |

OTHER PUBLICATIONS

Cappelli et al., "Design, Synthesis, and Biological Evaluation of AT1 Angiotensin II Receptor antagonists Based on the Pyrazolo[3,4-b]pyridine and Related Heteroaromatic Bicyclic Systems," J Med Chem, 51: 2137-2146 (2008).

International Search Report and Written Opinion for International Application No. PCT/2016/027799 dated [May 25, 2016].

International Search Report and Written Opinion for International Application No. PCT/2016/027808 dated [Jun. 1, 2016].

International Search Report and Written Opinion for International Application No. PCT/2016/027814 dated [Jun. 10, 2016].

* cited by examiner

INDAZOLONES AS MODULATORS OF TNF SIGNALING

PRIORITY CLAIM

This application claims the benefit of U.S. Provisional Application No. 62/149,336, filed Apr. 17, 2015, which is hereby incorporated by reference in its entirety.

FIELD OF THE DISCLOSURE

The present disclosure relates to a class of fused indazolone derivatives, and to their use in therapy. More particularly, this disclosure is concerned with pharmacologically active substituted indazolone derivatives. These compounds are modulators of the signaling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

BACKGROUND

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certulizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, Drug Discovery Today, 2009, 14, 1082-1088; and F. S. Carneiro et al., J. Sexual Medicine, 2010, 7, 3823-3834). The compounds in accordance with the present disclosure, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present disclosure may be beneficial as pharmacological standards for use in the development of new biological tests and in the search for new pharmacological agents. Thus, in one embodiment, the compounds of this disclosure may be useful as radioligands in assays for detecting pharmacologically active compounds. In an alternative embodiment, certain compounds of this disclosure may be useful for coupling to a fluorophore to provide fluorescent conjugates that can be utilized in assays (e.g. a fluorescence polarization assay) for detecting pharmacologically active compounds.

SUMMARY OF THE DISCLOSURE

The compounds in accordance with the present disclosure, being potent modulators of human TNFα activity, may be beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present disclosure may be beneficial as pharmacological standards for use in the development of new biological tests and in the search for new pharmacological agents. Thus, in one embodiment, the compounds of this disclosure may be useful as radioligands in assays for detecting pharmacologically active compounds. In an alternative embodiment, certain compounds of this disclosure may be useful for coupling to a fluorophore to provide fluorescent conjugates that can be utilized in assays (e.g., a fluorescence polarization assay) for detecting pharmacologically active compounds.

The compounds in accordance with the present disclosure potently neutralize the activity of TNFα using the TNFα fluorescence polarization competitive binding assay. When tested in this assay, the compounds of the present disclosure exhibit an IC50 value of 50 μM or less, generally of 10 μM or less, usually of 5 μM or less, typically of 1 μM or less, suitably of 500 nM or less, ideally of 100 nM or less, and preferably of 20 nM or less (the skilled person will appreciate that a lower IC50 figure denotes a more active compound).

In a first embodiment, the disclosure provides a compound of Formula (I)

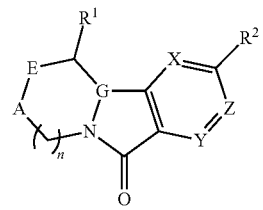

Formula (I)

or a pharmaceutically acceptable salt, prodrug or stereoisomer thereof, wherein:

X, Y and Z are independently $CR^4$ or N;
provided that Y and Z are not both N;
A is $-C(R^z)_2-$;
E is $CH_2$ or O and G is CH; or
E is $CH_2$ and G is CH or N;
$R^1$ is optionally substituted aryl or optionally substituted heteroaryl;
$R^2$ is $-R^{2a}-R^{2b}$, wherein:
$R^{2a}$ is an optionally substituted saturated, unsaturated or partially saturated heterocyclyl or optionally substituted heteroaryl;

$R^{2b}$ is —N($R^a$)($R^b$), —O($R^a$), optionally substituted ($C_1$-$C_5$)alkyl, optionally substituted ($C_3$-$C_6$)cycloalkyl, —(CH$_2$)$_p$-optionally substituted heteroaryl or —(CH$_2$)$_p$-optionally substituted heterocyclyl; wherein $R^a$ and $R^b$ are independently selected from H, optionally substituted ($C_1$-$C_5$)alkyl, and —(CH$_2$)$_n$-optionally substituted heterocyclyl;

$R^4$ is independently H, halo, CF$_3$, or ($C_1$-$C_3$)alkyl;

$R^z$ is independently H, halo, CF$_3$, or ($C_1$-$C_3$)alkyl;

n is 0 or 1; and p is 0 or 1.

In a second embodiment, the disclosure provides a compound according to the first embodiment wherein $R^{2b}$ is —N($R^a$)($R^b$), —O($R^a$), optionally substituted ($C_1$-$C_5$)alkyl, optionally substituted ($C_3$-$C_6$)cycloalkyl, or —(CH$_2$)$_p$-optionally substituted heterocyclyl; wherein $R^a$ and $R^b$ are independently selected from H, optionally substituted ($C_1$-$C_5$)alkyl, and —(CH$_2$)$_n$-optionally substituted heterocyclyl.

In a third embodiment, the disclosure provides a compound according to any of the foregoing embodiments wherein E is CH$_2$.

In a fourth embodiment, the disclosure provides a compound according to any of the foregoing embodiments wherein X is CH, Y is CH and Z is CR$^4$.

In a fifth embodiment, the disclosure provides a compound according to any of the foregoing embodiments wherein $R^4$ is F.

In a sixth embodiment, the disclosure provides a compound according to any of the foregoing embodiments wherein X is CH, Y is CH and Z is CH.

In a seventh embodiment, the disclosure provides a compound according to any of the foregoing embodiments wherein G is N.

In an eighth embodiment, the disclosure provides a compound according to any of the foregoing embodiments wherein $R^1$ is optionally substituted phenyl, optionally substituted pyrazolyl, optionally substituted pyridyl, optionally substituted pyrimidinyl or optionally substituted thiazolyl.

In a ninth embodiment, the disclosure provides a compound according any of the foregoing embodiments wherein $R^1$ is optionally substituted phenyl.

In a tenth embodiment, the disclosure provides a compound according to any of the foregoing embodiments wherein $R^1$ is optionally substituted by one or more substituents independently selected from —CF$_3$, —CN, —C(O)NH$_2$, —OCHF$_2$, —OCH$_3$, or ($C_1$-$C_3$)alkyl.

In an eleventh embodiment, the disclosure provides a compound according to any of the foregoing embodiments wherein $R^1$ is optionally substituted by one or more substituents independently selected from —CH$_3$ or —OCHF$_2$.

In a twelfth embodiment, the disclosure provides a compound according to any of the foregoing embodiments wherein $R^{2a}$ is optionally substituted pyrimidinyl or optionally substituted dihydropyranyl.

In a thirteenth embodiment, the disclosure provides a compound according any of the foregoing embodiments wherein $R^{2a}$ is 1,2,4-oxadiazolyl, optionally substituted pyrazolyl, optionally substituted pyridinyl, optionally substituted pyrimidinyl, or optionally substituted 1,2,4-thiadiazolyl.

In a fourteenth embodiment, the disclosure provides a compound according to any of the foregoing embodiments wherein $R^{2b}$ is N($R^a$)($R^b$), optionally substituted ($C_1$-$C_4$)alkyl, optionally substituted morpholinyl, optionally substituted piperazinyl, optionally substituted piperidinyl, 1,1-dioxidothiomorpholinyl, optionally substituted hexahydroimidazo[1,5-a]pyrazin-3(2H)-one, optionally substituted 7-azaspiro[3.5]nonane, or optionally substituted pyrrolidinyl.

In a fifteenth embodiment, the disclosure provides a compound according to any of the foregoing embodiments wherein $R^{2b}$ is —N($R^a$)($R^b$), optionally substituted ($C_1$-$C_3$) alkyl, optionally substituted 7-azaspiro[3.5]nonanyl, optionally substituted morpholinyl, 1,1-dioxidothiomorpholinyl, optionally substituted piperazinyl, optionally substituted piperidinyl, hexahydroimidazo[1,5-a]pyrazin-3(2H)-one, or optionally substituted pyrrolidinyl; wherein $R^a$ is H or ($C_1$-$C_3$)alkyl, and $R^b$ is optionally substituted ($C_1$-$C_3$)alkyl, methoxypropyl, -5-oxopyrrolidin-3-ylmethyl, or tetrahydrofuranyl.

In a sixteenth embodiment, the disclosure provides a compound according to any of the foregoing embodiments wherein $R^{2b}$ is optionally substituted ($C_1$-$C_3$)alkyl, —CH$_2$-pyrazolyl or —CH$_2$-triazolyl.

In a seventeenth embodiment, the disclosure provides a compound according any of the foregoing embodiments wherein $R^{2b}$ is optionally substituted ($C_1$-$C_3$)alkyl, optionally substituted 7-azaspiro[3.5]nonanyl, optionally substituted morpholinyl, or hexahydroimidazo[1,5-a]pyrazin-3 (2H)-one.

In a eighteenth embodiment, the disclosure provides a compound according to any of the foregoing embodiments wherein $R^{2b}$ is optionally substituted by —CH$_2$OH, —C(OH)(CH$_3$)$_2$, —C(O)CH$_3$, —C(O)OH, —OH, or alkoxyalkyl In a nineteenth embodiment, the disclosure provides a compound according to any of the foregoing embodiments wherein $R^{2b}$ is optionally substituted by one or more substituents independently selected from CH$_3$, —C(O)CH$_2$OH, —C(O)CH$_3$.

In a twentieth embodiment, the disclosure provides a compound according to any of the foregoing embodiments, wherein the compound is:

3-(2-(Difluoromethoxy)phenyl)-6-(2-morpholinopyrimidin-5-yl)-2,3-dihydropyrazolo[1,2-a]indazol-9(1H)-one;

(R)-3-(2-(difluoromethoxy)phenyl)-6-(2-morpholinopyrimidin-5-yl)-2,3-dihydropyrazolo[1,2-a]indazol-9(1H)-one;

(S)-3-(2-(difluoromethoxy)phenyl)-6-(2-morpholinopyrimidin-5-yl)-2,3-dihydropyrazolo[1,2-a]indazol-9(1H)-one;

1-(5-(3-(2-(difluoromethoxy)phenyl)-9-oxo-1,2,3,9-tetrahydropyrazolo[1,2-a]indazol-6-yl)pyrimidin-2-yl)piperidine-4-carboxylic acid;

(S)-3-(2-(difluoromethoxy)phenyl)-6-(2-((R)-2-(methoxymethyl)pyrrolidin-1-yl)pyrimidin-5-yl)-2,3-dihydropyrazolo[1,2-a]indazol-9(1H)-one;

(R)-3-(2-(difluoromethoxy)phenyl)-6-(2-((R)-2-(methoxymethyl)pyrrolidin-1-yl)pyrimidin-5-yl)-2,3-dihydropyrazolo[1,2-a]indazol-9(1H)-one;

(R)-3-(2-(difluoromethoxy)phenyl)-6-(2-(((R)-tetrahydrofuran-3-yl)amino)pyrimidin-5-yl)-2,3-dihydropyrazolo[1,2-a]indazol-9(1H)-one;

(S)-3-(2-(difluoromethoxy)phenyl)-6-(2-(((R)-tetrahydrofuran-3-yl)amino)pyrimidin-5-yl)-2,3-dihydropyrazolo[1,2-a]indazol-9(1H)-one;

(R)-3-(2-(difluoromethoxy)phenyl)-6-(2-((R)-2-(hydroxymethyl)morpholino)pyrimidin-5-yl)-2,3-dihydropyrazolo[1,2-a]indazol-9(1H)-one;

(S)-3-(2-(difluoromethoxy)phenyl)-6-(2-((R)-2-(hydroxymethyl)morpholino)pyrimidin-5-yl)-2,3-dihydropyrazolo[1,2-a]indazol-9(1H)-one;

(S)-3-(2-(difluoromethoxy)phenyl)-6-(2-((S)-2-(hydroxymethyl)morpholino)pyrimidin-5-yl)-2,3-dihydropyrazolo[1,2-a]indazol-9(1H)-one;

(R)-3-(2-(difluoromethoxy)phenyl)-6-(2-((S)-2-(hydroxymethyl)morpholino)pyrimidin-5-yl)-2,3-dihydropyrazolo[1,2-a]indazol-9(1H)-one;

(R)-3-(2-(Difluoromethoxy)phenyl)-6-(2-(2-hydroxypropan-2-yl)pyrimidin-5-yl)-2,3-dihydropyrazolo[1,2-a]indazol-9(1H)-one;

(S)-3-(2-(difluoromethoxy)phenyl)-6-(2-(2-hydroxypropan-2-yl)pyrimidin-5-yl)-2,3-dihydropyrazolo[1,2-a]indazol-9(1H)-one;

3-(2-(difluoromethoxy)phenyl)-6-(2-(4-hydroxypiperidin-1-yl)pyrimidin-5-yl)-2,3-dihydropyrazolo[1,2-a]indazol-9(1H)-one;

(R)-3-(2-(difluoromethoxy)phenyl)-6-(2-((((S)-5-oxopyrrolidin-3-yl)methyl)amino)pyrimidin-5-yl)-2,3-dihydropyrazolo[1,2-a]indazol-9(1H)-one;

(S)-3-(2-(difluoromethoxy)phenyl)-6-(2-((((S)-5-oxopyrrolidin-3-yl)methyl)amino)pyrimidin-5-yl)-2,3-dihydropyrazolo[1,2-a]indazol-9(1H)-one;

(R)-3-(2-(difluoromethoxy)phenyl)-6-(2-((((R)-5-oxopyrrolidin-3-yl)methyl)amino)pyrimidin-5-yl)-2,3-dihydropyrazolo[1,2-a]indazol-9(1H)-one;

(S)-3-(2-(difluoromethoxy)phenyl)-6-(2-((((R)-5-oxopyrrolidin-3-yl)methyl)amino)pyrimidin-5-yl)-2,3-dihydropyrazolo[1,2-a]indazol-9(1H)-one;

(R)-3-(2-(difluoromethoxy)phenyl)-6-(2-(2-hydroxy-7-azaspiro[3.5]nonan-7-yl)pyrimidin-5-yl)-2,3-dihydropyrazolo[1,2-a]indazol-9(1H)-one;

(S)-3-(2-(difluoromethoxy)phenyl)-6-(2-(2-hydroxy-7-azaspiro[3.5]nonan-7-yl)pyrimidin-5-yl)-2,3-dihydropyrazolo[1,2-a]indazol-9(1H)-one;

(S)-3-(2-(difluoromethoxy)phenyl)-6-(2-((S)-3-oxohexahydroimidazo[1,5-a]pyrazin-7(1H)-yl)pyrimidin-5-yl)-2,3-dihydropyrazolo[1,2-a]indazol-9(1H)-one;

(S)-3-(2-(difluoromethoxy)phenyl)-6-(2-((R)-3-oxohexahydroimidazo[1,5-a]pyrazin-7(1H)-yl)pyrimidin-5-yl)-2,3-dihydropyrazolo[1,2-a]indazol-9(1H)-one;

(R)-3-(2-(difluoromethoxy)phenyl)-6-(2-((S)-3-oxohexahydroimidazo[1,5-a]pyrazin-7(1H)-yl)pyrimidin-5-yl)-2,3-dihydropyrazolo[1,2-a]indazol-9(1H)-one;

(R)-3-(2-(difluoromethoxy)phenyl)-6-(2-((R)-3-oxohexahydroimidazo[1,5-a]pyrazin-7(1H)-yl)pyrimidin-5-yl)-2,3-dihydropyrazolo[1,2-a]indazol-9(1H)-one;

(R)-3-(2-(Difluoromethoxy)phenyl)-6-(2-((3-methoxypropyl)amino)pyrimidin-5-yl)-2,3-dihydropyrazolo[1,2-a]indazol-9(1H)-one;

(S)-3-(2-(Difluoromethoxy)phenyl)-6-(2-((3-methoxypropyl)amino)pyrimidin-5-yl)-2,3-dihydropyrazolo[1,2-a]indazol-9(1H)-one;

(S)-6-(2-(4-Acetylpiperazin-1-yl)pyrimidin-5-yl)-3-(2-(difluoromethoxy)phenyl)-2,3-dihydropyrazolo[1,2-a]indazol-9(1H)-one;

(R)-6-(2-(4-Acetylpiperazin-1-yl)pyrimidin-5-yl)-3-(2-(difluoromethoxy)phenyl)-2,3-dihydropyrazolo[1,2-a]indazol-9(1H)-one;

6-(2-(difluoromethoxy)phenyl)-3-(2-morpholinopyrimidin-5-yl)-8,9-dihydro-6H-pyridazino[1,2-a]indazol-11(7H)-one;

6-(2-(difluoromethoxy)phenyl)-3-(2-(4-hydroxypiperidin-1-yl)pyrimidin-5-yl)-8,9-dihydro-6H-pyridazino[1,2-a]indazol-11(7H)-one;

6-(2-(difluoromethoxy)phenyl)-3-(2-(1,1-dioxidothiomorpholino)pyrimidin-5-yl)-8,9-dihydro-6H-pyridazino[1,2-a]indazol-11(7H)-one;

3-(2-methoxyphenyl)-6-(2-morpholinopyrimidin-5-yl)-2,3-dihydropyrazolo[1,2-a]indazol-9(1H)-one;

(R)-6-(2-(2-hydroxypropan-2-yl)pyrimidin-5-yl)-3-(2-methoxyphenyl)-2,3-dihydropyrazolo[1,2-a]indazol-9(1H)-one;

(S)-6-(2-(2-hydroxypropan-2-yl)pyrimidin-5-yl)-3-(2-methoxyphenyl)-2,3-dihydropyrazolo[1,2-a]indazol-9(1H)-one;

2-methyl-6-(6-(2-morpholinopyrimidin-5-yl)-9-oxo-1,2,3,9-tetrahydropyrazolo[1,2-a]indazol-3-yl)benzonitrile;

6-(2-morpholinopyrimidin-5-yl)-3-phenyl-2,3-dihydropyrazolo[1,2-a]indazol-9(1H)-one;

4-methoxy-3-(6-(2-morpholinopyrimidin-5-yl)-9-oxo-1,2,3,9-tetrahydropyrazolo[1,2-a]indazol-3-yl)benzonitrile;

2-methoxy-3-(6-(2-morpholinopyrimidin-5-yl)-9-oxo-1,2,3,9-tetrahydropyrazolo[1,2-a]indazol-3-yl)benzonitrile;

3-(1-isopropyl-1H-pyrazol-5-yl)-6-(2-morpholinopyrimidin-5-yl)-2,3-dihydropyrazolo[1,2-a]indazol-9(1H)-one;

2-methyl-6-(6-(2-morpholinopyrimidin-5-yl)-9-oxo-1,2,3,9-tetrahydropyrazolo[1,2-a]indazol-3-yl)benzamide;

rac-(1R,9bR)-1-(2-(difluoromethoxy)phenyl)-8-(2-morpholinopyrimidin-5-yl)-2,3-dihydro-1H-pyrrolo[2,1-a]isoindol-5(9bH)-one;

rac-(1R,9bS)-1-(2-(difluoromethoxy)phenyl)-8-(2-morpholinopyrimidin-5-yl)-2,3-dihydro-1H-pyrrolo[2,1-a]isoindol-5(9bH)-one;

rac-(1R,10bR)-1-(2-(difluoromethoxy)phenyl)-9-(2-morpholinopyrimidin-5-yl)-3,4-dihydro-1H-[1,4]oxazino[3,4-a]isoindol-6(10bH)-one;

(1S,9bS)-1-(2-(difluoromethoxy)phenyl)-8-(2-morpholinopyrimidin-5-yl)-2,3-dihydro-1H-pyrrolo[2,1-a]isoindol-5(9bH)-one;

(1R,9bR)-1-(2-(difluoromethoxy)phenyl)-8-(2-morpholinopyrimidin-5-yl)-2,3-dihydro-1H-pyrrolo[2,1-a]isoindol-5(9bH)-one;

(1S,9bS)-1-(2-(difluoromethoxy)phenyl)-8-(2-(2-hydroxypropan-2-yl)pyrimidin-5-yl)-2,3-dihydro-1H-pyrrolo[2,1-a]isoindol-5(9bH)-one;

(1R,9bR)-1-(2-(difluoromethoxy)phenyl)-8-(2-(2-hydroxypropan-2-yl)pyrimidin-5-yl)-2,3-dihydro-1H-pyrrolo[2,1-a]isoindol-5(9bH)-one;

(1S,9bS)-1-(2-(difluoromethoxy)phenyl)-8-(2-((R)-2-(methoxymethyl)pyrrolidin-1-yl)pyrimidin-5-yl)-2,3-dihydro-1H-pyrrolo[2,1-a]isoindol-5(9bH)-one;

(1R,9bR)-1-(2-(difluoromethoxy)phenyl)-8-(2-((R)-2-(methoxymethyl)pyrrolidin-1-yl)pyrimidin-5-yl)-2,3-dihydro-1H-pyrrolo[2,1-a]isoindol-5(9bH)-one;

(1R,9bR)-1-(2-(difluoromethoxy)phenyl)-8-(2-((R)-3-oxohexahydroimidazo[1,5-a]pyrazin-7(1H)-yl)pyrimidin-5-yl)-2,3-dihydro-1H-pyrrolo[2,1-a]isoindol-5(9bH)-one;

(1R,9bR)-1-(2-(difluoromethoxy)phenyl)-8-(2-((S)-3-oxohexahydroimidazo[1,5-a]pyrazin-7(1H)-yl)pyrimidin-5-yl)-2,3-dihydro-1H-pyrrolo[2,1-a]isoindol-5(9bH)-one;

(1R)-1-(2-(difluoromethoxy)phenyl)-8-(2-(2-hydroxypropan-2-yl)-4-methylpyrimidin-5-yl)-2,3-dihydro-1H-pyrrolo[2,1-a]isoindol-5(9bH)-one;

(R)-6-(2-((R)-4-acetyl-2-methylpiperazin-1-yl)pyrimidin-5-yl)-3-(2-(difluoromethoxy)phenyl)-2,3-dihydropyrazolo[1,2-a]indazol-9(1H)-one;

(S)-3-(2-(difluoromethoxy)phenyl)-6-(2-((S)-3-oxohexahydroimidazo[1,5-a]pyrazin-7(1H)-yl)pyrimidin-5-yl)-2,3-dihydropyrazolo[1,2-a]indazol-9(1H)-one;

(R)-3-(2-(difluoromethoxy)-5-methylphenyl)-6-(2-(2-hydroxypropan-2-yl)pyrimidin-5-yl)-2,3-dihydropyrazolo[1,2-a]indazol-9(1H)-one;

(R)-6-(2-((R)-4-acetyl-3-methylpiperazin-1-yl)pyrimidin-5-yl)-3-(2-(difluoromethoxy)phenyl)-2,3-dihydropyrazolo[1,2-a]indazol-9(1H)-one;
(R)-3-(2-(difluoromethoxy)-5-methylphenyl)-6-(2-((S)-3-oxohexahydroimidazo[1,5-a]pyrazin-7(1H)-yl)pyrimidin-5-yl)-2,3-dihydropyrazolo[1,2-a]indazol-9(1H)-one;
(R)-3-(2-(difluoromethoxy)phenyl)-6-(2-((R)-4-(2-hydroxyacetyl)-3-methylpiperazin-1-yl)pyrimidin-5-yl)-2,3-dihydropyrazolo[1,2-a]indazol-9(1H)-one;
(R)-3-(2-(difluoromethoxy)-5-methylphenyl)-6-(2-(2-hydroxypropan-2-yl)pyrimidin-5-yl)-2,3-dihydropyrazolo[1,2-a]indazol-9(1H)-one;
(S)-3-(2-(difluoromethoxy)phenyl)-6-(2-((S)-3-oxohexahydroimidazo[1,5-a]pyrazin-7(1H)-yl)pyrimidin-5-yl)-2,3-dihydropyrazolo[1,2-a]indazol-9(1H)-one;
(S)-3-(2-(difluoromethoxy)phenyl)-6-(2-(2-hydroxypropan-2-yl)pyrimidin-5-yl)-2,3-dihydropyrazolo[1,2-a]indazol-9(1H)-one;
(R)-3-(2-(difluoromethoxy)phenyl)-6-(2-((R)-3-hydroxy-4-(2-hydroxyacetyl)piperazin-1-yl)pyrimidin-5-yl)-2,3-dihydro-1H,9H-pyrazolo[1,2-a]indazol-9-one;
is (1R)-1-(2-(difluoromethoxy)phenyl)-8-(2-(2-hydroxypropan-2-yl)-4-methylpyrimidin-5-yl)-2,3-dihydro-1H-pyrrolo[2,1-a]isoindol-5(9bH)-one;
(S)-3-(2-(difluoromethoxy)-5-methylphenyl)-7-fluoro-6-(2-(2-hydroxypropan-2-yl)pyrimidin-5-yl)-2,3-dihydropyrazolo[1,2-a]indazol-9(1H)-one;
(R)-3-(2-(difluoromethoxy)-5-methylphenyl)-7-fluoro-6-(2-(2-hydroxypropan-2-yl)pyrimidin-5-yl)-2,3-dihydropyrazolo[1,2-a]indazol-9(1H)-one;
(R)-3-(2-(difluoromethoxy)phenyl)-7-fluoro-6-(2-(2-hydroxypropan-2-yl)pyrimidin-5-yl)-2,3-dihydropyrazolo[1,2-a]indazol-9(1H)-one;
(S)-3-(2-(difluoromethoxy)phenyl)-7-fluoro-6-(2-(2-hydroxypropan-2-yl)pyrimidin-5-yl)-2,3-dihydropyrazolo[1,2-a]indazol-9(1H)-one;
3-(5-(hydroxymethyl)-2-methoxyphenyl)-6-(2-morpholinopyrimidin-5-yl)-2,3-dihydropyrazolo[1,2-a]indazol-9(1H)-one;
(R)-3-(2-(difluoromethoxy)-5-methylphenyl)-7-fluoro-6-(2-(2-hydroxypropan-2-yl)pyrimidin-5-yl)-2,3-dihydro-1H,9H-pyrazolo[1,2-a]indazol-9-one;
(S)-3-(2-(difluoromethoxy)-5-methylphenyl)-7-fluoro-6-(2-(2-hydroxypropan-2-yl)pyrimidin-5-yl)-2,3-dihydro-1H,9H-pyrazolo[1,2-a]indazol-9-one;
(S)-3-(2-(difluoromethoxy)phenyl)-6-(2-(2-hydroxypropan-2-yl)pyrimidin-5-yl)-2,3-dihydro-1H,9H-pyrazolo[1,2-a]indazol-9-one;
(R)-3-(2-(difluoromethoxy)-5-methylphenyl)-6-(2-((S)-3-oxohexahydroimidazo[1,5-a]pyrazin-7(1H)-yl)pyrimidin-5-yl)-2,3-dihydro-1H,9H-pyrazolo[1,2-a]indazol-9-one;
(R)-3-(2-(difluoromethoxy)-5-methylphenyl)-6-(2-(2-hydroxypropan-2-yl)pyrimidin-5-yl)-2,3-dihydro-1H,9H-pyrazolo[1,2-a]indazol-9-one;
(R)-6-(2-((R)-4-acetyl-3-methylpiperazin-1-yl)pyrimidin-5-yl)-3-(2-(difluoromethoxy)phenyl)-2,3-dihydropyrazolo[1,2-a]indazol-9(1H)-one;
(R)-3-(2-(difluoromethoxy)phenyl)-6-(2-((R)-3-hydroxy-4-(2-hydroxyacetyl)piperazin-1-yl)pyrimidin-5-yl)-2,3-dihydropyrazolo[1,2-a]indazol-9(1H)-one;
9b-(2-methoxyphenyl)-8-(2-morpholinopyrimidin-5-yl)-2,3-dihydro-1H-pyrrolo[2,1-a]isoindol-5(9bH)-one; or
3-(5-(hydroxymethyl)-2-methoxyphenyl)-6-(2-morpholinopyrimidin-5-yl)-2,3-dihydropyrazolo[1,2-a]indazol-9(1H)-one.

In a twenty-first embodiment, the disclosure provides a pharmaceutical composition comprising a compound of Formula (I) and pharmaceutically acceptable excipients.

In a twenty-second embodiment, the disclosure provides a method of treating a disease comprising administering a therapeutically effective amount of a compound of Formula (I).

In a twenty-third embodiment, the disclosure provides a method according to the twenty-second embodiment wherein the disease is rheumatoid arthritis, juvenile rheumatoid arthritis, psoriasis, psoriatic arthritis, Crohn's disease, inflammatory bowel disease, ulcerative colitis, psoriatic arthritis, psoriasis, ankylosing spondylitis, systemic lupus erythematosus, lupus nephritis, multiple sclerosis, uveitis, or hidraenitis suppurativa.

In a twenty-fourth embodiment, the disclosure provides a kit comprising a packaged product comprising components with which to administer a compound according to any of the first through twenty-eighth embodiments for treatment of an autoimmune disorder.

In a twenty-fifth embodiment, the disclosure provides a kit according to the thirty-sixth embodiment, wherein the packaged product comprises a compound according to any of the first through twentieth embodiment and instructions for use.

In a twenty-sixth embodiment, the disclosure provides a pharmaceutical composition comprising a compound according to any of the first through twentieth embodiments and one or more pharmaceutically acceptable excipients.

DETAILED DESCRIPTION OF THE DISCLOSURE

Many autoimmune diseases and disease associated with chronic inflammation, as well as acute responses, have been linked to excessive or unregulated production or activity of one or more cytokines.

The compounds of the disclosure are also useful in the treatment of rheumatoid arthritis, asthma, allergic asthma, osteoarthritis, juvenile arthritis, ankylosing spondylitis, hidradenitis supportive, juvenile rheumatoid arthritis, ankylosing spondylitis associated lung disease, Sjögren's syndrome, Compounds of Formula (I) of the disclosure can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present disclosure. The additional agent also can be an agent that imparts a beneficial attribute to the therapeutic composition e.g., an agent that affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the compounds of the present disclosure and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this disclosure. Non-limiting examples of therapeutic agents for rheumatoid arthritis with which a compound of Formula (I) of the disclosure can be combined include the following: cytokine suppressive anti-inflammatory drug(s) (CSAIDs); antibodies to or antagonists of other human cytokines or growth factors, for example, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, MMP-13 and PDGF. Compounds of the disclosure can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the disclosure may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as IL-1 (e.g., NIK, IKK, JAK1, JAK2, JAK3, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. sIL-1RI, sIL-1RII, sIL-6R), antiinflammatory cytokines (e.g. IL-4, IL-10, IL-11, IL-13), celecoxib, folic acid, hydroxychloroquine sulfate, rofecoxib, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, tofacitinib, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. Preferred combinations include methotrexate or leflunomide and in moderate or severe rheumatoid arthritis cases, and cyclosporine.

Non-limiting examples of therapeutic agents for inflammatory bowel disease with which a compound of Formula (I) of the disclosure can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies; growth factors; elastase inhibitors; pyridinyl-imidazole compounds; antibodies to or antagonists of other human cytokines or growth factors, for example, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as IL-1 (e.g. NIK, IKK, p38 or MAP kinase inhibitors); IL-1β converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. sIL-1RI, sIL-1RII, sIL-6R) and antiinflammatory cytokines (e.g. IL-4, IL-10, IL-11, IL-13). Preferred examples of therapeutic agents for Crohn's disease with which a compound of Formula (I) can be combined include PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrosewater; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, LT, IL-1, IL-2, IL-6, IL-7, IL-8, IL-12, IL-23, IL-15, IL-16, EMAP-II, GM-CSF, FGF, and PDGF. A compound of Formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (I) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as IL-1 (e.g., NIK, IKK, p38 or MAP kinase inhibitors). IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. sIL-1RI, sIL-1RII, sIL-6R) and antiinflammatory cytokines (e.g. IL-4, IL-10, IL-13 and TGFβ).

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, and prednisone Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, and alefacept In this disclosure, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (I) which have acidic substituents may exist as salts with pharmaceutically acceptable bases. The present disclosure includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present disclosure includes each crystal form and mixtures thereof.

Certain compounds of Formula (I) and their salts may also exist in the form of solvates, for example hydrates, and the present disclosure includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present disclosure includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present disclosure includes each diastereoisomer of compounds of Formula (I) (and mixtures thereof.

Certain compounds of Formula (I) may exist in different tautomeric forms or as different geometric isomers, and the present disclosure includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present disclosure includes each conformational isomer of compounds of Formula (I) and mixtures thereof.

Certain compounds of Formula (I) may exist in zwitterionic form and the present disclosure includes each zwitterionic form of compounds of Formula (I) (and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present disclosure wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this disclosure include but are not limited to carboxylic acid substituents wherein the free hydrogen is replaced by ($C_1$-$C_4$)alkyl, ($C_1$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylamino-ethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$)alkyl.

Other exemplary pro-drugs release an alcohol of Formula (I) wherein the free hydrogen of the hydroxyl substituent (e.g., $R^1$ contains hydroxyl) is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_{12}$)alkoxycarbonyloxymethyl, N—($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, P(O)(OH)$_2$, —P(O)(O($C_1$-$C_6$)alkyl)$_2$ or glycosyl (the radical resulting from detachment of the hydroxyl of the hemiacetal of a carbohydrate).

The term "heterocyclic," "heterocyclyl" or "heterocyclylene," as used herein, include non-aromatic, ring systems, including, but not limited to, monocyclic, bicyclic, tricyclic and spirocyclic rings, which can be completely saturated or which can contain one or more units of unsaturation, for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this disclosure, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this disclosure: azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrazolyl, thiadiazolyl, thienyl, 6H-pyrrolo[2,3-e][1,2,4]triazolo[4,3-a]pyrazinyl, 6H-imidazo[1,5-a]pyrrolo[2,3-e]pyrazinyl, 1,6-dihydropyrazolo[3,4-d]pyrrolo[2,3-b]pyridine, 3H-3,4,6,8a-tetraaza-asindacenyl, 3H-imidazo[1,2-a]pyrrolo[2,3-e]pyrazinyl, pyrazolo[3,4-d]pyrrolo[2,3-b]pyridinyl, 1,6-dihydro-1,2,5,6-tetraza-as-indacenyl, 3H-3,4,8a-triaza-as-indacenyl, 6H-3-oxa-2,5,6-triaza-as-indacenyl, 3,6-dihydro-2,3,6-tetraaza-as-indacenyl, 1,6-dihydro-dipyrrolo[2,3-b;2'3'-d]pyridinyl, 6H-3-thia-2,5,6-triaza-as-indacenyl, 4,5-dihydro-1H-benzo[b]azepin-2 (3H)-one, 3,4-dihydroquinolin-2(1H)-one, 2H-benzo[b][1,4]oxazin-3(4H)-one, or 6,7-dihydro-4H-pyrazolo[5,1-c][1,4]oxazinyl or 1,6-dihydroimidazo[4,5-d]pyrrolo[2,3-b] pyridine.

As used herein, "alkyl," "alkylene" or notations such as "($C_1$-$C_8$)" include straight chained or branched hydrocarbons which are completely saturated. Examples of alkyls are methyl, ethyl, propyl, isopropyl, butyl, pentyl, hexyl and isomers thereof. As used herein, "alkenyl," "alkenylene," "alkynylene" and "alkynyl" means $C_2$-$C_8$ and includes straight chained or branched hydrocarbons which contain one or more units of unsaturation, one or more double bonds for alkenyl and one or more triple bonds for alkynyl.

As used herein, "aromatic" groups (or "aryl" or "arylene" groups) include aromatic carbocyclic ring systems (e.g. phenyl) and fused polycyclic aromatic ring systems (e.g. naphthyl, biphenyl and 1,2,3,4-tetrahydronaphthyl).

As used herein, "cycloalkyl" or "cycloalkylene" means $C_3$-$C_{12}$ monocyclic or multicyclic (e.g., bicyclic, tricyclic, spirocyclic, etc.) hydrocarbons that is completely saturated. Examples of a cycloalkyl group are cyclopropyl, cyclobutyl, cyclopentyl, bicyclo[1.1.1]pentyl, and cyclohexyl.

As used herein, "cycloalkenyl" means $C_3$-$C_{12}$ monocyclic or multicyclic (e.g., bicyclic, tricyclic, spirocyclic, etc.) hydrocarbons that has one or more unsaturated bonds but does not amount to an aromatic group. Examples of a cycloalkenyl group are cyclopentenyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this disclosure, some examples of groups that are substituents are: ($C_1$-$C_8$)alkyl groups, ($C_2$-$C_8$)alkenyl groups, ($C_2$-$C_8$)alkynyl groups, ($C_3$-$C_{10}$)cycloalkyl groups, halogen (F, Cl, Br or I), halogenated ($C_1$-$C_8$)alkyl groups (for example but not limited to —$CF_3$), —O—($C_1$-$C_8$)alkyl groups, =O, =$CH_2$, —OH, —$CH_2$OH, —$CH_2$O$CH_3$, —$CH_2$N$H_2$, ($C_1$-$C_4$)alkyl-OH, —$CH_2$$CH_2$O$CH_2$$CH_3$, —S—($C_1$-$C_8$)alkyl groups, —SH, —NH($C_1$-$C_8$)alkyl groups, —N(($C_1$-$C_8$)alkyl)$_2$ groups, —N$H_2$, —C(O)N$H_2$, —$CH_2$NHC(O)($C_1$-$C_4$)alkyl, —$CH_2$NHC(O)$CH_2$Cl, —$CH_2$NHC(O)$CH_2$CN, —$CH_2$NHC(O)$CH_2$$CH_2$N($CH_3$)$_2$, —$CH_2$NHC(O)C(=$CH_2$)$CH_3$, —$CH_2$NHC(O)($C_2$-$C_4$)alkynyl, —$CH_2$NHC(O)$CH_2$$CH_2$-piperidinyl, —($C_1$-$C_4$)alkyl-morpholinyl, —$CH_2$NHC(O)$CH_2$O-phenyl wherein the phenyl is optionally substituted with halogen, ($C_1$-$C_4$)alkoxy, —C(O)($C_1$-$C_4$)alkyl, —C(O)($C_1$-$C_4$)alkoxy, —C(O)N(H)$_2$, —C(O)N($CH_3$)$_2$, —C(O)($C_1$-$C_6$)heteroaryl, —N($CH_3$)$_2$, —NHC(O)($C_1$-$C_4$)alkyl, —NHC(O)($C_2$-$C_4$)alkenyl, —NHC(O)$CH_2$CN, —S(O)$_2$($C_1$-$C_4$)alkyl, —S(O)$_2$($C_1$-$C_6$)heteroaryl, —S(O)$_2$($C_1$-$C_6$)heterocyclyl, 4-methylpiperazinecarbonyl, —($C_1$-$C_4$)alkylC(O)N$H_2$, —C(O)NH($C_1$-$C_8$)alkyl groups, —C(O)N(($C_1$-$C_8$)alkyl)$_2$, —C(O)N(H)($C_3$-$C_8$)cycloalkyl groups, —C(O)($C_1$-$C_4$)alkyl-OH, —($C_1$-$C_4$)alkyl($C_1$-$C_4$)alkoxy, —NHC(O)H, —NHC(O)($C_1$-$C_8$)alkyl groups, —NHC(O)($C_3$-$C_8$)cycloalkyl groups, —N(($C_1$-$C_8$)alkyl)C(O)H, —N(($C_1$-$C_8$)alkyl)C(O)($C_1$-$C_8$)alkyl groups, —NHC(O)N$H_2$, —NHC(O)NH($C_1$-$C_8$)alkyl groups, —N(($C_1$-$C_8$)alkyl)C(O)N$H_2$ groups. —NHC(O)N(($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —NH$CH_2$-heteroaryl, benzyl, —O$CH_2$-heteroaryl, —C(O)H, —C(O)($C_1$-$C_8$)alkyl groups, —CN, —N$O_2$, —S(O)($C_1$-$C_8$)alkyl groups, —S(O)$_2$($C_1$-$C_8$)alkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2$N$H_2$ groups, —NHS(O)$_2$($C_1$-$C_8$)alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups-, —O—($C_1$-$C_8$)alkyl-O—($C_1$-$C_8$)alkyl groups, —C(O)OH, —C(O)O($C_1$-$C_8$)alkyl groups, NHOH, NHO($C_1$-$C_8$)alkyl groups, —O-halogenated ($C_1$-$C_8$)alkyl groups (for example but not limited to —OC$F_3$), —S(O)$_2$-halogenated ($C_1$-$C_8$)alkyl groups (for example but not limited to —S(O)$_2$C$F_3$), —S-halogenated ($C_1$-$C_8$)alkyl groups (for example but not limited to —SC$F_3$), —($C_1$-$C_6$)heterocyclyl (for example but not limited to pyrrolidine, tetrahydrofuran, pyran or morpholine), —($C_1$-$C_6$)heteroaryl (for example but not limited to tetrazole, imidazole, furan, pyrazine or pyrazole), -phenyl, optionally substituted benzyl, —NHC(O)O—($C_1$-$C_6$)alkyl groups, —N(($C_1$-$C_6$)alkyl)C(O)O—($C_1$-$C_6$)alkyl groups, —C(=NH)—($C_1$-$C_6$)alkyl groups, —C(=NOH)—($C_1$-$C_6$)alkyl groups, or —C(=N—O—($C_1$-$C_8$)alkyl)-($C_1$-$C_6$)alkyl groups.

The term "kit" as used herein refers to a packaged product comprising components with which to administer a compound of Formula (I) of the disclosure for treatment of an autoimmune disorder. The kit preferably comprises a box or container that holds the components of the kit. The box or container is affixed with a label or a Food and Drug Administration approved protocol. The box or container holds components of the disclosure which are preferably contained within plastic, polyethylene, polypropylene, ethylene, or propylene vessels. The vessels can be capped-tubes or bottles. The kit can also include instructions for administering a compound of Formula (I).

One or more compounds of this disclosure can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present disclosure may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present disclosure thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the disclosure may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present disclosure are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the disclosure is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the disclosure may be provided as salts with pharmaceutically compatible counter ions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present disclosure include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present disclosure, the therapeutically effective dose can be estimated initially from cellular assays. For example, a dose can be formulated in cellular and animal models to achieve a circulating concentration range that includes the $IC_{50}$ as determined in cellular assays (e.g., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see, e.g., Fingl et al., 1975, in *The Pharmacological Basis of Therapeutics*, Ch. 1, p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the disclosure formulated in a compatible pharmaceutical carrier may also be prepared, placed in an appropriate container, and labelled for treatment of an indicated condition.

In some formulations it may be beneficial to use the compounds of the present disclosure in the form of particles of very small size, for example as obtained by fluid energy milling.

The use of compounds of the present disclosure in the manufacture of pharmaceutical compositions is illustrated by the following description. In this description the term "active compound" denotes any compound of the disclosure but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present disclosure the active compound may, if desired, be associated with other compatible pharmacologically active ingredients. For example, the compounds of this disclosure can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the disclosure can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the disclosure and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present disclosure.

The present disclosure also comprises the use of a compound of Formula (I) as a medicament.

A further aspect of the present disclosure provides the use of a compound of Formula (I) or a salt thereof in the manufacture of a medicament for treating vascular hyperpermeability, angiogenesis-dependent disorders, proliferative diseases or disorders of the immune system in mammals, particularly human beings.

The present disclosure also provides a method of treating vascular hyperpermeability, inappropriate neovascularization, proliferative diseases and/or disorders of the immune system which comprises the administration of a therapeutically effective amount of a compound of Formula (I) to a mammal, particularly a human being, in need thereof.

ABBREVIATIONS

Ac Acetyl
AcOH Glacial acetic acid
Aq Aqueous
9-BBN 9-Borabicyclo[3.3.1]nonane
Boc t-Butoxycarbonyl
d Doublet
DEA Diethylamine
DIEA N,N-Diisopropylethylamine
DCM Dichloromethane (methylene chloride)
dd Doublet of doublets
DMA N,N-Dimethylacetamide
DMAP 4-Dimethylaminopyridine
DMF N,N-Dimethylformamide
DMSO Dimethyl sulfoxide
dppf 1,1'-Bis(diphenylphosphino)ferrocene
EDTA Ethylene diamine tetraacetic acid
Et$_2$O Diethyl ether
EtOAc Ethyl acetate
EtOH Ethanol
g Gram(s)
h Hour(s)
HATU 1-[Bis(dimethylamino)methylene]-1H-1,2,3-triazolo[4,5-b]pyridinium 3-oxid hexafluorophosphate
HEPES N-2-Hydroxyethylpiperazine-N'-2-ethanesulfonic acid
HPLC High-pressure liquid chromatography
IPA Isopropyl alcohol
KOAc Potassium acetate
LC/MS Liquid chromatography/mass spectrometry
LiHMDS Lithium bis(trimethylsilyl)amide
m Multiplet
M Molar
m-CPBA 3-Chloroperoxybenzoic acid
MeCN Acetonitrile
MeI Iodomethane
MeOH Methyl alcohol
min Minute(s)
mmol Millimole
MS Mass spectrometry
MsCl Methanesulfonyl chloride
n- Normal (nonbranched)
N Normal
NA Not obtained or not applicable
NaBH(OAc)$_3$ Sodium triacetoxyhydroborate
NBS N-Bromosuccinimide
NH$_4$OAc Ammonium acetate
NMO 4-Methylmorpholine N-oxide
NMP N-Methyl-2-pyrrolidinone
NMR Nuclear magnetic resonance
pH −log [H$^+$]
PdCl$_2$(PPh$_3$)$_2$ Bis(triphenylphosphine)palladium(II) dichloride
Pd(OAc)$_2$ Palladium(II) acetate
Pd(PPh$_3$)$_4$ Tetrakis(triphenylphosphine)palladium(0)
PPh$_3$ Triphenylphosphine
ppm Parts per million
q Quartet
R$_t$ Retention time
rt Room temperature
s Singlet
SFC Supercritical fluid chromatography
SPE Solid phase extraction
Soln Solution
SM Small molecule
t Triplet
TEA Triethylamine
tert- Tertiary
TNFα Tumor necrosis factor alpha
TFA Trifluoroacetic acid
THF Tetrahydrofuran
UV Ultraviolet
wt weight

TNFα FP Competitive Binding Assay

Solution Preparation

1. Assay Buffer: Prepare 1× Assay Buffer (Water with 47 mM HEPES, 47 mM NaCl, 0.9 mM EDTA, 0.0071% Triton X-100) by adding 25 mL of 1 M HEPES, 5 mL of 5 M NaCl, 1 mL of 0.5 M EDTA, and 375 µL of a 10% Triton X-100 stock to a fresh 500 mL bottle of water.
2. Assay Mixture: Prepare fresh Assay Mixture containing 20 nM TNFα trimer (60 nM protein) and 1 nM 2',7'-difluoro-3',6'-dihydroxy-N-(2-(2-(2-((4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1,9'-xanthene]-5-carboxamide probe in 1× Assay Buffer.

Compound Plate Preparation

Manual 12-Point 1:3 Dilution Plates: (384 Well Polypropylene Plates)

Top concentration of compounds, 10 mM in DMSO, dispensed in rows A-O in columns 1 and 13. Compounds are serially diluted 1:3 with DMSO in columns 2-12 or 14-24 using a 16-channel Matrix pipettor. Plates stored at −20° C.

Discovery Preps 12-Point 1:3 Dilution Plates: (384 Well Assay Plates)

Top concentration, 5 mM in DMSO, of compounds placed in rows A-O in columns 1 and 13. Compounds are serially diluted 1:3 with DMSO in columns 2-12 or 14-24. Compound solutions are dispensed into replicate assay plates at 410 nL per well. Plates stored at 4° C.

TNFα FP Competitive Binding Assay Protocol

1. Compound plates warmed to rt.
2. Fresh Assay Mixture is prepared.
3. Assay Mixture (20 µL) is dispensed each well of 384 assay plates using a Thermo Multidrop Combi or 16-channel Matrix pipettor. If Manual 12-point 1:3 Dilution Plates are to be tested, Assay Mix is dispensed into empty plates. Discovery Preps 12-point 1:3 Dilution Plates already contain 410 nL compound solution in DMSO.
4. For Manual 12-point 1:3 Dilution Plates, 0.7 µL is manually transferred using a 16-channel Matrix pipettor to replicate assay plates containing 20 µL Assay Mixture for a final top compound concentration of 338 µM (3.4% DMSO).
5. For Discovery Preps 12-point 1:3 Dilution Plates, 20 µL Assay Mixture added the 410 nL compound solution already in the plates yields a final top compound concentration of 100 µM (2.0% DMSO).
6. Background subtraction controls are wells P1-P8 containing only Assay Buffer. The low % inhibition controls are wells P9-P16 containing only Assay Mix. The high % inhibition are wells P17-P24 containing only 1 nM 2',7'-difluoro-3',6'-dihydroxy-N-(2-(2-(2-((4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1,9'-xanthene]-5-carboxamide probe in 1× Assay Buffer.
7. Plates are incubated at rt for 18-24 h in 37° C. incubator ($CO_2$ is off).
8. Prior to reading the assay, the plates are placed in a dark cabinet to equilibrate at rt for one hour.
9. Background-subtracted fluorescence polarization (mP) is measured using a PerkinElmer Envision plate reader.
10. Raw data is entered into Assay Explorer and dose-response curves are generated using a variable slope curve.

Supplies, Materials, and Reagents

| Item | Vendor | Catalog # |
|---|---|---|
| HEPES (1M) | Invitrogen | 15630-080 |
| EDTA (0.5M) | Invitrogen | 15575-038 |
| NaCl (5M) | Sigma | S5150 |
| Triton X-100 | Sigma | T8787 |
| Water | Invitrogen | 10977-015 |
| SM-antiTNFα OregonGreen488 probe | Abbvie | 2',7'-difluoro-3',6'-dihydroxy-N-(2-(2-(2-((4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1,9'-xanthene]-5-carboxamide |
| Corning 3676 Compound Plate: 384 Well Low Volume Black Round Bottom Polystyrene NBS | Corning | 3676 |

For the purpose of the Tables and Examples below, the FP binding assay $IC_{50}$ of each compound is expressed as follows: A=a compound with $IC_{50}$ less than 1 µM, B=a compound with $IC_{50}$ within the range of 1 µM to 10 µM, and C=a compound with a TNFα $IC_{50}$ greater than 10 µM.

SM-antiTNFα OregonGreen488 Probe

Preparation A:
2-(4-(Isoquinolin-8-yl)phenyl)ethanol

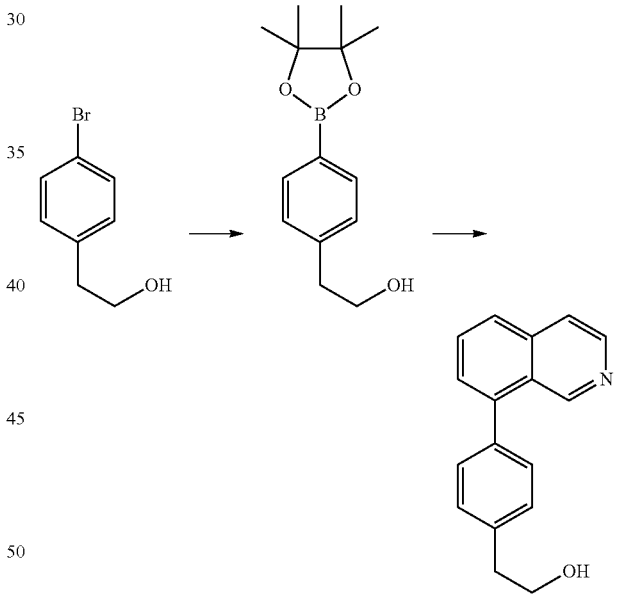

Step 1: 2-(4-(4,4,5,5-Tetramethyl-1,3,2-dioxaborolan-2-yl)phenyl)ethanol

Potassium acetate (4.88 g, 49.7 mmol), 4,4,4',4',5,5,5',5'-octamethyl-2,2'-bi(1,3,2-dioxaborolane) (7.6 g, 30 mmol) and $PdCl_2$(dppf) (0.91 g, 1.2 mmol) were added to a solution of 2-(4-bromophenyl)ethanol (5.0 g, 25 mmol) in 1,4-dioxane (100 mL) under $N_2$. The mixture was purged with $N_2$ then stirred under $N_2$ at about 85° C. for about 12 h. After cooling to rt, water (100 mL) was added and the mixture was extracted with EtOAc (2×100 mL). The combined organic layers were washed with saturated aqueous NaCl (100 mL) and dried over $Na_2SO_4$, filtered and concentrated under reduced pressure. The residue was purified via flash chromatography on silica gel (17% EtOAc/petroleum ether). The appropriate fractions were collected and concentrated under reduced pressure to give the title compound (6.2 g, 100%). $^1$H NMR (400 MHz, CDCl$_3$) δ 7.78 (d, J=7.9 Hz, 2H), 7.29-7.23 (m, 2H), 3.87 (t, J=6.6 Hz, 2H), 2.90 (t, J=6.6 Hz, 2H), 1.36 (s, 12H).

Step 2: 2-(4-(Isoquinolin-8-yl)phenyl)ethanol 1,1'-Bis(diphenylphosphino)ferrocenepalladium(II) dichloride dichloromethane complex (0.30 g, 0.40 mmol) was added to a mixture of 2-(4-(4,4,5,5-tetramethyl-1,3,2-dioxaborolan-2-yl)phenyl)ethanol (6.15 g, 24.8 mmol), 8-bromoisoquinoline (5.67 g, 27.3 mmol), cesium carbonate (16.6 g, 50.8 mmol), and 1,4-dioxane (60 mL) under N$_2$. The mixture was purged with N$_2$ and then stirred at about 95° C. for about 2 h. After cooling to rt, water (200 mL), chloroform (450 mL), and isopropyl alcohol (150 mL) were added then the layers were separated. The organic layer was dried over Na$_2$SO$_4$, filtered, and concentrated under reduced pressure. The residue was purified via flash chromatography on silica gel (0-100% EtOAc/heptane). The appropriate fractions were collected and concentrated under reduced pressure to give the title compound (3.72 g, 60%). MS m/z: 250 (M+H)$^+$.

Preparation B: Methyl 3-hydroxy-4-(isoquinolin-8-yl)benzoate

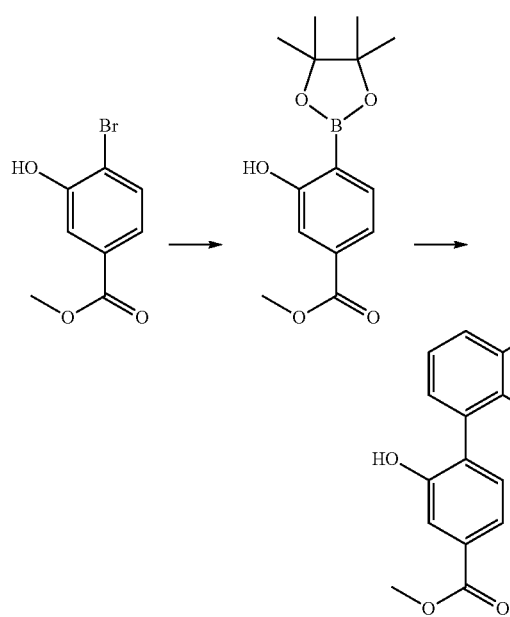

Step 1: Methyl 3-hydroxy-4-(4,4,5,5-tetramethyl-1,3,2-dioxaborolan-2-yl)benzoate Potassium acetate (1.27 g, 13.0 mmol) was added to a solution of methyl 4-bromo-3-hydroxybenzoate (1.0 g, 4.3 mmol) in 1,4-dioxane (20 mL) under N$_2$ followed by addition of 4,4,4',4',5,5,5',5'-octamethyl-2,2'-bi(1,3,2-dioxaborolane) (2.2 g, 8.7 mmol) and 1,1'-bis(diphenylphosphino)ferrocenepalladium(II) dichloride (0.18 g, 0.22 mmol). The mixture was purged with N$_2$ then stirred at about 80° C. for about 3 h. The reaction mixture was cooled to rt and water (50 mL) was added. The mixture was extracted with EtOAc (3×50 mL). The combined organics were dried over Na$_2$SO$_4$, filtered, and concentrated under reduced pressure. The residue was purified via flash chromatography on silica gel (0-10% MeOH/DCM). The appropriate fractions were combined and concentrated under reduced pressure to give the title compound (1.13 g, 94%). $^1$H NMR (400 MHz, CDCl$_3$) δ 7.81 (s, 1H), 7.60 (d, J=8.1 Hz, 1H), 7.50-7.40 (m, 2H), 3.84 (s, 3H), 1.31 (s, 12H).

Step 2: Methyl 3-hydroxy-4-(isoquinolin-8-yl)benzoate

EtOH (100 mL) was added to a mixture of sodium carbonate (2.04 g, 19.2 mmol), Pd(OAc)$_2$ (0.022 g, 0.096 mmol), 8-bromoisoquinoline (2.00 g, 9.61 mmol), methyl 3-hydroxy-4-(4,4,5,5-tetramethyl-1,3,2-dioxaborolan-2-yl)benzoate (2.67 g, 9.61 mmol), and dicyclohexyl(2',6'-dimethoxy-[1,1'-biphenyl]-2-yl)phosphine (0.079 g, 0.19 mmol) under N$_2$. The mixture was degassed with N$_2$ and then heated to about 80° C. for about 16 h. Water (200 mL) was added and the resulting solid was collected by filtration then dried to give the title compound (1.27 g, 47%). MS m/z: 280 (M+H)$^+$.

Preparation C: SM-antiTNFα OregonGreen488 Probe (2',7'-difluoro-3',6'-dihydroxy-N-(2-(2-(2-((4-(isoquinolin-8-yl)-3-(4-(isoquinolin-8-yl) phenethoxy)benzyl)oxy)ethoxy)ethoxy)ethyl)-3-oxo-3H-spiro[isobenzofuran-1,9'-xanthene]-5-carboxamide)

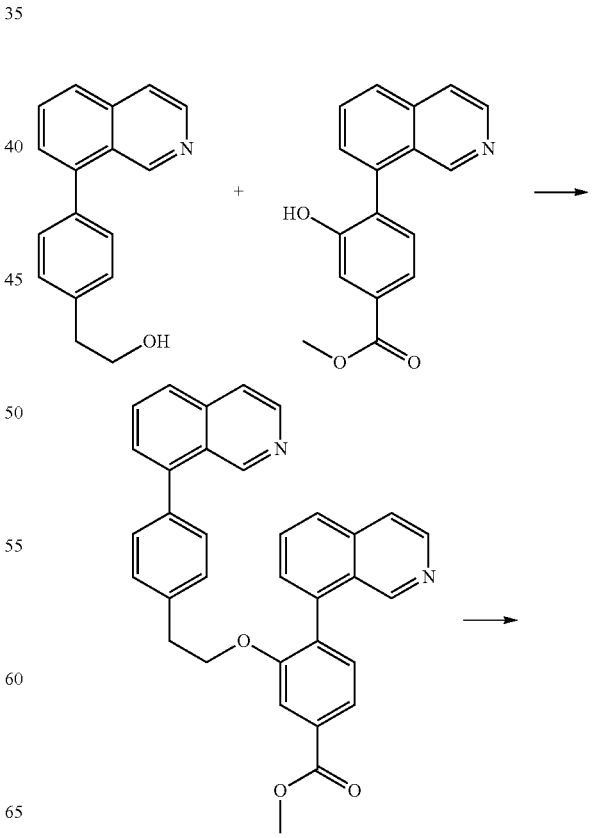

-continued

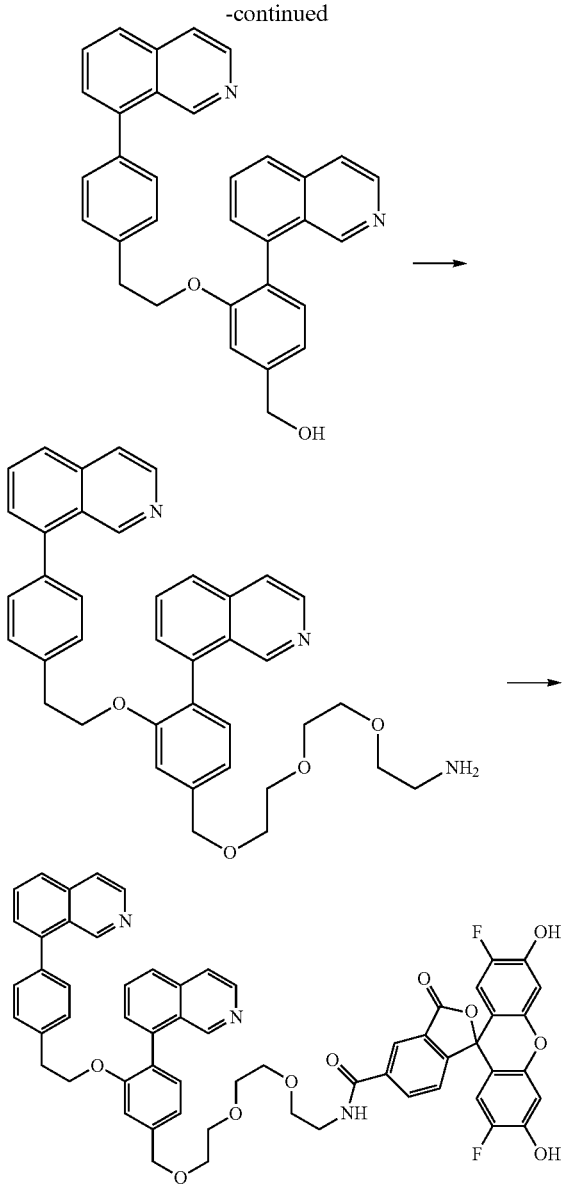

Step 1: Methyl 4-(isoquinolin-8-yl)-3-(4-(isoquinolin-8-yl)phenethoxy)benzoate

Cyanomethylenetributylphosphorane (0.90 mL, 3.4 mmol) was added to a mixture of methyl 3-hydroxy-4-(isoquinolin-8-yl)benzoate (800 mg, 2.86 mmol) (Preparation B), 2-(4-(isoquinolin-8-yl)phenyl)ethanol (714 mg, 2.86 mmol) (Preparation A), and toluene (30 mL). After stirring for about 4 h at about 100° C., the reaction mixture was allowed to cool to rt. Tri-n-butylphosphine (0.71 mL, 2.9 mmol) and (E)-N1,N1,N2,N2-tetramethyldiazene-1,2-dicarboxamide (493 mg, 2.86 mmol) were added respectively. After stirring at rt for about 18 h, the organic volatiles were removed under reduced pressure. The residue was purified via flash chromatography on silica gel (20% acetone/hexanes). The appropriate fractions were collected and concentrated under reduced pressure to give the title compound (1.07 g, 73%). MS m/z: 511 (M+H)$^+$.

Step 2: (4-(Isoquinolin-8-yl)-3-(4-(isoquinolin-8-yl)phenethoxy)phenyl)methanol

Lithium aluminum hydride (1 M solution in THF, 0.4 mL, 0.4 mmol) was added to a solution of methyl 4-(isoquinolin-8-yl)phenethoxy)benzoate (204 mg, 0.400 mmol) and THF (3.6 mL) under $N_2$ at about 0° C. After about 1 h, 10% aqueous sodium potassium tartrate (6 mL) was added. The reaction was allowed to warm to rt. After about 10 min at rt, EtOAc (10 mL) was added. The layers were separated and the aqueous layer was extracted with EtOAc (10 mL). The combined organics were washed with saturated aqueous NaCl (10 mL), dried over $MgSO_4$, filtered and concentrated under reduced pressure. The residue was purified via flash chromatography on silica gel (0-5% McOH/CHCl$_3$). The appropriate fractions were collected and concentrated under reduced pressure to give the title compound (169 mg, 88%). MS m/z: 483 (M+H)$^+$.

Step 3: 2-(2-(2-((4-(Isoquinolin-8-yl)-3-(4-(isoquinolin-8-yl)phenethoxy)benzyl)oxy)ethoxy)ethoxy)ethanamine (4-(Isoquinolin-8-yl)-3-(4-(isoquinolin-8-yl)phenethoxy)phenyl)methanol (31 mg, 0.064 mmol) and 2,2-dimethyl-4-oxo-3,8,11-trioxa-5-azatridecan-13-yl methanesulfonate (32 mg, 0.096 mmol) were combined in DMF (1 mL). Sodium hydride (10 mg, 0.26 mmol) was added in one portion. The reaction was stirred at rt for about 16 h. 50% MeCN/water (1 mL) was added and the resulting mixture was lyophilized to dryness. The residue was diluted with 90% DMSO/water (3 mL) and purified in one injection using RP-HPLC (Waters Deltapak C18 200×25 mm column) with time collection. The appropriate peak was collected and lyophilized. The residue was dissolved in TFA (2 mL) and shaken at rt for about 1 min. The volatiles were evaporated under a stream of dry nitrogen gas. The film was dissolved in 50% MeCN/water (1 mL) and lyophilized to give a trifluoroacetate salt of the title compound (10 mg, 19%). MS m/z: 614 (M+H)$^+$.

Step 4: 2',7'-difluoro-3',6'-dihydroxy-N-(2-(2-(2-((4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1,9'-xanthene]-5-carboxamide 2-(2-(2-((4-(Isoquinolin-8-yl)-3-(4-(isoquinolin-8-yl)phenethoxy)benzyl)oxy)ethoxy)ethoxy)ethanamine (9.38 mg, 9.82 μmol) and 2,5-dioxopyrrolidin-1-yl 2',7'-difluoro-3',6'-dihydroxy-3-oxo-3H-spiro[isobenzofuran-1,9'-xanthene]-5-carboxylate (5 mg, 10 μmol) were combined in 1% DIEA/DMF (1 mL) and shaken at rt. After completion, the reaction mixture was diluted with 90% DMSO/water (2 mL) and purified in one injection using RP-HPLC (Waters Deltapak C18 200×25 mm column) with slope collection. The appropriate peak was collected and lyophilized to give the title compound (4.1 mg, 41%). MS m/z: 1008 (M+H)$^+$.

Analytical Methods

Analytical data was included within the procedures below or in the tables of examples. Unless otherwise stated, all $^1$H NMR data were collected on a Varian 400 MHz Mercury Plus, Inova, or 400-MR instrument and chemical shifts are quoted in parts per million (ppm). LC/MS and HPLC data are referenced to the table of LC/MS and HPLC conditions using the lower case method letter provided in Table A.

TABLE A

LC/MS methods

| Method | Conditions |
|---|---|
| a | LC/MS: The gradient was 5-60% B in 1.5 min then 60-95% B to 2.5 min with a hold at 95% B for 1.2 min (1.3 mL/min flow rate). Mobile phase A was 10 mM $NH_4OAc$, mobile phase B was HPLC grade MeCN. The column used for the chromatography is a 4.6 × 50 mm MAC-MOD Halo C18 column (2.7 μm particles). Detection methods are diode array (DAD) and evaporative light scattering (ELSD) detection as well as positive/negative electrospray ionization. |
| b | LC/MS: The gradient was 5-60% B in 1.50 min then 60-95% B to 2.5 min with a hold at 95% B for 1.2 min (1.3 mL/min flow rate). Mobile phase A was 10 mM $NH_4OAc$, mobile phase B was HPLC grade MeCN. The column used for the chromatography was a 4.6 × 50 mm MAC-MOD Halo C8 column (2.7 μm particles). Detection methods were diode array (DAD) and evaporative light scattering (ELSD) detection as well as positive/negative electrospray ionization. |
| c | LC/MS: The gradient was 5-60% B in 1.6 min then 60-95% B to 2.2 min with a hold at 95% B for 0.1 min (1.0 mL/min flow rate). Mobile phase A was 10 mM $NH_4OAc$, mobile phase B was HPLC grade MeCN. The column used for the chromatography is a 2.1 × 30 mm Waters Cortecs C18 column (1.6 μm particles). Detection methods are diode array (DAD) and evaporative light scattering (ELSD) detection as well as positive/negative electrospray ionization. |
| d | LC/MS: The gradient was 5-60% B in 1.6 min then 60-95% B to 2.2 min with a hold at 95% B for 0.1 min (1.0 mL/min flow rate). Mobile phase A was 10 mM $NH_4OAc$, mobile phase B was HPLC grade MeCN. The column used for the chromatography is a 2.1 × 30 mm Waters Cortecs C18 column (1.6 μm particles). Detection methods are diode array (DAD) and evaporative light scattering (ELSD) detection as well as positive/negative electrospray ionization.) |

TABLE B

Chiral HPLC Methods

| Method | Conditions |
|---|---|
| 1 | 70-95% B in heptane in 20 min then step to 100% B for 6 min (20 mL/min flow rate). Mobile phase B was EtOH (200 proof), mobile phase A was HPLC grade heptane with 0.2% diethylamine modifier added. The column used for the chromatography was a WhelkO1 R,R 21 × 250 mm column from Regis Technologies (5 μm particles). |
| 2 | 65-84% B in heptane over 19 min (20 mL/min flow rate). Mobile phase B was EtOH (200 proof), mobile phase A was HPLC grade heptane with 0.2% diethylamine modifier added. The column used for the chromatography was a WhelkO1 R,R 21 × 250 mm column from Regis Technologies (5 μm particles). |
| 3 | Isocratic 50% B for 25 min (20 mL/min flow rate). Mobile phase B was 1:1 MeOH/EtOH, mobile phase A was HPLC grade heptane with 0.125% diethylamine added. The column used for the chromatography was a Daciel IC 20 × 250 mm column (5 μm particles). |
| 4 | 50-60% B for 20 min (20 mL/min flow rate). Mobile phase B was EtOH (200 proof), mobile phase A was HPLC grade heptane with 0.2% diethylamine added. The column used for the chromatography was a Daciel IC 20 × 250 mm column (5 μm particles). |
| 5 | 65-75% B for 3 min, then 75-85% B for 17 min (20 mL/min flow rate). Mobile phase B was 20% EtOAc/EtOH (200 proof), mobile phase A was HPLC grade heptane with 0.2% diethylamine added. The chromatography used a WhelkO1 R,R 21 × 250 mm column from Regis Technologies (5 μm particles). |
| 6 | 50-62% B in heptane over 25 min (20 mL/min flow rate). Mobile phase B was EtOH (200 proof), mobile phase A was HPLC grade heptane with 0.2% diethylamine modifier added. The column used for the chromatography was a Daciel IC 20 × 250 mm column (5 μm particles). |
| 7 | Gradient separation method wherein mobile phase A was EtOH (200 proof), mobile phase B was HPLC grade heptane with 0.2% DEA. Flow rate was 20 mL/min. Gradient was held at 30% A for 12.4 min, then ramp to 60% A in 0.2 min, hold for 5.4 min. The column used for the chromatography was a YMC SA column (20 × 250 mm). |
| 8 | 5-25% B in heptane for the first 3 min then held at 25% B for the next 24 min then increased to 40% B and held for 8 min then equilibrated back down to 5% B (20 mL/min flow rate). Mobile phase B was EtOH (EtOH is 200 proof), mobile phase A was HPLC grade heptane with 0.2% diethylamine modifier added. The column used for the chromatography was a Daicel ID 20 × 250 mm column from Chiral Technologies (5 μm particles). |
| 9 | 20-65% B in heptane in the first 3 min then 65%-75% B in 30 min then 75%-85% B in the next 10 min then held at 85% B for 5 min, then after equilibrated back down to 20% B (20 mL/min flow rate). Mobile phase B was EtOH (200 proof) with 0.1% diethylamine added, mobile phase A was HPLC grade heptane with 0.2% diethylamine modifier added. The column used for the chromatography was a WhelkO1 R,R 21 × 250 mm column from Regis Technologies (5 μm particles). |
| 10 | 19% B in heptane for 50 min (20 mL/min flow rate). Mobile phase B was a 1:1 mixture of HPLC grade MeOH and EtOH (200 proof), mobile phase A was HPLC grade heptane with 0.2% diethylamine modifier added. The column used for the chromatography was a PCAP-DP, 21 × 250 mm column from Supelco (5 μm particles). |
| 11 | 70-87% B in heptane in 17 min then 87-100% B in 4 min and hold at 100% for 4 min (20 mL/min flow rate). Mobile phase B was EtOH (200 proof), mobile phase A was HPLC grade heptane with 0.2% diethylamine modifier added. The column used for the chromatography was a WhelkO1 RR, 21 × 250 mm column from Regis Technologies (5 μm particles). |

TABLE B-continued

Chiral HPLC Methods

| Method | Conditions |
|---|---|
| 12 | Isocratic 25% B for 32 min (20 mL/min flow rate). Mobile phase B was EtOH (200 proof), mobile phase A was HPLC grade heptane with 0.20% diethylamine added. The column used for the chromatography was a WhelkO1 R,R 21 × 250 mm column from Regis Technologies (5 µm particles) |
| 13 | 65-75% B in heptane for 3 min then 75%-85% B for 20 min., held at 85% for the next 5 min., then stepped gradient down to 75% and held for additional 13 min., then equilibrated back down to 65% B (20 mL/min flow rate). Mobile phase B was MeOH:EtOH 1:1 mixture (EtOH is 200 proof), mobile phase A was HPLC grade heptane with 0.2% diethylamine modifier added. The column used for the chromatography was a WhelkO1 R,R 21 × 250 mm column from Regis Technologies (5 µm particles). |
| 14 | Gradient separation method 50-80% B in heptane over 25 min, hold at 80% for 5 min (20 mL/min flow rate). Mobile phase B was EtOH (200 proof), mobile phase A was HPLC grade heptane with 0.2% diethylamine modifier added. The column used for the chromatography was a WhelkO1 RR column (21 × 250 mm) |
| 15 | Gradient separation method wherein mobile phase A was isopropanol, mobile phase B was HPLC grade heptane with 0.1% DEA. Flow rate was 20 mL/min. Gradient was 5-12% A over 24.0 min. The column used for the chromatography was a Daicel ID column (20 × 250 mm) |
| 16 | Isocratic separation method wherein mobile phase A was HPLC grade isopropanol, mobile phase B was HPLC grade heptane. Flow rate was 20 mL/min. 35% A for 27 min. The column used for the chromatography was a Daicel ID (20 × 250 mm column). |
| 17 | Gradient separation method wherein mobile phase A was isopropanol, mobile phase B was HPLC grade heptane with 0.125% DEA. Flow rate was 20 mL/min. Gradient was 15-30% A over 21.0 min then 30-34% A over 11.0 min. The column used for the chromatography was a Daicel ID column (20 × 250 mm). |
| 18 | Gradient separation method wherein mobile phase A was isopropanol, mobile phase B was HPLC grade heptane with 0.2% DEA. Flow rate was 20 mL/min. Gradient was 15-30% A over 21.0 min then 30-32% A over 9.0 min. The column used for the chromatography was a Daicel ID column (20 × 250 mm). |
| 19 | Gradient separation method used with WhelkO1 RR column (30 × 250 mm) 20% B for 0.5 min then 20-60% B in 0.5 min then hold at 60% B for 17.5 min then 60-85% B over 4.5 min. Note: used 0.2% DEA modifier in heptane (solvent A). No modifier in solvent B (EtOH. Flow was adjusted to achieve measured 30 mL/min effluent at the different compositions in the run. |
| 20 | Isocratic 30% B for 32 min (20 mL/min flow rate). Mobile phase B was EtOH (200 proof) with 0.1% DEA, mobile phase A was HPLC grade heptane with 0.20% DEA added. The column used for the chromatography was a Whelko S,S 20 × 250 mm column from Regis Technologies (5 µm particles) |

TABLE C

Reverse Phase Preparative HPLC methods

| Method | Conditions |
|---|---|
| 1 | Hypersil HS C18 column, 250 mm × 21.2 mm, 8 µm particle size, flow rate 21 mL/min, detection 335 nm, A = 0.05N NH$_4$OAc pH 4.5 buffer, B = MeCN, 10 to 100% B over 25 min |
| 2 | 50 × 150 mm C-18 Atlantis T3 prep column, 30 to 70% MeCN/Water (0.1% TFA), 20 mL/min) over 12 min. |
| 3 | Hypersil HS C18 column, 250 mm × 21.2 mm, 8 µm particle size, flow rate 21 mL/min, detection 254 nm, A = 0.05N NH$_4$OAc pH 4.5 buffer, B = MeCN, 5 to 100% B over 25 min |

TABLE D

SFC methods

| Method | Conditions |
|---|---|
| 1 | 12% EtOH in CO$_2$ (70 mL/min, 130 bar, 35° C.). Cycle time was 3.2 min, with single run time of 10 min. 200 proof EtOH was used with SFC grade CO$_2$. The chromatography used a YMC-SA, 21 × 250 mm column (5 µm particles). |

PREPARATIONS AND EXAMPLES

Starting materials are commercially available, may be prepared by the procedures described herein, by literature procedures, or by procedures that would be well known to one skilled in the art of organic chemistry. Reagent/reactant names given are as named on the commercial bottle or as generated by IUPAC conventions, PerkinElmer ChemDraw® Professional 15.0, CambridgeSoft® ChemDraw Ultra 12.0, CambridgeSoft® Chemistry E-Notebook 11, or AutoNom 2000. None of the specific conditions and reagents noted herein are to be construed as limiting the scope of the disclosure and are provided for illustrative purposes only. Compounds designated as salts (e.g. hydrochloride, trifluoroacetate) may contain more than one molar equivalent of the salt or may contain the acid as an excipient. Compounds of the disclosure where the absolute stereochemistry has been determined by the use of a commercially available enantiomerically pure starting material or a stereochemically defined intermediate or by X-ray diffraction are denoted by an asterisk after the example number. Otherwise the absolute stereochemistry is unknown and assigned randomly as drawn.

Compounds of the disclosure may be prepared using synthetic transformations shown herein. For groups of compounds that have been prepared in a similar fashion, a representative example is given followed by a table of these similarly prepared compounds. It should be appreciated by one skilled in the art that minor modifications to the representative example may be necessary to successfully execute these syntheses. Prepared compounds may be purified by any technique or combination of techniques known to one skilled in the art. Some examples that are not limiting include column chromatography with a solid phase (i.e. silica gel, alumina, etc.) and a solvent (or combination of solvents) that elutes the desired compounds (i.e. hexanes, heptane, EtOAc, DCM, MeOH, EtOH, MeCN, water, etc.); preparatory TLC with a solid phase (i.e. silica gel, alumina etc.) and a solvent (or combination of solvents) that elutes the desired compounds (i.e. hexanes, heptane, EtOAc, DCM, MeOH, EtOH, MeCN, water, etc.); reverse phase HPLC (see Table 1 for some non-limiting conditions); recrystalization from an appropriate solvent (i.e. MeOH, EtOH, IPA, EtOAc, toluene, etc.) or combination of solvents (i.e. EtOAc/heptane, EtOAc/MeOH, etc.); chiral LC with a solid phase and an appropriate solvent (i.e. EtOH/heptane, MeOH/heptane, IPA/heptane, etc. with or without a modifier such as diethylamine, TFA, etc.) to elute the desired compound; chiral SFC with a solid phase and $CO_2$ with an appropriate modifier (i.e. MeOH, EtOH, IPA with or without additional modifier such as diethylamine, TFA, etc.); precipitation from a combination of solvents (i.e. DMF/water, DMSO/DCM, EtOAc/heptane, etc.); trituration with an appropriate solvent (i.e. EtOAc, DCM, MeCN, MeOH, EtOH, IPA, n-PrOH, etc.); extractions by dissolving a compound in a liquid and washing with an appropriately immiscible liquid (i.e. DCM/water, EtOAc/water, DCM/saturated $NaHCO_3$, EtOAc/saturated $NaHCO_3$, DCM/10% aqueous HCl, EtOAc/10% aqueous HCl, etc.); distillation (i.e. simple, fractional, Kugelrohr, etc.); gas chromatography using an appropriate temperature, carrier gas and flow rate; sublimation at an appropriate temperature and pressure; filtration through a media (i.e. Florosil®, alumina, Celite®, silica gel, etc.) with a solvent (i.e. heptane, hexanes, EtOAc, DCM, MeOH, etc.) or combination of solvents; salt formation with solid support (resin based, i.e. ion exchange) or without. Some descriptions of these techniques can be found in the following references, Gordon, A. J. and Ford, R. A. "The Chemist's Companion", 1972; Palleros, D. R. "Experimental Organic Chemistry", 2000; Still, W. C., Kahn, M. and Mitra, A. *J. Org. Chem.* 1978, 43, 2923; Yan, B. "Analysis and Purification Methods in Combinatorial Chemistry" 2003; Harwood, L. M., Moody, C. J. and Percy, J. M. "Experimental Organic Chemistry: Standard and Microscale, 2$^{nd}$ Edition", 1999; Stichlmair, J. G. and Fair, J. R. "Distillation; Principles and Practices" 1998; Beesley T. E. and Scott, R. P. W. "Chiral Chromatography", 1999; Landgrebe, J. A. "Theory and Practice in the Organic Laboratory, 4$^{th}$ Edition", 1993; Skoog, D. A. and Leary, J. J. "Principles of Instrumental Analysis, 4$^{th}$ Edition" 1992; Subramanian, G. "Chiral Separation Techniques 3$^{rd}$ Edition" 2007; Kazakevich, Y. and Lobrutto, R. "HPLC for Pharmaceutical Scientists" 2007.

Preparation #1: 6-Bromo-3-(2-(difluoromethoxy) phenyl)-2,3-dihydropyrazolo[1,2-a]indazol-9(1H)-one

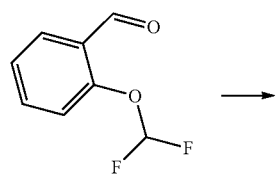

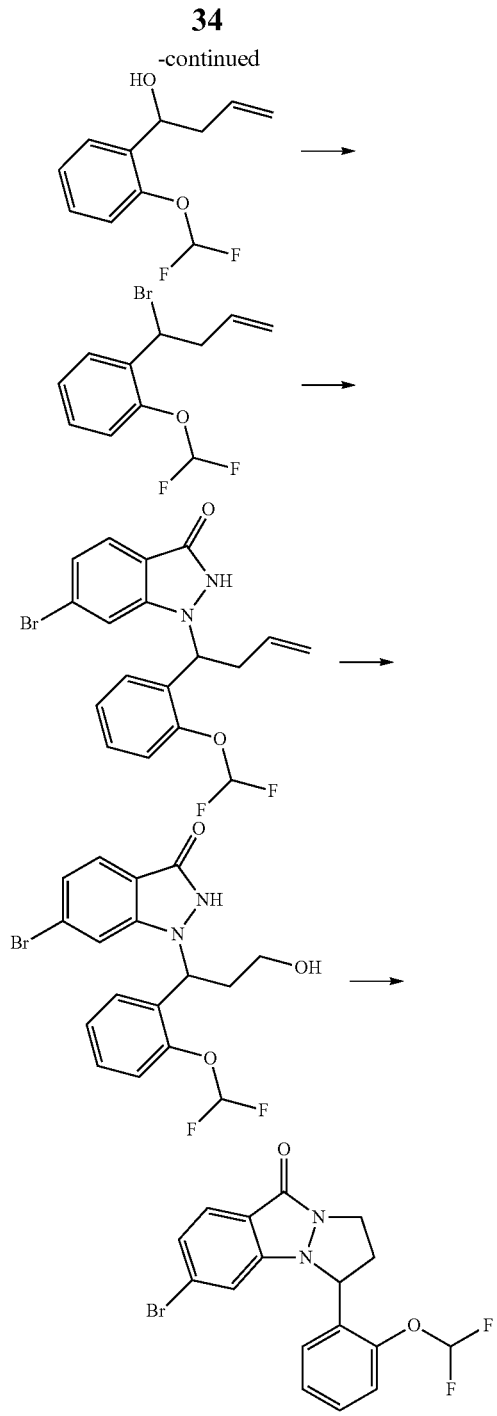

Step 1: 1-(2-(Difluoromethoxy)phenyl)but-3-en-1-ol 2-(Difluoromethoxy)benzaldehyde (20.1 g, 117 mmol) was dissolved in dry THF (350 mL) under $N_2$. The reaction mixture was cooled to about −78° C. and then allylmagnesium bromide (1 M solution in $Et_2O$) (152 mL, 152 mmol) was added dropwise, keeping the internal temperature below about −65° C. The mixture was stirred at about −65° C. for about 1 h then allowed to warm to about 5° C. over about 1 h. The mixture was cooled to about 0° C. then quenched with saturated aqueous ammonium chloride solution (200 mL). The mixture was extracted with EtOAc (2×200 mL) then the combined organics were dried over $MgSO_4$, filtered and concentrated under reduced pressure to give the title compound (24.05 g, 96%); $^1$H NMR (400 MHz, DMSO) δ 7.53 (dd, J=7.5, 1.7 Hz, 1H), 7.31-7.19 (m, 2H), 7.17 (t, J=76 Hz, 1H), 7.10 (d, J=8.0 Hz, 1H), 5.84-5.71 (m, 1H), 5.26 (d, J=4.7 Hz, 1H), 5.01-4.85 (m, 3H), 2.41-2.25 (m, 2H).

Step 2: 1-(1-Bromobut-3-en-1-yl)-2-(difluoromethoxy)benzene 1-(2-(Difluoromethoxy)phenyl)but-3-en-1-ol (16.43 g, 77 mmol) was stirred in DCM (384 mL) then PBr$_3$ (18.09 mL, 192 mmol) was added and the mixture stirred at rt for about 2 h. The mixture was cooled to about 0° C. in an ice bath then aqueous saturated sodium bicarbonate was added slowly until a neutral pH was achieved. The mixture was stirred an additional 30 min then the layers were separated and the organic solution was dried over MgSO$_4$, filtered and concentrated under reduced pressure. The residue was purified via flash chromatography on silica gel (0-15% EtOAc/heptane) to give the title compound (15.49 g, 73%); $^1$H NMR (400 MHz, DMSO) δ 7.68 (dd, J=7.8, 1.7 Hz, 1H), 7.43-7.37 (m, 1H), 7.32-7.27 (m, 1H), 7.26 (t, J=75 Hz, 1H), 7.20-7.16 (m, 1H), 5.78-5.66 (m, 1H), 5.43-5.37 (m, 1H), 5.18-5.05 (m, 2H), 3.10-2.93 (m, 2H).

Step 3: 6-Bromo-1-(1-(2-(difluoromethoxy)phenyl)but-3-en-1-yl)-1H-indazol-3(2H)-one 6-Bromo-1H-indazol-3(2H)-one (7.44 g, 34.9 mmol) in DMF (50 mL) was treated with powdered potassium carbonate (5.31 g, 38.4 mmol) then the mixture was warmed to about 50° C. 1-(1-Bromobut-3-en-1-yl)-2-(difluoromethoxy)benzene (15.5 g, 55.9 mmol) in DMF (80 mL) was added over about 45 min. After about 2 h, the mixture was added to ice water (200 mL) with stirring. The solids were collected by filtration, rinsed with DCM (20 mL) and dried to constant weight in a vacuum oven to give the title compound. (1.05 g, 7%); LC/MS (Table A, Method b) R$_t$=2.54 min; MS m/z: 409, 411 (M+H)$^+$.

Step 4: 6-Bromo-1-(1-(2-(difluoromethoxy)phenyl)-3-hydroxypropyl)-1H-Indazol-3(2H)-one A suspension of 6-bromo-1-(1-(2-(difluoromethoxy)phenyl)but-3-en-1-yl)-1H-indazol-3(2H)-one (5.44 g, 13.3 mmol) and 4-methylmorpholine 4-oxide (4.67 g, 39.9 mmol) in THF (66 mL) was cooled to about 0° C. in an ice/water bath for about 5 min. The mixture was treated with osmium (VIII) oxide (4 wt % in water) (4.23 g, 0.665 mmol). The mixture was warmed to rt for about 2.5 h then a 10% aqueous sodium bisulfite solution (60 mL) was added. The mixture was stirred at rt for about 1 h. The mixture was extracted with EtOAc (3×40 mL), filtering the mixture to remove emulsive material. The combined organics were dried over MgSO$_4$, filtered then the filtrate was concentrated under reduced pressure to give 6-bromo-1-(1-(2-(difluoromethoxy)phenyl)-3,4-dihydroxybutyl)-1H-indazol-3(2H)-one (5.89 g, 100%). A solution of 6-bromo-1-(1-(2-(difluoromethoxy)phenyl)-3,4-dihydroxybutyl)-1H-indazol-3(2H)-one (5.89 g, 13.3 mmol) in THF (100 mL) and water (25 mL) was treated at rt with sodium periodate (4.26 g, 19.9 mmol). After about 1 h, the reaction mixture was partitioned between water (30 mL) and DCM (100 mL). After separating the layers, the aqueous phase was extracted with additional DCM (100 mL). The combined organic phases were washed with saturated aqueous NaCl (70 mL), dried over MgSO$_4$ and filtered. The filtrate was concentrated under reduced pressure to give 3-(6-bromo-3-oxo-2,3-dihydro-1H-indazol-1-yl)-3-(2-(difluoromethoxy)phenyl)propanal (5.46 g, 100%). A suspension of 3-(6-bromo-3-oxo-2,3-dihydro-1H-indazol-1-yl)-3-(2-(difluoromethoxy)phenyl)propanal (4.80 g, 11.7 mmol) in MeOH (100 mL) was cooled to about 0° C. then treated with NaBH$_4$ (0.442 g, 11.67 mmol). After about 30 min, additional NaBH$_4$ (0.050 g, 1.32 mmol) was added. The mixture was stirred for about 15 min then the reaction mixture was partitioned between EtOAc (100 mL) and saturated aqueous NH$_4$Cl (50 mL). After separating the layers the aqueous phase was extracted with EtOAc (2×40 mL). The combined organic phases were washed with saturated aqueous NaCl (100 mL), dried over MgSO$_4$, filtered, and concentrated under reduced pressure. The material was purified via flash chromatography on silica gel (0-100% EtOAc/DCM). The appropriate fractions were concentrated to give the title compound (3.1 g, 64%); LC/MS (Table A, Method b) R$_t$=2.09 min; MS m/z: 413, 415 (M+H)$^+$.

Step 5: 6-Bromo-3-(2-(difluoromethoxy)phenyl)-2,3-dihydropyrazolo[1,2-a]indazol-9(1H)-one A flask was charged with 6-bromo-1-(1-(2-(difluoromethoxy)phenyl)-3-hydroxypropyl)-1H-indazol-3(2H)-one (0.830 g, 2.009 mmol) in DCM (9 mL). 2,6-Dimethylpyridine (0.702 mL, 6.03 mmol) and XtalFluor-E® (0.736 g, 3.21 mmol) were each added sequentially in one portion. The resulting solution was allowed to stir at rt for about 45 min. The mixture was quenched with saturated aqueous sodium bicarbonate (10 mL) then extracted with DCM (2×20 mL). The organic solution was dried over MgSO$_4$, filtered and the filtrate was concentrated under reduced pressure. The residue was purified via flash chromatography on silica gel (0-100% EtOAc/DCM). The appropriate fractions were concentrated to give the title compound (0.596 g, 75%); LC/MS (Table A, Method b) R$_t$=2.20 min; MS m/z: 395, 397 (M+H)$^+$.

Preparation #2: (S)-6-Bromo-3-(2-(difluoromethoxy)phenyl)-2,3-dihydropyrazolo[1,2-a]indazol-9(1H)-one

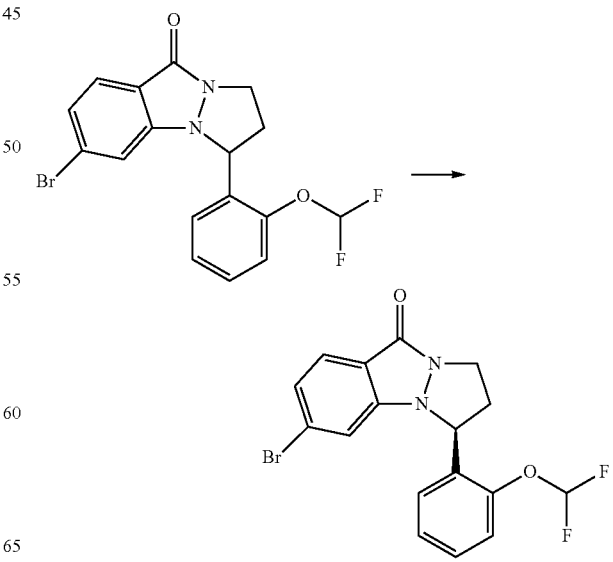

6-Bromo-3-(2-(difluoromethoxy)phenyl)-2,3-dihydropyrazolo[1,2-a]indazol-9(1H)-one (0.650 g, 1.645 mmol) (Preparation t#1) was submitted for chiral purification (Table B, Method 12). Fractions from the first eluting component were combined and concentrated under reduced pressure then taken into water, frozen and lyophilized to give the title compound (0.255 g, 39%) with negative (−) optical rotation. LC/MS (Table A, Method a) $R_t$=2.19 min; MS m/z: 397, 395 (M+H)$^+$.

Preparation #3: (R)-6-Bromo-3-(2-(difluoromethoxy)phenyl)-2,3-dihydropyrazolo[1,2-a]indazol-9(1H)-one

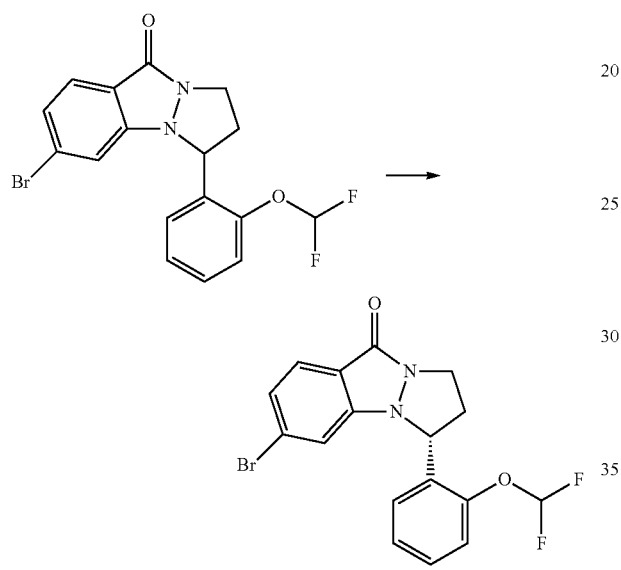

6-Bromo-3-(2-(difluoromethoxy)phenyl)-2,3-dihydropyrazolo[1,2-a]indazol-9(1H)-one (0.650 g, 1.645 mmol) (Preparation #1) was submitted for chiral purification (Table B, Method 12). Fractions from the second eluting component were combined and concentrated under reduced pressure then taken into water, frozen and lyophilized to give the title compound (0.250 g, 39%) with positive (+) optical rotation. LC/MS (Table A, Method a) $R_t$=2.19 min; MS m/z: 397, 395 (M+H)$^+$.

Preparation #4: (R)-2-(2-(Methoxymethyl)pyrrolidin-1-yl)-5-(4,4,5,5-tetramethyl-1,3,2-dioxaborolan-2-yl)pyrimidine

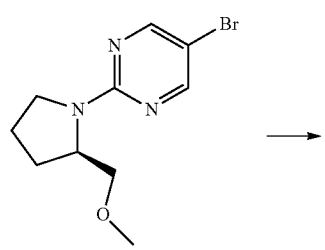

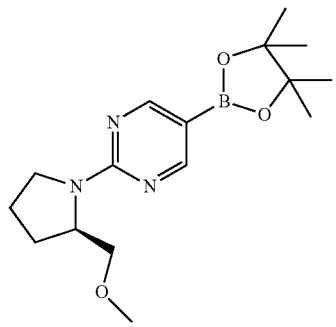

(R)-5-Bromo-2-(2-(methoxymethyl)pyrrolidin-1-yl)pyrimidine (0.220 g, 0.808 mmol) (Preparation #10) was dissolved in DMF (2 mL) then degassed and flushed with $N_2$. Potassium acetate (0.167 g, 1.70 mmol) and 4,4,4',4',5,5,5',5'-octamethyl-2,2'-bi(1,3,2-dioxaborolane) (0.308 g, 1.21 mmol) were added followed by an additional degas and flush with $N_2$. PdCl$_2$(dppf) (0.041 g, 0.057 mmol) was then added, degassed then heated under $N_2$ to 85° C. for about 1 h. The mixture was cooled to rt, filtered through Celite®, then concentrated under reduced pressure. The residue was purified via flash chromatography on silica gel (0-50% EtOAc/DCM) to give the title compound. (0.099 g, 38%); LC/MS (Table A, Method b) $R_t$=2.43 min; MS m/z: 320 (M+H)$^+$.

Preparation #5: (R)—N-(Tetrahydrofuran-3-yl)-5-(4,4,5,5-tetramethyl-1,3,2-dioxaborolan-2-yl)pyrimidin-2-amine

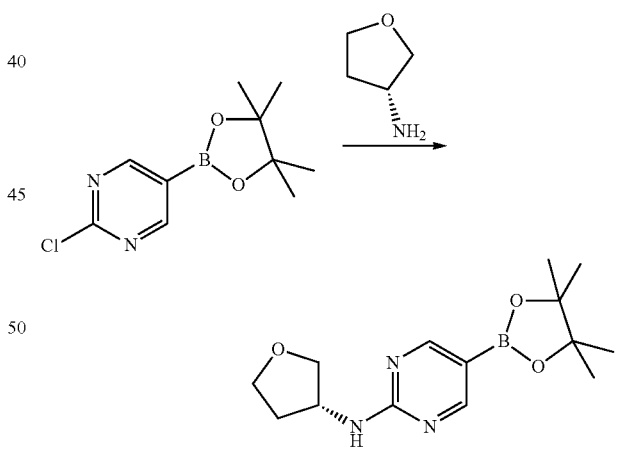

2-Chloro-5-(4,4,5,5-tetramethyl-1,3,2-dioxaborolan-2-yl)pyrimidine (0.331 g, 1.376 mmol), (R)-tetrahydrofuran-3-amine (0.132 g, 1.514 mmol), and TEA (0.211 mL, 1.514 mmol) were mixed in EtOH (3 mL) at 80° C. for about 1 h. The mixture was cooled to rt under $N_2$. The mixture was concentrated under reduced pressure and then purified via flash chromatography on silica gel (10-100% EtOAc/DCM) to give the title compound (0.296 g, 74%); LC/MS (Table A, Method b) $R_t$=1.89 min; MS m/z: 292 (M+H)$^+$.

Preparation #6: (R)-(2-(2-(Hydroxymethyl)morpholino)pyrimidin-5-yl)boronic acid

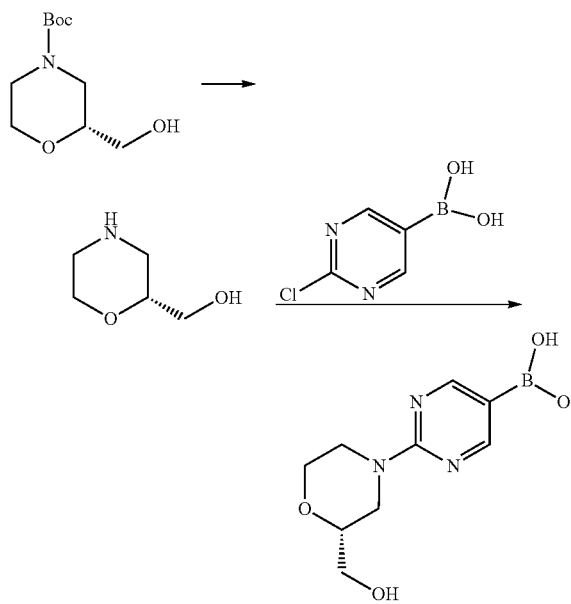

Step 1: (R)-Morpholin-2-ylmethanol TFA Salt (R)-tert-Butyl 2-(hydroxymethyl)morpholine-4-carboxylate (0.200 g, 0.921 mmol) was dissolved in DCM (3 mL) followed by the addition of TFA (0.355 mL, 4.60 mmol). The mixture was stirred at rt for about 17 h. Additional TFA (0.355 mL, 4.60 mmol) was added and the mixture was stirred an additional 17 h. The mixture was concentrated under reduced pressure to furnish the title compound (0.108 g, 100%); $^1$H NMR (400 MHz, CDCl$_3$) δ 9.47 (br, 1H), 7.41 (br, 1H), 4.52-4.45 (m, 1H), 4.41-4.35 (m, 1H), 4.21-4.08 (m, 2H), 4.02-3.93 (m, 1H), 3.45-3.30 (m, 2H), 3.21-3.10 (m, 1H), 3.07-2.96 (m, 1H).

Step 2: (R)-(2-(2-(Hydroxymethyl)morpholino)pyrimidin-5-yl)boronic acid (2-Chloropyrimidin-5-yl)boronic acid (0.122 g, 0.768 mmol), EtOH (2 mL), TEA (0.13 mL, 0.92 mmol) and (R)-morpholin-2-ylmethanol TFA salt (0.108 g, 0.922 mmol) were heated to about 80° C. for about 1 h. The reaction mixture was cooled to rt and then concentrated under reduced pressure. The residue was purified via flash chromatography on silica gel (50-100% EtOAc/DCM then 0-6% MeOH/DCM). The appropriate fractions were concentrated to give the title compound (0.139 g, 76%); LC/MS (Table A, Method b) R$_t$=0.91 min; MS m/z: 240 (M+H)$^+$.

Preparation #7: 7-(5-Bromopyrimidin-2-yl)hexahydroimidazo[1,5-a]pyrazin-3(2H)-one

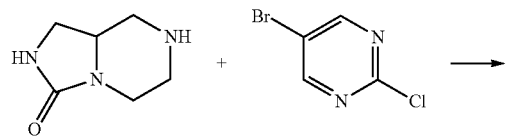 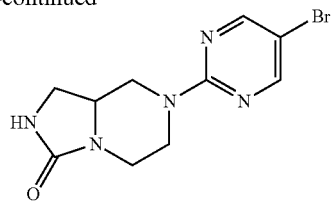

A mixture of hexahydroimidazo[1,5-a]pyrazin-3(2H)-one hydrochloride (0.441 g, 2.48 mmol), 5-bromo-2-chloropyrimidine (0.542 g, 2.80 mmol), TEA (1.20 mL, 8.61 mmol), and EtOH (20 mL) was warmed to about 78° C. After about 4 h, the solution was allowed to cool to rt. After stirring about 20 h, the volatiles were removed under reduced pressure. The residue was partitioned between 5% MeOH/DCM (50 mL) and water (25 mL). The aqueous layer was extracted with 5% MeOH/DCM (2×25 mL). The combined organics were dried over Na$_2$SO$_4$, filtered, and concentrated under reduced pressure. The residue was purified via flash chromatography on silica gel (0-5% McOH/DCM) to give the title compound (0.714 g, 96%); LC/MS (Table A, Method b) R$_t$=1.61 min; MS m/z: 298, 300 (M+H)$^+$.

Preparation #8: (S)-7-(5-Bromopyrimidin-2-yl)hexahydroimidazo[1,5-a]pyrazin-3(2H)-one

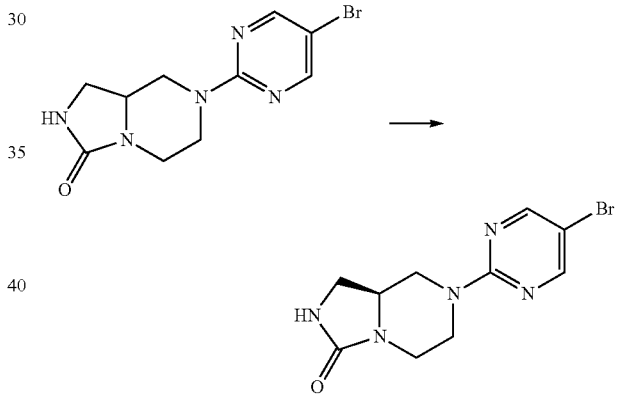

7-(5-Bromopyrimidin-2-yl)hexahydroimidazo[1,5-a]pyrazin-3(2H)-one (0.714 g, 2.40 mmol) (Preparation #7) was submitted for chiral purification (Table B, Method 7). Fractions from the first eluting component were combined and concentrated under reduced pressure then dried to give the title compound (0.320 g, 43%) with positive (+) optical rotation. LC/MS (Table A, Method b) R$_t$=1.61 min; MS m/z: 298, 300 (M+H)$^+$.

Preparation #9: (R)-7-(5-Bromopyrimidin-2-yl)hexahydroimidazo[1,5-a]pyrazin-3(2H)-one

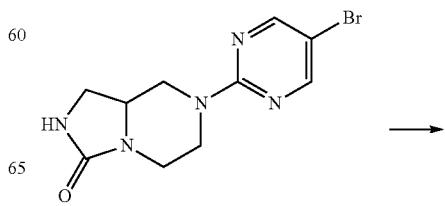

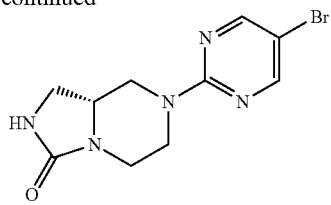

7-(5-Bromopyrimidin-2-yl)hexahydroimidazo[1,5-a]pyrazin-3(2H)-one (0.714 g, 2.40 mmol) (Preparation #7) was submitted for chiral purification (Table B, Method 7). Fractions from the second eluting component were combined and concentrated under reduced pressure then dried to give the title compound (0.335 g, 44%) with negative (−) optical rotation. LC/MS (Table A, Method b) $R_t$=1.61 min; MS m/z: 298, 300 (M+H)$^+$.

Preparation #10: (R)-5-Bromo-2-(2-(methoxymethyl)pyrrolidin-1-yl)pyrimidine

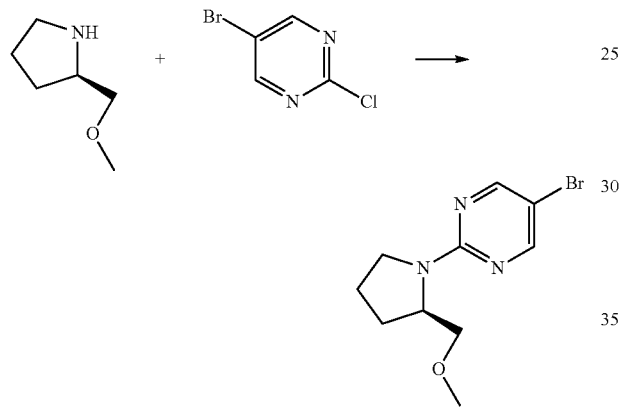

NMP (10.0 mL), DIEA (5.00 mL, 28.6 mmol), and (R)-2-(methoxymethyl)pyrrolidine (2.00 mL, 16.2 mmol) were added respectively to 5-bromo-2-chloropyrimidine (2.00 g, 10.3 mmol). After about 4 h at about 120° C., the solution was allowed to cool to rt and the volatiles were removed under reduced pressure at about 90° C. Water (20 mL), saturated aqueous NH$_4$Cl (20 mL) and EtOAc (50 mL) were added. The layers were separated and the organics were washed with water (50 mL). The aqueous layers were extracted with EtOAc (25 mL). The combined organics were dried over Na$_2$SO$_4$, filtered and concentrated under reduced pressure. The residue was purified via flash chromatography on silica gel (0-20% EtOAc/heptane) to give the title compound (2.66 g, 95%); LC/MS (Table A, Method b) $R_t$=2.27 min; MS m/z: 272, 274 (M+H)$^+$.

Preparation #11: 4-(((5-Bromopyrimidin-2-yl)amino)methyl)pyrrolidin-2-one

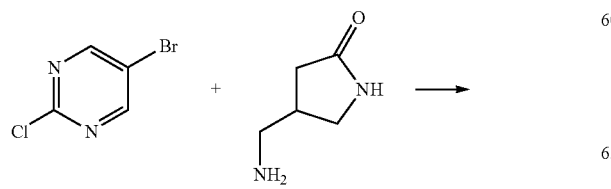

The title compound was synthesized using methods similar to Preparation #10 from 4-(aminomethyl)pyrrolidin-2-one and 5-bromo-2-chloropyrimidine; LC/MS (Table A, Method b) $R_t$=1.36 min; MS m/z: 271, 273 (M+H)$^+$.

Preparation #12: (S)-4-(((5-Bromopyrimidin-2-yl)amino)methyl)pyrrolidin-2-one

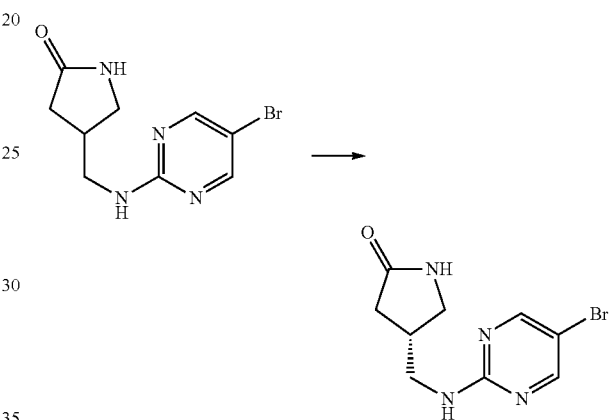

4-(((5-Bromopyrimidin-2-yl)amino)methyl)pyrrolidin-2-one (0.603 g, 2.22 mmol) (Preparation #11) was submitted for chiral purification (Table B, Method 8). Fractions from the first eluting component were combined and concentrated under reduced pressure then dried in a vacuum oven at about 65° C. for about 24 h to give the title compound (0.228 g, 38%) LC/MS (Table A, Method b) $R_t$=1.34 min; MS m/z: 271, 273 (M+H)$^+$.

Preparation #13: (R)-4-(((5-Bromopyrimidin-2-yl)amino)methyl)pyrrolidin-2-one

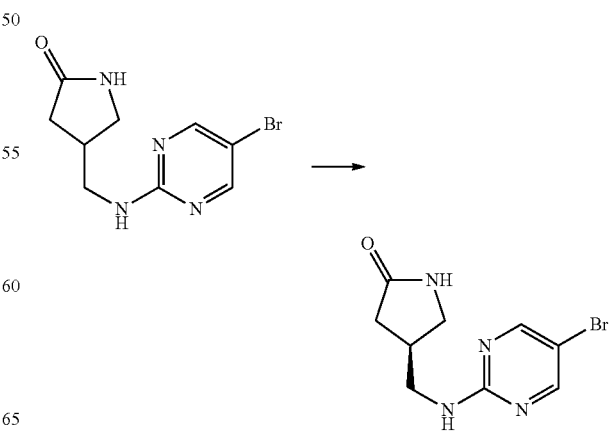

4-(((5-Bromopyrimidin-2-yl)amino)methyl)pyrrolidin-2-one (0.603 g, 2.22 mmol) (Preparation #11) was submitted for chiral purification (Table B, Method 8). Fractions from the second eluting component were combined and concentrated under reduced pressure then dried in a vacuum oven at about 65° C. for about 24 h to give the title compound (0.237 g, 39%) LC/MS (Table A, Method b) $R_t$=1.34 min; MS m/z: 271, 273 (M+H)$^+$.

Preparation #14: 6-(2-(4-Acetylpiperazin-1-yl)pyrimidin-5-yl)-3-(2-(difluoromethoxy)phenyl)-2,3-dihydropyrazolo[1,2-a]indazol-9(1H)-one

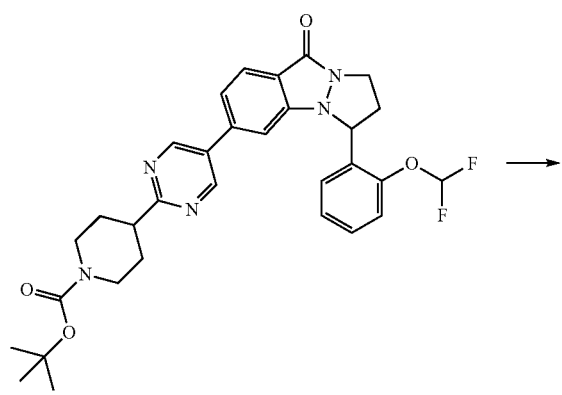

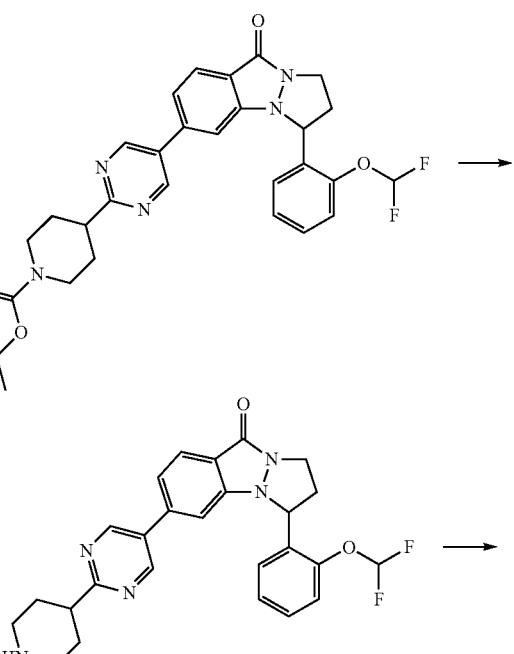

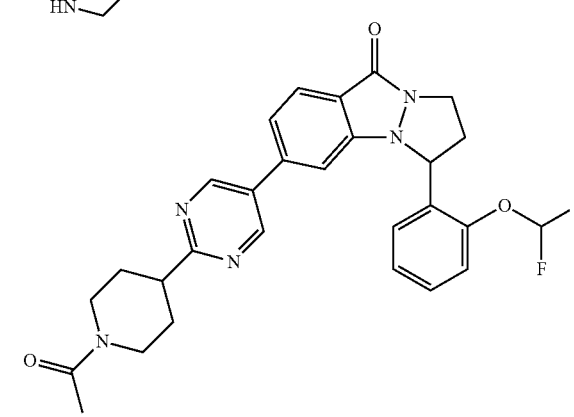

Step 1: 3-(2-(Difluoromethoxy)phenyl)-6-(2-(piperazin-1-yl)pyrimidin-5-yl)-2,3-dihydropyrazolo[1,2-a]indazol-9(1H)-one hydrochloride To a solution of tert-butyl 4-(5-(3-(2-(difluoromethoxy)phenyl)-9-oxo-1,2,3,9-tetrahydropyrazolo[1,2-a]indazol-6-yl)pyrimidin-2-yl)piperazine-1-carboxylate (0.135 g, 0.196 mmol) (synthesized from tert-butyl 4-(5-(4,4,5,5-tetramethyl-1,3,2-dioxaborolan-2-yl)pyrimidin-2-yl)piperazine-1-carboxylate and 6-bromo-3-(2-(difluoromethoxy)phenyl)-2,3-dihydropyrazolo[1,2-a]indazol-9(1H)-one (Preparation #1) in a manner similar to Example #1, step 1) in 1,4-dioxane (2.8 mL) was added 4 M HCl in 1,4-dioxane (1.9 mL, 7.60 mmol) dropwise and stirred at ambient temperature for about 5 h. The solvent was removed under reduced pressure. The residue was dissolved in EtOAc (15 mL) and then concentrated under reduced pressure to give the title compound (0.101 g, 100%). LC/MS (Table A, Method b) $R_t$=1.47 min; MS m/z: 479 (M+H)$^+$.

Step 2: 6-(2-(4-Acetylpiperazin-1-yl)pyrimidin-5-yl)-3-(2-(difluoromethoxy)phenyl)-2,3-dihydropyrazolo[1,2-a]indazol-9(1H)-one To a mixture of 3-(2-(difluoromethoxy)phenyl)-6-(2-(piperazin-1-yl)pyrimidin-5-yl)-2,3-dihydropyrazolo[1,2-a]indazol-9(1H)-one hydrochloride (0.101 g, 0.196 mmol) in DCM (2.0 mL) was added triethylamine (0.11 mL, 0.789 mmol) and acetyl chloride (0.015 mL, 0.211 mmol). The reaction was stirred at ambient temperature for about 2 h then acetyl chloride (0.005 mL, 0.070 mmol) was added. The mixture was stirred for about 5 min then saturated aqueous NaHCO$_3$ (10 mL) and DCM (8 mL) were added and the layers were separated. The organic layer was dried over MgSO$_4$, filtered and concentrated under reduced pressure. The material was purified via flash chromatography on silica gel (0-10% MeOH/DCM). The appropriate fractions were combined and concentrated under reduced pressure to give the title compound (0.095 g, 93%). LC/MS (Table A, Method b) $R_t$=1.89 min; MS m/z: 521 (M+H)$^+$.

Preparation #15: 3-Bromo-6-(2-(difluoromethoxy)phenyl)-8,9-dihydro-6H-pyridazino[1,2-a]indazol-11(7H)-one

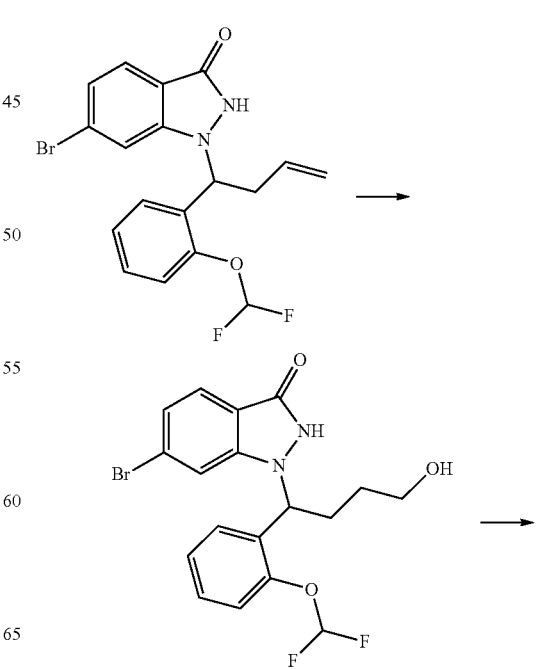

45
-continued

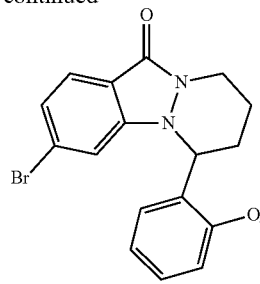

Step 1: 6-Bromo-1-(1-(2-(difluoromethoxy)phenyl)-4-hydroxybutyl)-1H-indazol-3(2H)-one A solution of 6-bromo-1-(1-(2-(difluoromethoxy)phenyl)but-3-en-1-yl)-1H-indazol-3(2H)-one (1.33 g, 3.25 mmol) (Preparation #1, Step 3) in THF (32.5 mL) was treated at rt with 9-BBN dimer (0.787 g, 3.25 mmol) and the resulting suspension was stirred for about 10 min. The reaction mixture was then heated at about 55° C. After about 1 h, additional 9-BBN dimer (0.35 g, 1.4 mmol) was added, and again after about 1 h (0.30 g, 1.2 mmol). About 5 min after the final addition, the reaction was cooled in an ice bath. EtOH (2 mL) was added, followed by careful addition of 2.5 M aqueous NaOH (2 mL) and 30% aqueous $H_2O_2$ (2 mL). The mixture was partitioned between EtOAc (75 mL) and water (50 mL). After separating the layers, the aqueous phase was extracted with EtOAc (3×50 mL). The combined organic phases were washed with saturated aqueous NaCl (125 mL), dried over $Na_2SO_4$, filtered, and concentrated under reduced pressure. The material was purified via flash chromatography on silica gel (0-10% EtOAc/heptane) to give the title compound (1.26 g, 90%); LC/MS (Table A, Method b) $R_t$=2.13 min; MS m/z: 427 and 429 (M+H)$^+$.

Step 2: 3-Bromo-6-(2-(difluoromethoxy)phenyl)-8,9-dihydro-6H-pyridazino[1,2-a]indazol-11(7H)-one To a stirred solution of 6-bromo-1-(1-(2-(difluoromethoxy)phenyl)-4-hydroxybutyl)-1H-indazol-3(2H)-one (0.85 g, 2.0 mmol) in DCM (20 mL) was added XtalFluor-E® (0.683 g, 2.98 mmol). The resulting solution was stirred at about rt for about 45 min. The reaction mixture was quenched by addition of saturated aqueous $NaHCO_3$ (20 mL). After separating the layers, the aqueous phase was extracted with DCM (20 mL). The combined organics were washed with saturated aqueous NaCl (25 mL), dried over $Na_2SO_4$, filtered, and concentrated under reduced pressure. The material was purified via flash chromatography on silica (0-50% EtOAc/heptane) to give the title compound (0.353 g, 43%); LC/MS (Table A, Method b) $R_t$=2.33 min; MS m/z: 409, 411 (M+H)$^+$.

46

Preparation #16: 6-(2-(Difluoromethoxy)phenyl)-3-(2-thiomorpholinopyrimidin-5-yl)-8,9-dihydro-6H-pyridazino[1,2-a]indazol-11(7H)-one

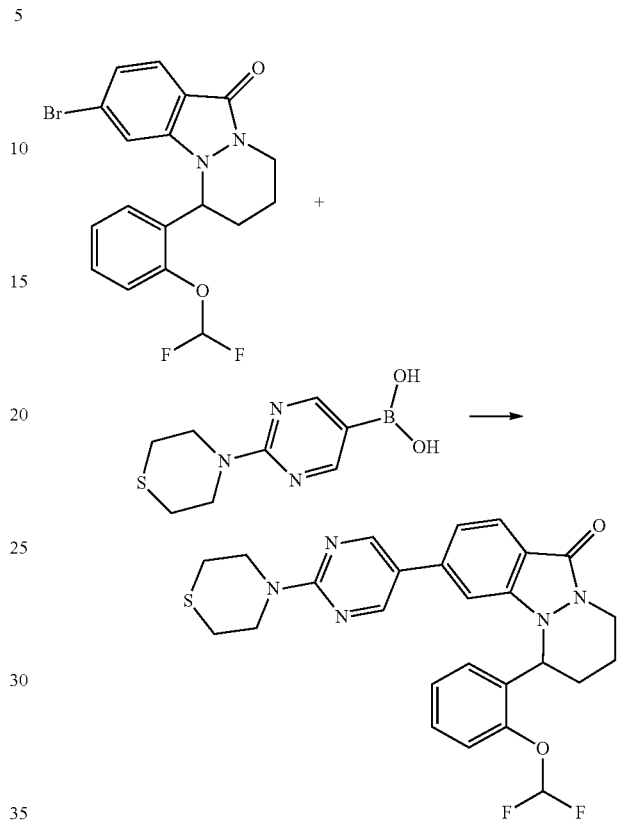

A mixture of 3-bromo-6-(2-(difluoromethoxy)phenyl)-8,9-dihydro-6H-pyridazino[1,2-a]indazol-11(7H)-one (0.085 g, 0.21 mmol) (Preparation #15), (2-thiomorpholinopyrimidin-5-yl)boronic acid (0.118 g, 0.415 mmol) (synthesized from thiomorpholine and 2-chloropyrimidine-5-boronic acid using methods similar to Preparation #6, step 2), Pd(Ph$_3$P)$_4$ (0.024 g, 0.021 mmol), and cesium carbonate (0.203 g, 0.623 mmol) in 1,4-dioxane (1 mL)/water (0.25 mL) was heated at about reflux for about 16 h. After cooling to rt the reaction mixture was partitioned between EtOAc (5 mL) and saturated aqueous NaCl (1 mL). The layers were separated then the organic phase was dried over $Na_2SO_4$, filtered, and concentrated under reduced pressure. The residue was purified via flash chromatography on silica gel (0-5% MeOH/DCM) to give the title compound (0.118 g, 100%); LC/MS (Table A, Method b) $R_t$=2.49 min; MS m/z: 510 (M+H)$^+$.

Preparation #17: 6-Bromo-3-(2-methoxyphenyl)-2,3-dihydropyrazolo[1,2-a]indazol-9(1H)-one

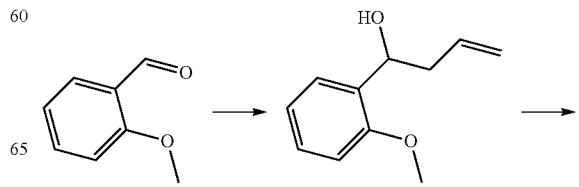

47
-continued

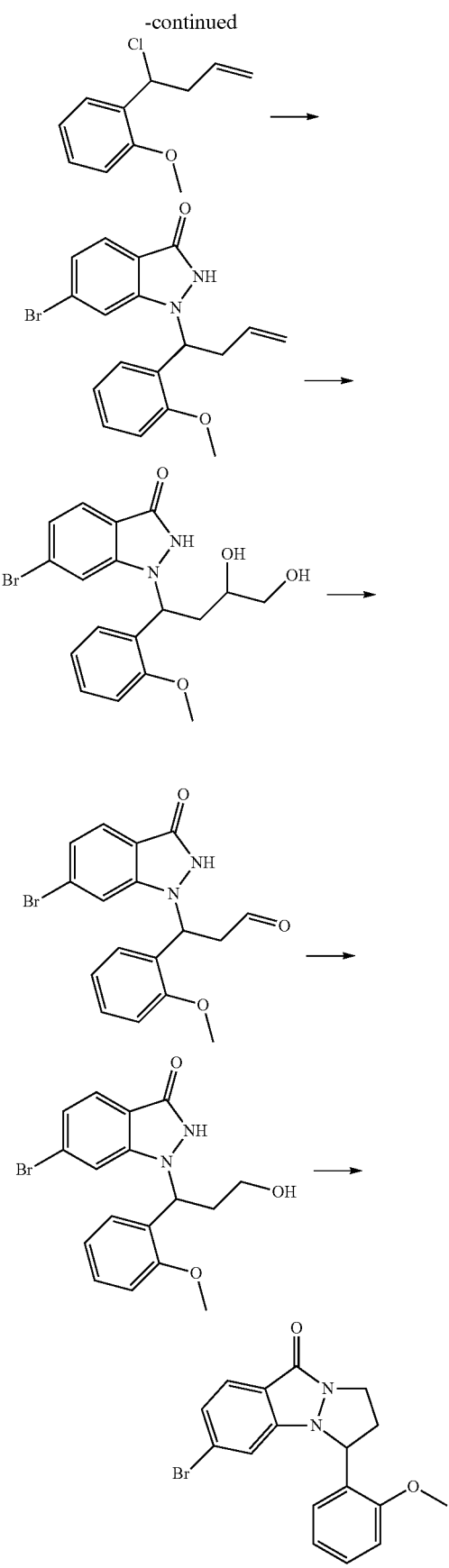

48

Step 1: 1-(2-Methoxyphenyl)but-3-en-1-ol

A solution of 2-methoxybenzaldehyde (11 g, 81 mmol) in THF (300 mL) was cooled to below −70° C. in a dry ice bath. Allylmagnesium bromide (1 M in $Et_2O$, 121 mL, 121 mmol) was added dropwise while keeping the temperature at or below −70° C. Once the addition was complete (about 2 h) the cooling bath was removed and the reaction mixture was allowed to warm to rt. The reaction mixture was then cooled to about 0° C. in an ice/water bath then saturated aqueous $NH_4Cl$ (125 mL) was slowly added. Water (25 mL) was added and the layers were separated. The aqueous phase was extracted with EtOAc (125 mL) and the combined organics were washed with saturated aqueous NaCl (250 mL), dried over $Na_2SO_4$, filtered, and concentrated under reduced pressure to give the title compound (14.4 g, 100%); $^1$H NMR (400 MHz, Chloroform-d) δ 7.39-7.30 (m, 1H), 7.29-7.18 (m, 1H), 7.03-6.92 (m, 1H), 6.91-6.84 (m, 1H), 5.97-5.74 (m, 1H), 5.23-5.04 (m, 2H), 5.04-4.91 (m, 1H), 3.85 (s, 3H), 2.69-2.34 (m, 2H).

Step 2: 1-(1-Chlorobut-3-en-1-yl)-2-methoxybenzene

A flask containing cyanuric chloride (7.76 g, 42.1 mmol) was cooled in an ice water bath after which DMF (22 mL) was added, and the resulting suspension was stirred for about 30 min. 1-(2-Methoxyphenyl)but-3-en-1-ol (5.0 g, 28 mmol) in DCM (110 mL) was added and the ice bath was removed. After stirring for 1 h, diethyl ether (250 mL) was added and the resulting suspension was stirred at rt overnight. The suspension was filtered to remove precipitated solids, and the filtrate was then washed with saturated aqueous $Na_2CO_3$ (2×100 mL). The organic phase was washed with saturated aqueous NaCl (150 mL), dried over $Na_2SO_4$, filtered, and concentrated under reduced pressure to give a mixture of yellow solid and reddish oil. The oil was isolated by decantation to give the title compound (2.6 g, 47%); $^1$H NMR (400 MHz, Chloroform-d) δ 7.48 (dd, J=7.7, 1.8 Hz, 1H), 7.32-7.21 (m, 1H), 6.98 (d, J=1.1 Hz, 1H), 6.87 (dd, J=8.2, 1.1 Hz, 1H), 5.92-5.72 (m, 1H), 5.45 (dd, J=7.9, 6.3 Hz, 1H), 5.17-5.02 (m, 2H), 3.85 (s, 3H), 2.87-2.76 (m, 2H).

Step 3: 6-Bromo-1-(1-(2-methoxyphenyl)but-3-en-1-yl)-1H-indazol-3(2H)-one

A suspension of potassium carbonate (1.86 g, 13.4 mmol) and 6-bromo-1H-indazol-3-ol (2.6 g, 12 mmol) in DMF (18 mL) was heated at about 50° C. A solution of 1-(1-chlorobut-3-en-1-yl)-2-methoxybenzene (3.84 g, 19.5 mmol) in DMF (30 mL) was added drop-wise over about 20 min. The resulting suspension was allowed to stir at about 50° C. for about 2 days. After cooling to rt, the reaction mixture was poured into ice water (100 mL) and extracted with EtOAc (3×75 mL). The combined organics were washed with water (100 mL) and saturated aqueous NaCl (100 mL), and then dried over $Na_2SO_4$, filtered and concentrated. The material was purified via flash chromatography on silica (0-100% EtOAc/DCM) to give the title compound (1.7 g, 37%); LC/MS (Table A, Method b) $R_t$=2.59 min; MS m/z: 373, 375 $(M+H)^+$.

Step 4: 6-Bromo-1-(3,4-dihydroxy-1-(2-methoxyphenyl)butyl)-1H-indazol-3(2H)-one

A mixture of 6-bromo-1-(1-(2-methoxyphenyl)but-3-en-1-yl)-1H-indazol-3(2H)-one (1.7 g, 4.6 mmol) and NMO (1.60 g, 13.7 mmol) in THF (23 mL) was cooled in an ice water bath, and osmium tetroxide (4% in $H_2O$) (2.89 g, 0.455 mmol) was added drop-wise. The resulting suspension was stirred for about 2 h, after which the ice bath was removed and stirring was continued for an additional 2 h. The reaction was then quenched with 10% aqueous $Na_2S_2O_3$ (20 mL) and stirred for about 1 h. The mixture was partitioned between EtOAc (50 mL) and water (10 mL). After separating the layers, the aqueous phase was extracted with EtOAc (2×25 mL). The combined organic phases were washed with saturated aqueous NaCl (75 mL), dried over $Na_2SO_4$, filtered, and concentrated under reduced pressure to give the title compound (1.76 g, 95%); LC/MS (Table A, Method b) $R_t$=1.83 and 1.87 min; MS m/z: 407, 409 $(M+H)^+$.

Step 5: 3-(6-Bromo-3-oxo-2,3-dihydro-1H-indazol-1-yl)-3-(2-methoxyphenyl)propanal A solution of 6-bromo-1-(3,4-dihydroxy-1-(2-methoxyphenyl)butyl)-1H-indazol-3(2H)-one (1.99 g, 4.89 mmol) in THF (39 mL)/water (9.8 mL) was treated with sodium periodate (1.57 g, 7.33 mmol) while stirring at rt. After about 3 h, the reaction mixture was partitioned between EtOAc (100 mL) and water (50 mL). The layers were separated, and then the aqueous phase was extracted with EtOAc (100 mL). The combined organic phases were washed with saturated aqueous NaCl (125 mL), dried over $Na_2SO_4$, filtered, and concentrated under reduced pressure to give the title compound (1.67 g, 91%); LC/MS (Table A, Method b) $R_t$=2.11 min; MS m/z: 375, 377 $(M+H)^+$.

Step 6: 6-Bromo-1-(3-hydroxy-1-(2-methoxyphenyl)propyl)-1H-indazol-3(2H)-one

A solution of 3-(6-bromo-3-oxo-2,3-dihydro-1H-indazol-1-yl)-3-(2-methoxyphenyl)propanal (1.67 g, 4.45 mmol) in THF (44.5 mL) was cooled at about 0° C. in an ice water bath for about 10 min, after which was treated with $NaBH_4$ (0.168 g, 4.45 mmol) and then allowed to stir at about 0° C. for about 1.5 h. The reaction mixture was quenched at 0° C. by careful addition of saturated aqueous $NH_4Cl$ (50 mL) and then diluted with EtOAc (50 mL). After separating the layers, the aqueous phase was extracted with EtOAc (2×25 mL), and the combined organic phases were washed with saturated aqueous NaCl (75 mL), dried over $Na_2SO_4$, filtered, and concentrated under reduced pressure. The material was purified via flash chromatography on silica gel (0-100% EtOAc/DCM) to give the title compound (1.39 g, 83%); LC/MS (Table A, Method b) $R_t$=2.03 min; MS m/z: 377, 379 $(M+H)^+$.

Step 7: 6-Bromo-3-(2-methoxyphenyl)-2,3-dihydropyrazolo[1,2-a]indazol-9(1H)-one

A mixture of 6-bromo-1-(3-hydroxy-1-(2-methoxyphenyl)propyl)-1H-indazol-3(2H)-one (1.4 g, 3.7 mmol) and 2,6-lutidine (1.3 mL, 11 mmol) in DCM (37.1 mL) was treated with XtalFluor-E® (1.28 g, 5.57 mmol) and the resulting solution was stirred at rt for about 20 min. The reaction mixture was then quenched at rt by addition of saturated aqueous $NaHCO_3$ (50 mL) and diluted with DCM (25 mL). The aqueous phase was extracted with DCM (15 mL), and then the combined organic phases were washed with 1M Aq HCl (50 mL) and saturated aqueous NaCl (50 mL), dried over $Na_2SO_4$, filtered, and concentrated under reduced pressure. The material was purified via flash chromatography on silica gel (0-100% EtOAc/DCM) to give the title compound (0.80 g, 60%); LC/MS (Table A, Method b) $R_t$=2.22 min; MS m/z: 359, 361 $(M+H)^+$.

Preparation #18: 6-(2-(2-Hydroxypropan-2-yl)pyrimidin-5-yl)-3-(2-methoxyphenyl)-2,3-dihydropyrazolo[1,2-a]indazol-9(1H)-one

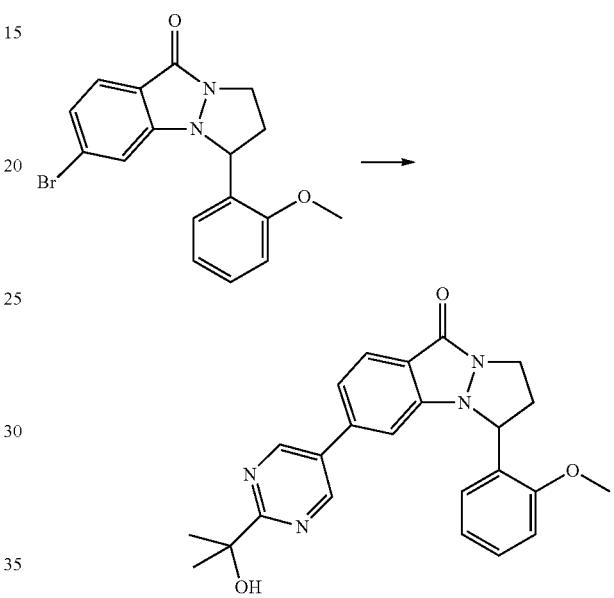

A mixture of 2-(5-bromopyrimidin-2-yl)propan-2-ol (0.079 g, 0.36 mmol), bis(pinacolato)diboron (0.191 g, 0.752 mmol), $PdCl_2$(dppf)-$CH_2Cl_2$ adduct (0.016 g, 0.019 mmol), and KOAc (0.090 g, 0.92 mmol) in 1,4-dioxane (2.25 mL) was heated at reflux for about 1.5 h. The reaction mixture was allowed to cool and then 6-bromo-3-(2-methoxyphenyl)-2,3-dihydropyrazolo[1,2-a]indazol-9(1H)-one (0.100 g, 0.278 mmol) (Preparation #17), bis(triphenylphosphine)palladium dichloride (9.8 mg, 0.014 mmol), cesium carbonate (0.227 g, 0.696 mmol) and water (0.5 mL) were added. The reaction mixture was heated at about 80° C. for about 30 min, and then cooled to rt, during which the aqueous and organic portions separated. The organics were filtered through a 0.45 µM GHP Acrodisc syringe filter and then through a pad of Celite®. The sample was purified by reverse phase chromatography (Table C, Method 2). The appropriate fractions were combined and the volatiles evaporated under reduced pressure. The aqueous mixture was extracted with EtOAc (3×20 mL) and then the combined organic phases were washed with saturated aqueous NaCl (50 mL), dried over $Na_2SO_4$, filtered, and concentrated under reduced pressure. The residue was triturated with diethyl ether (10 mL), and the resulting solid was recovered by vacuum filtration and air dried to give the title compound (0.080 g, 69%); LC/MS (Table A, Method b) $R_t$=1.81 min; MS m/z: 417 $(M+H)^+$.

Preparation #19: 2-(1-Hydroxybut-3-en-1-yl)-6-methylbenzonitrile

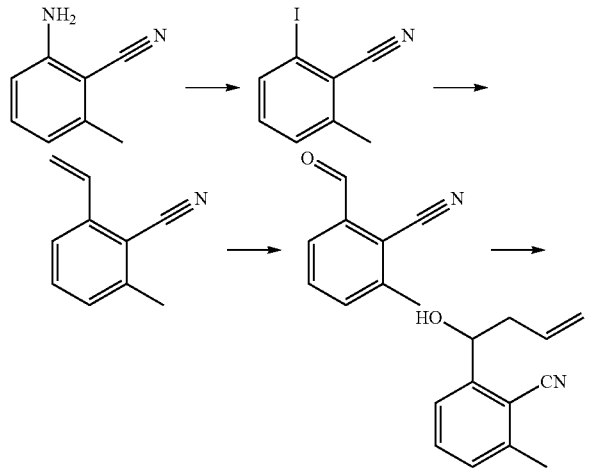

Step 1: 2-Iodo-6-methylbenzonitrile

A flask was charged with concentrated sulfuric acid (100 mL, 1.88 mol). 2-Amino-6-methylbenzonitrile (10 g, 76 mmol) was gradually added and then the mixture was stirred at rt for about 16 h. The mixture was cooled to about −5° C. then sodium nitrite (5.74 g, 83.0 mmol) was gradually added. The reaction mixture was stirred at about 0° C. for about 2.5 h then added into mixture of ice/water (200 g) and potassium iodide (16 g, 96 mmol). The mixture was stirred at about 0° C. for about 10 min and then at ambient temperature for about 2.5 h. The mixture was extracted with $Et_2O$ (400 mL). The aqueous layer was extracted with $Et_2O$ (50 mL). The combined organics were washed with 10% aqueous $NaS_2O_3$ (400 mL) then dried over $MgSO_4$, filtered, and concentrated. The material was triturated with DCM (25 mL) and the resulting solids were collected by filtration. The filtrate was concentrated under reduced pressure and the residue was purified via flash chromatography on silica gel (1-15% EtOAc/heptane) to give the title compound (13.2 g, 72%); $^1$H NMR (400 MHz, $CDCl_3$) δ 7.76-7.71 (m, 1H), 7.31-7.27 (m, 1H), 7.18-7.13 (m, 1H), 2.59 (s, 3H).

Step 2: 2-Methyl-6-vinylbenzonitrile

A flask was charged with 2-iodo-6-methylbenzonitrile (1.10 g, 4.53 mmol), 4,4,5,5-tetramethyl-2-vinyl-1,3,2-dioxaborolane (1.39 g, 9.05 mmol), cesium carbonate (4.42 g, 13.6 mmol), 1,4-dioxane (20 mL) and water (5.0 mL). The reaction vessel was evacuated then back-filled with $N_2$ three times. $Pd(PPh_3)_4$ (0.37 g, 0.32 mmol) was added. The reaction vessel was evacuated then back-filled with $N_2$ three times. The reaction was heated at about 90° C. for about 3 h. After cooling to ambient temperature, the mixture was partitioned between saturated aqueous $NaHCO_3$ (20 mL) and EtOAc (50 mL). The organic layer was dried over $MgSO_4$, filtered, and concentrated. DCM (10 mL) was added and the solid was removed by filtration. The filtrate was concentrated under reduced pressure and the residue was purified via flash chromatography on silica gel (5-10% EtOAc/heptane) to give the title compound (0.85 g, 66%); $^1$H NMR (400 MHz, $CDCl_3$) δ 7.45-7.33 (m, 2H), 7.17-7.11 (m, 1H), 7.08-6.98 (m, 1H), 5.88-5.82 (m, 1H), 5.48-5.42 (m, 1H), 2.55 (s, 3H).

Step 3: 2-Formyl-6-methylbenzonitrile

A flask was charged with 2-methyl-6-vinylbenzonitrile (7.00 g, 48.9 mmol). Osmium(VIII) oxide (4% water solution, 12.4 g, 1.96 mmol), sodium periodate (30.3 g, 142 mmol), acetone (300 mL) and water (50 mL) were added. After mixing at ambient temperature for about 2.5 h, the solids were removed by filtration and rinsed with acetone (50 mL). The organic volatiles were removed under reduced pressure. The residue was extracted with EtOAc (200 mL). The organic layer was washed with saturated aqueous NaCl (25 mL). The aqueous layer was extracted with EtOAc (50 mL). The combined organics were dried over $MgSO_4$, filtered and concentrated under reduced pressure. The residue was purified via flash chromatography on silica gel (5-18% EtOAc/heptane) to give the title compound (4.3 g, 61%); $^1$H NMR (400 MHz, $CDCl_3$) δ 10.36 (s, 1H), 7.89-7.85 (m, 1H), 7.68-7.58 (m, 2H), 2.66 (s, 3H).

Step 4: 2-(1-Hydroxybut-3-en-1-yl)-6-methylbenzonitrile

A flask was charged with diacetoxypalladium (0.186 g, 0.827 mmol), DMAP (0.404 g, 3.31 mmol) and DMF (30 mL). 2-Formyl-6-methylbenzonitrile (4.00 g, 27.6 mmol), 3-bromoprop-1-ene (2.58 mL, 29.8 mmol) and tin(II) chloride dihydrate (8.71 g, 38.6 mmol) were added successively. The mixture was warmed to about 44° C. for about 30 min. The reaction was cooled to rt, added to water (200 mL) then extracted with $Et_2O$ (200 mL). The aqueous layer was extracted with $Et_2O$ (2×30 mL). The combined organics were washed with saturated aqueous NaCl (30 mL), dried over $MgSO_4$, filtered and concentrated under reduced pressure. The residue was purified via flash chromatography on silica gel (5-30% EtOAc/heptane) to give the title compound (3.5 g, 68%); LC/MS (Table A, Method b) $R_t$=1.94 min; MS m/z: 188 $(M+H)^+$.

Preparation #20: rac-(1R,9bR)-8-Bromo-1-(2-(difluoromethoxy)phenyl)-2,3-dihydro-1H-pyrrolo[2,1-a]isoindol-5(9bH)-one

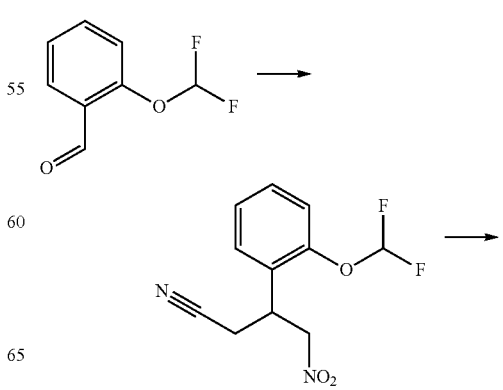

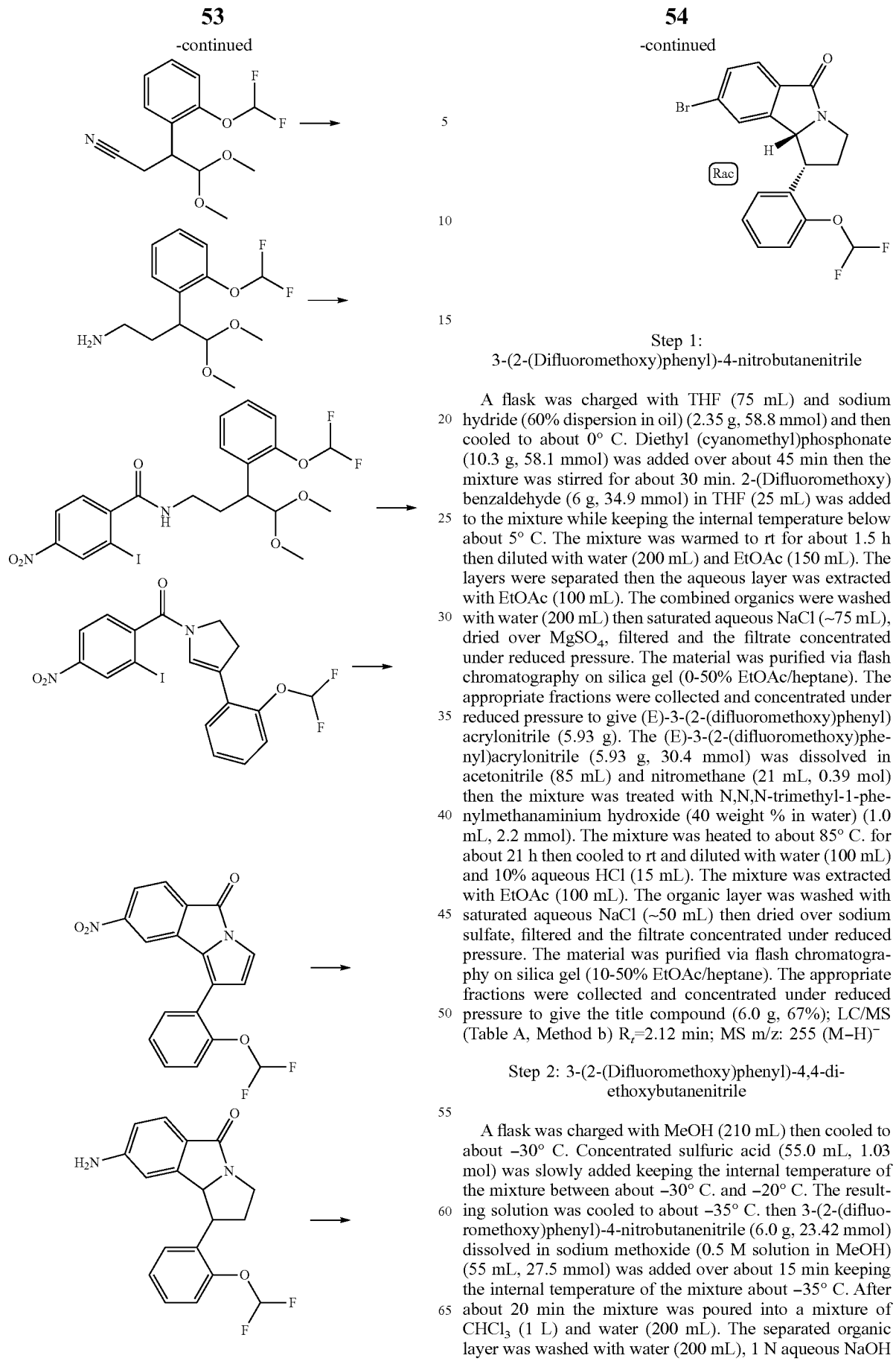

Step 1:
3-(2-(Difluoromethoxy)phenyl)-4-nitrobutanenitrile

A flask was charged with THF (75 mL) and sodium hydride (60% dispersion in oil) (2.35 g, 58.8 mmol) and then cooled to about 0° C. Diethyl (cyanomethyl)phosphonate (10.3 g, 58.1 mmol) was added over about 45 min then the mixture was stirred for about 30 min. 2-(Difluoromethoxy)benzaldehyde (6 g, 34.9 mmol) in THF (25 mL) was added to the mixture while keeping the internal temperature below about 5° C. The mixture was warmed to rt for about 1.5 h then diluted with water (200 mL) and EtOAc (150 mL). The layers were separated then the aqueous layer was extracted with EtOAc (100 mL). The combined organics were washed with water (200 mL) then saturated aqueous NaCl (~75 mL), dried over MgSO$_4$, filtered and the filtrate concentrated under reduced pressure. The material was purified via flash chromatography on silica gel (0-50% EtOAc/heptane). The appropriate fractions were collected and concentrated under reduced pressure to give (E)-3-(2-(difluoromethoxy)phenyl)acrylonitrile (5.93 g). The (E)-3-(2-(difluoromethoxy)phenyl)acrylonitrile (5.93 g, 30.4 mmol) was dissolved in acetonitrile (85 mL) and nitromethane (21 mL, 0.39 mol) then the mixture was treated with N,N,N-trimethyl-1-phenylmethanaminium hydroxide (40 weight % in water) (1.0 mL, 2.2 mmol). The mixture was heated to about 85° C. for about 21 h then cooled to rt and diluted with water (100 mL) and 10% aqueous HCl (15 mL). The mixture was extracted with EtOAc (100 mL). The organic layer was washed with saturated aqueous NaCl (~50 mL) then dried over sodium sulfate, filtered and the filtrate concentrated under reduced pressure. The material was purified via flash chromatography on silica gel (10-50% EtOAc/heptane). The appropriate fractions were collected and concentrated under reduced pressure to give the title compound (6.0 g, 67%); LC/MS (Table A, Method b) R$_t$=2.12 min; MS m/z: 255 (M−H)$^-$ Step 2: 3-(2-(Difluoromethoxy)phenyl)-4,4-diethoxybutanenitrile A flask was charged with MeOH (210 mL) then cooled to about −30° C. Concentrated sulfuric acid (55.0 mL, 1.03 mol) was slowly added keeping the internal temperature of the mixture between about −30° C. and −20° C. The resulting solution was cooled to about −35° C. then 3-(2-(difluoromethoxy)phenyl)-4-nitrobutanenitrile (6.0 g, 23.42 mmol) dissolved in sodium methoxide (0.5 M solution in MeOH) (55 mL, 27.5 mmol) was added over about 15 min keeping the internal temperature of the mixture about −35° C. After about 20 min the mixture was poured into a mixture of CHCl$_3$ (1 L) and water (200 mL). The separated organic layer was washed with water (200 mL), 1 N aqueous NaOH (200 mL) then water (200 mL), dried over sodium sulfate, filtered and concentrated under reduced pressure. The material was purified via flash chromatography on silica gel (10-50% EtOAc/heptane). The appropriate fractions were collected and concentrated under reduced pressure to give the title compound (3.62 g, 57%); $^1$H NMR (400 MHz, CDCl$_3$) δ 7.42 (dd, J=7.7, 1.8 Hz, 1H), 7.35-7.29 (m, 1H), 7.26-7.22 (m, 1H), 7.14-7.12 (m, 1H), 6.53 (t, J=74 Hz, 1H)), 4.57 (d, J=5.8 Hz, 1H), 3.79-3.71 (m, 1H), 3.41 (s, 3H), 3.32 (s, 3H), 2.88-2.72 (m, 2H).

Step 3: 3-(2-(Difluoromethoxy)phenyl)-4,4-dimethoxybutan-1-amine

A flask was charged with 3-(2-(difluoromethoxy)phenyl)-4,4-dimethoxybutanenitrile (0.925 g, 3.41 mmol), MeOH (40 mL) and cobalt(II) chloride hexahydrate (1.87 g, 7.84 mmol). Sodium borohydride (0.645 g, 17.0 mmol) was added then the mixture was stirred for about 15 min. The mixture was filtered through a bed of Celite® then the pad was washed with McOH (30 mL). The filtrate was concentrated to give the crude title compound (3.15 g); LC/MS (Table A, Method b) R$_t$=1.38 min; MS m/z: 276 (M+H)$^+$.

Step 4: N-(3-(2-(Difluoromethoxy)phenyl)-4,4-dimethoxybutyl)-2-iodo-4-nitrobenzamide A flask was charged with 2-iodo-4-nitrobenzoic acid (1.0 g, 3.41 mmol) in DCM (25 mL), oxalyl chloride (0.597 mL, 6.83 mmol) and a drop of DMF. After about 20 min the mixture was concentrated under reduced pressure, dissolved in DCM (25 mL) then added to the crude 3-(2-(difluoromethoxy)phenyl)-4,4-dimethoxybutan-1-amine (3.15 g from step 3, assumed 3.41 mmol) in DCM (25 mL) with TEA (5 mL, 35.9 mmol). The mixture was stirred for about 15 min at rt then water (50 mL) was added and stirring continued for about 5 min. The solvent layers were separated then the aqueous layer was extracted with DCM (20 mL). The combined organics were washed with saturated sodium bicarbonate (2×20 mL) then dried over MgSO$_4$, filtered and concentrated under reduced pressure. The material was purified via flash chromatography on silica gel (0-25% EtOAc/DCM). The appropriate fractions were collected and concentrated under reduced pressure to give the title compound (1.23 g, 66%); LC/MS (Table A, Method b) R$_t$=2.37 min; MS m/z: 549 (M−H)$^-$ Step 5: (4-(2-(Difluoromethoxy)phenyl)-2,3-dihydro-1H-pyrrol-1-yl)(2-iodo-4-nitrophenyl)methanone A flask was charged with N-(3-(2-(difluoromethoxy)phenyl)-4,4-dimethoxybutyl)-2-iodo-4-nitrobenzamide (1.23 g, 2.23 mmol) and DCM (25 mL). Trifluoromethanesulfonic acid (0.444 mL, 5.00 mmol) was added and then the mixture was stirred for about 15 min. Water (20 mL) was added then the solvent layers were separated. The organic layer was washed with saturated sodium bicarbonate, dried over MgSO$_4$, filtered and the filtrate concentrated to give the title compound (1.09 g, 100%); LC/MS (Table A, Method b) R$_t$=2.41 min; MS m/z: 487 (M+H)$^+$ Step 6: 1-(2-(Difluoromethoxy)phenyl)-8-nitro-5H-pyrrolo[2,1-a]isoindol-5-one A mixture of (4-(2-(difluoromethoxy)phenyl)-2,3-dihydro-1H-pyrrol-1-yl)(2-iodo-4-nitrophenyl)methanone (2.37 g, 4.87 mmol), silver phosphate (2.65 g, 6.34 mmol), PdCl$_2$(PPh$_3$)$_2$ (0.342 g, 0.487 mmol), and DMA (50.0 mL) was evacuated then back-filled with N$_2$ three times. After purging with N$_2$ for about 45 min, the mixture was warmed to about 100° C. for about 1 h. After cooling to rt, the mixture was filtered rinsing with EtOAc (75 mL). The volatiles were removed under reduced pressure. The residue was via flash chromatography on silica gel (DCM) to give the title compound (0.982 g, 56%); $^1$H NMR (400 MHz, CDCl$_3$) δ 8.06 (dd, J=8.2, 2.0 Hz, 1H), 8.00 (dd, J=2.0, 0.6 Hz, 1H), 7.83 (dd, J=8.2, 0.6 Hz, 1H), 7.56 (ddd, J=7.6, 1.8, 0.4 Hz, 1H), 7.47 (ddd, J=8.2, 7.5, 1.8 Hz, 1H), 7.40-7.31 (m, 2H), 7.18 (d, J=3.3 Hz, 1H), 6.47 (t, J=73.5 Hz, 1H), 6.45 (d, J=3.4 Hz, 1H).

Step 7: 8-Amino-1-(2-(difluoromethoxy)phenyl)-2,3-dihydro-1H-pyrrolo[2,1-a]isoindol-(9bH)-one EtOH (34.0 mL) was added to Pd/C (10 wt % on activated carbon, 0.723 g, 0.679 mmol) under N$_2$. 1-(2-(Difluoromethoxy)phenyl)-8-nitro-5H-pyrrolo[2,1-a]isoindol-5-one (1.21 g, 3.40 mmol) was added. The mixture was shaken under about 50 psi of hydrogen for about 2.5 h. The hydrogen atmosphere was evacuated using house vacuum for about 10 min then the mixture was filtered through Celite® rinsing with MeOH (80 mL). The volatiles were removed under reduced pressure to give the title compound (1.12 g, 100%); LC/MS (Table A, Method b) R$_t$=1.85 min; MS m/z: 331 (M+H)$^+$.

Step 8: rac-(1R,9bR)-1-Bromo-1-(2-(difluoromethoxy)phenyl)-2,3-dihydro-1H-pyrrolo[2,1-a]isoindol-5(9bH)-one A solution of HBr (48 wt % in water, 1.20 mL, 10.61 mmol) and water (3.00 mL) was added to a solution of 8-amino-1-(2-(difluoromethoxy)phenyl)-2,3-dihydro-1H-pyrrolo[2,1-a]isoindol-5(9bH)-one (1.19 g, 3.60 mmol) and acetonitrile (30.0 mL) under N$_2$ at about 0° C. A solution of sodium nitrite (0.300 g, 4.35 mmol) and water (3.00 mL) was added dropwise over about 2 min. After about 30 min, copper(II) bromide (1.22 g, 5.46 mmol) was added. After about 30 min, the ice bath was removed. After about 40 min at rt, water (50 mL) and EtOAc (100 mL) were added. The layers were separated and the organics were washed with water (50 mL) and saturated aqueous NaHCO$_3$ (50 mL) then dried over Na$_2$SO$_4$, filtered, and concentrated under reduced pressure. The residue was purified via flash chromatography on silica gel (1-10% EtOAc/DCM) to give a light tan solid (1.25 g). The material was dissolved in refluxing MeOH (5 mL) then allowed to cool to rt. After stirring for about 1 h, the solid was collected by filtration rinsing with MeOH (2×1 mL). A second crop was obtained from the residue of the mother liquor using refluxing MeOH (0.75 mL) and rinsing with MeOH (2×0.5 mL). The two crops were combined then dried to give the title compound (0.942 g, 69%); LC/MS (Table A, Method b) R$_t$=2.34 min; MS m/z: 394 and 396 (M+H)$^+$.

Preparation #21: (1S,9bS)-8-Bromo-1-(2-(difluoromethoxy)phenyl)-2,3-dihydro-1H-pyrrolo[2,1-a]isoindol-5(9bH)-one

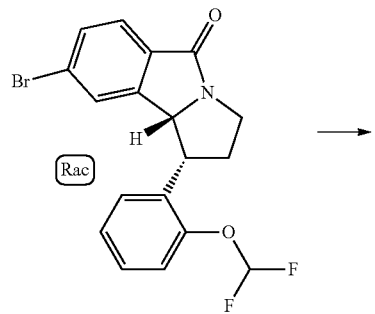

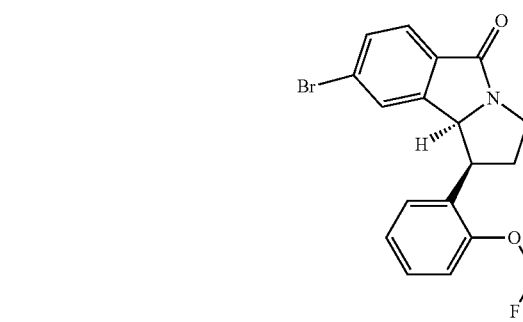

rac-(1R,9bR)-8-Bromo-1-(2-(difluoromethoxy)phenyl)-2,3-dihydro-1H-pyrrolo[2,1-a]isoindol-5(9bH)-one (0.947 g, 2.40 mmol) (Preparation #20) was submitted for chiral purification (Table B, Method 15). Fractions from the first eluding component were combined and concentrated under reduced pressure then dried to give the title compound (0.372 g, 39%) with negative (−) optical rotation; LC/MS (Table A, Method a) $R_t$=2.31 min; MS m/z: 394 and 396 (M+H)$^+$

Preparation #22: (1R,9bR)-8-Bromo-1-(2-(difluoromethoxy)phenyl)-2,3-dihydro-1H-pyrrolo[2,1-a]isoindol-5(9bH)-one

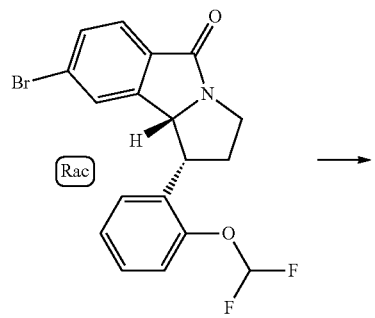

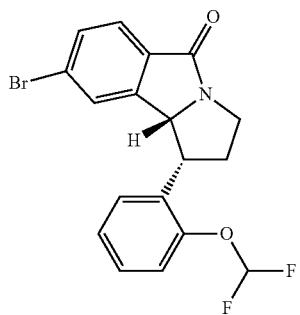

rac-(1R,9bR)-8-Bromo-1-(2-(difluoromethoxy)phenyl)-2,3-dihydro-1H-pyrrolo[2,1-a]isoindol-5(9bH)-one (0.947 g, 2.40 mmol) (Preparation #20) was submitted for chiral purification (Table B, Method 15). Fractions from the second eluding component were combined and concentrated under reduced pressure then dried to give the title compound (0.356 g, 37%) with positive (+) optical rotation; LC/MS (Table A, Method a) $R_t$=2.31 min; MS m/z: 394 and 396 (M+H)$^+$

Preparation #23: 6-Bromo-5-fluoro-1H-indazol-3(2H)-one

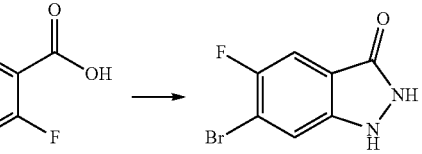

To a mixture of 4-bromo-2,5-difluorobenzoic acid (5.0 g, 21 mmol) in DCM (80 mL) was slowly added oxalyl chloride (2.8 mL, 32 mmol) at rt. DMF (0.02 mL, 0.258 mmol) was added then the mixture was stirred for about 2.5 h. The mixture was concentrated under reduced pressure then the residue was dissolved in DCM (40 mL). The solution was slowly added to hydrazine (3.3 mL, 150 mmol) in DCM (40 mL) at about −35 to −50° C. The mixture was warmed to about 5° C. then the solids were collected by filtration and washed with DCM (50 mL) then Et$_2$O (50 mL). The material was dried under vacuum to yield 4.9 g of tan solid. The material was added to n-butanol (130 mL) with hydrazine hydrate (10 mL, 205 mmol) then heated to about 120° C. for about 22 h. The mixture was concentrated under reduced pressure to about one half volume. Solids were collected by filtration and discarded. The filtrate was concentrated to dryness then triturated with EtOAc (50 mL). Solids were collected by filtration and dried under vacuum to give the title compound (1.2 g, 25%); $^1$H NMR (400 MHz, DMSO-d$_6$) δ 11.23 (bs, 2H), 7.64 (d, J=5.5 Hz, 1H), 7.52 (dd, J=8.7, 1.2 Hz, 1H).

Preparation #24: 6-Bromo-1-(1-(2-(difluoromethoxy)phenyl)-3-hydroxypropyl)-5-fluoro-1H-indazol-3(2H)-one

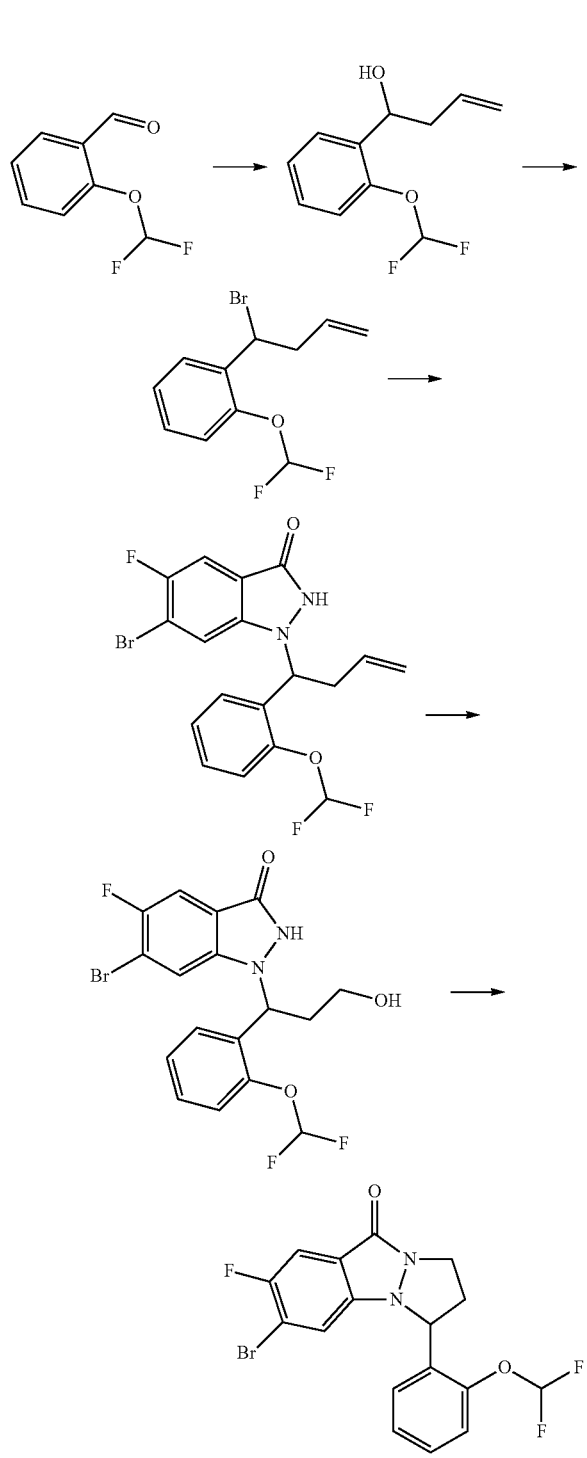

6-Bromo-1-(1-(2-(difluoromethoxy)phenyl)-3-hydroxypropyl)-5-fluoro-1H-indazol-3(2H)-one was synthesized in a manner similar to Preparation #1, steps 1 through 5 from 2-(difluoromethoxy)benzaldehyde and 6-bromo-5-fluoro-1H-indazol-3(2H)-one (Preparation #23); LC/MS (Table A, Method d) $R_t$=1.44 min; MS m/z: 413 and 415 (M+H)$^+$

Preparation #25: (R)-1-(4-(5-Bromopyrimidin-2-yl)-2-methylpiperazin-1-yl)ethanone

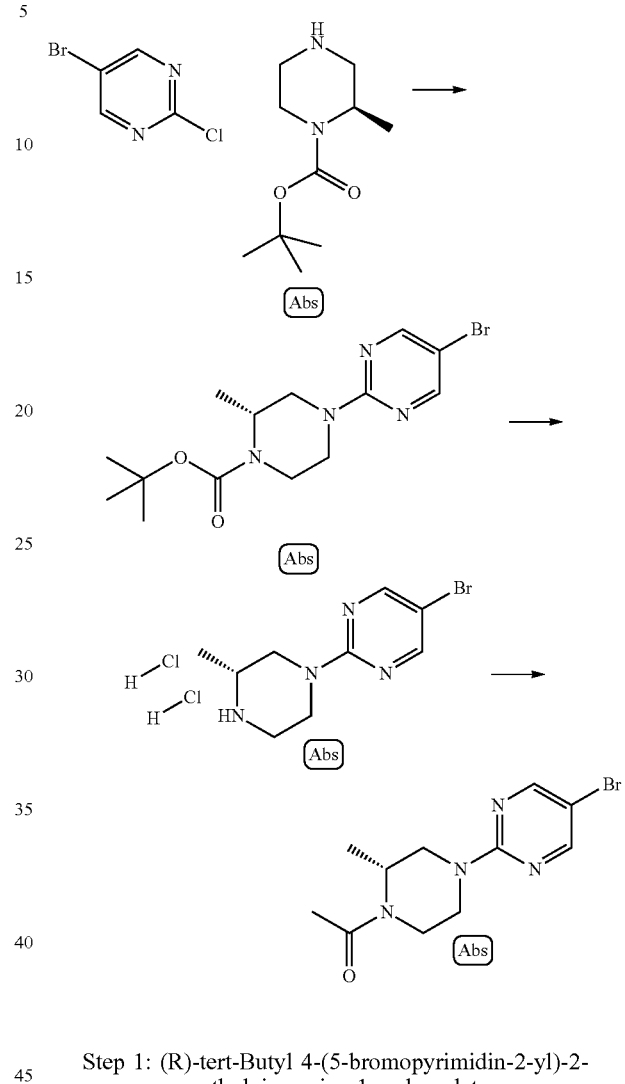

Step 1: (R)-tert-Butyl 4-(5-bromopyrimidin-2-yl)-2-methylpiperazine-1-carboxylate EtOH (250 mL) was added to a mixture of 5-bromo-2-chloropyrimidine (10.1 g, 52.2 mmol) and (R)-1-N-Boc-2-methylpiperazine (10.0 g, 49.9 mmol). TEA (21.0 mL, 151 mmol) was added. The solution was warmed to about 75° C. for about 8 h. The mixture was cooled and concentrated under reduced pressure then the mixture was partitioned between water (100 ml), Et$_2$O (100 mL) and EtOAc (100 mL). The layers were separated then the organic layer was washed with water (100 mL). The aqueous layers were extracted with EtOAc (50 mL). The combined organic layers were dried over Na$_2$SO$_4$, filtered, and concentrated. The material was purified via flash chromatography on silica gel (0-25% EtOAc/heptane) to give the title compound (16.6 g, 94%); LC/MS (Table A, Method d) $R_t$=1.86 min; MS m/z: 301 and 303 (M+H)$^+$

Step 2: (R)-5-Bromo-2-(3-methylpiperazin-1-yl)pyrimidine dihydrochloride

To a solution of (R)-tert-butyl 4-(5-bromopyrimidin-2-yl)-2-methylpiperazine-1-carboxylate (4 g, 11.20 mmol) in 1,4-dioxane (40 mL) was added hydrogen chloride (28.0 ml, 112 mmol) (4N in 1,4-dioxane) at rt. The reaction was stirred at rt for about 24 h. The solids were collected by filtration and washed with diethyl ether then dried under vacuum to give the title compound (3.67 g, 99%); LC/MS (Table A, Method d) $R_t$=1.86 min; MS m/z: 257 and 259 (M+H)$^+$ Step 3: (R)-1-(4-(5-Bromopyrimidin-2-yl)-2-methyl-piperazin-1-yl)ethanone (R)-5-Bromo-2-(3-methylpiperazin-1-yl)pyrimidine dihydrochloride (3.67 g, 11.12 mmol) in DCM (100 mL) was treated with TEA (5.1 mL, 37 mmol). Acetyl chloride (0.90 mL, 12.8 mmol) was added while maintaining the reaction temperature below 30° C. After complete addition the mixture was washed with water (50 mL) and brine (50 mL) then dried over sodium sulfate, filtered and concentrated under reduced pressure to give the title compound (3.32 g, 99%) LC/MS (Table A, Method d) $R_t$=0.45 min; MS m/z: 257 and 259 (M+H)$^+$ Preparation #26: (R)-1-(4-(5-bromopyrimidin-2-yl)-2-methylpiperazin-1-yl)-2-hydroxyethanone

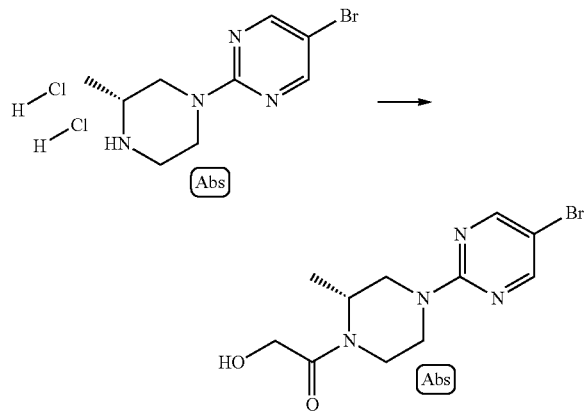

(R)-5-Bromo-2-(3-methylpiperazin-1-yl)pyrimidine dihydrochloride (2.0 g, 6.06 mmol), glycolic acid (0.69 g, 9.1 mmol) and HATU (2.76 g, 7.27 mmol) in DMF (30 mL) was treated with TEA (3.4 mL, 24 mmol) then stirred for about 90 min. The mixture was concentrated under reduced pressure then water and saturated aqueous sodium bicarbonate were added. The mixture was extracted with EtOAc (75 mL). The organic solution was washed with brine, dried over magnesium sulfate, filtered and concentrated. The material was purified via flash chromatography on silica gel (0-100% EtOAc/DCM) to give the title compound (1.89 g, 99%); LC/MS (Table A, Method d) $R_t$=0.90 min; MS m/z: 315 and 317 (M+H)$^+$ Preparation #27: 2-(Difluoromethoxy)-5-methylbenzaldehyde

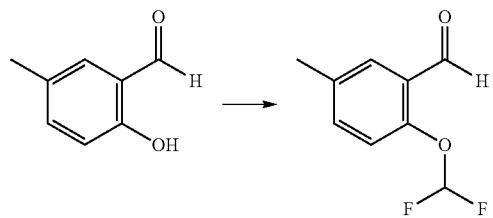

2-Hydroxy-5-methylbenzaldehyde (20 g, 147 mmol) in MeCN (500 mL) was cooled to about −25° C. A solution of KOH (165 g, 2938 mmol) in water (500 mL) was added over about 30 min keeping the temperature of the mixture below about −25° C. The mixture was cooled to an internal temperature of about −35° C. then diethyl (bromodifluoromethyl)phosphonate (58.8 g, 220 mmol) was added over about 5 min. The mixture was warmed to about 5° C. Diethyl ether (1 L) was added then the phases were allowed to separate. The organic layer was washed with water and brine (1 L each) and then dried over sodium sulfate and filtered. The filtrate was concentrated under reduced pressure then the material was purified via silica gel chromatography (0-30% EtOAc/heptane) to give the title compound (15.2 g, 56%); $^1$H NMR (400 MHz, Chloroform-d) δ 10.36 (s, 1H), 7.73 (d, J=1.5 Hz, 1H), 7.41 (dd J=8.4, 1.5 Hz, 1H), 7.13 (d, J=8.4 Hz, 1H), 6.61 (J=73.1 Hz, 1H), 2.39 (s, 3H).

Preparation #28: 6-Bromo-3-(2-(difluoromethoxy)-5-methylphenyl)-2,3-dihydropyrazolo[1,2-a]indazol-9(1H)-one

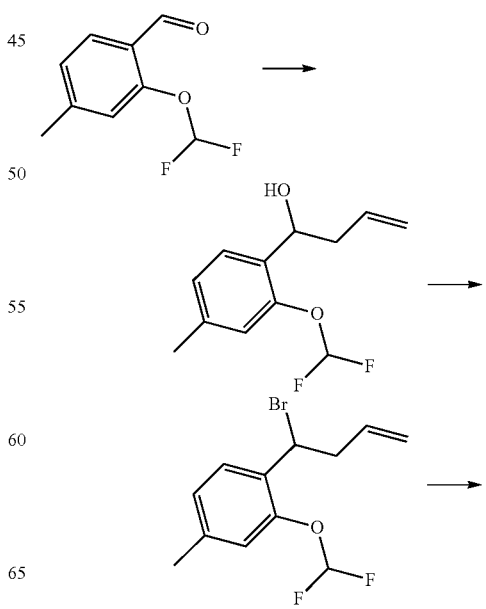

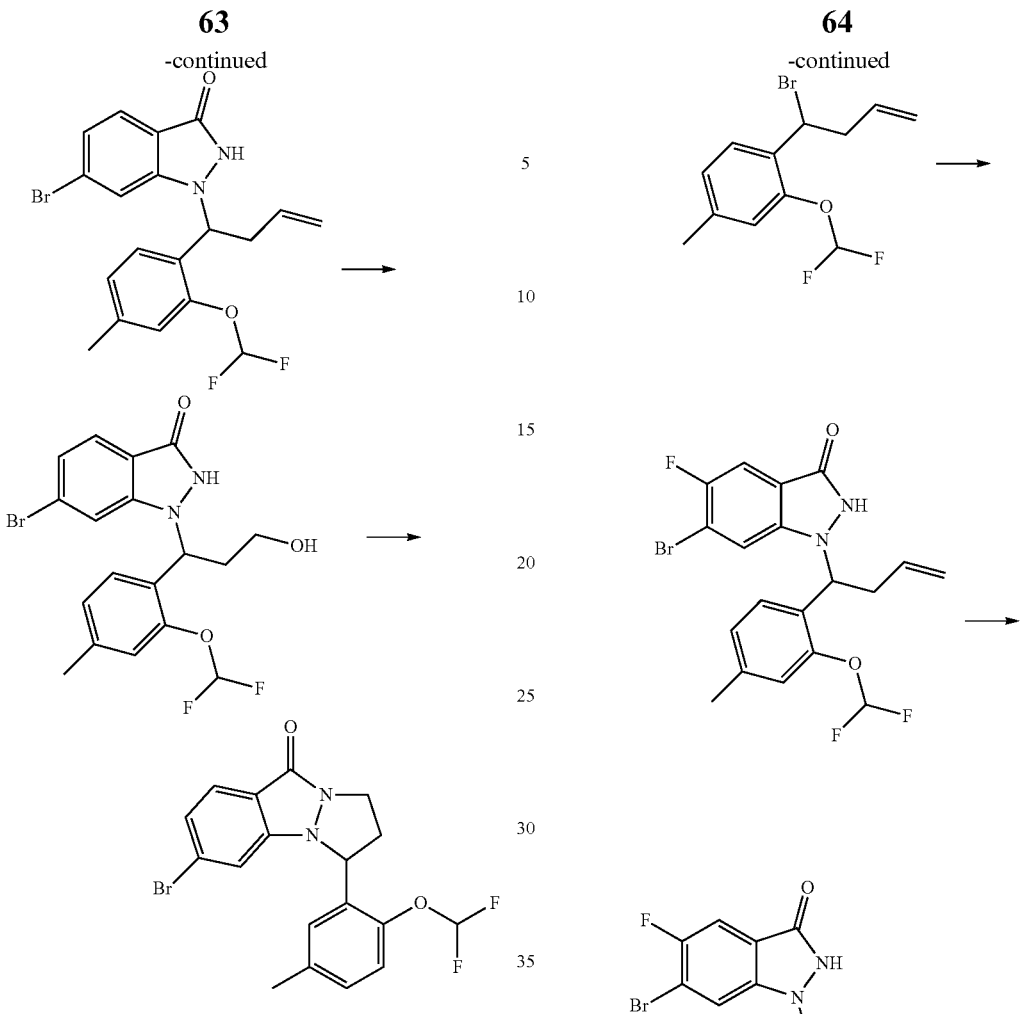

6-Bromo-3-(2-(difluoromethoxy)-5-methylphenyl)-2,3-dihydropyrazolo[1,2-a]indazol-9(1H)-one was synthesized in a manner similar to Preparation #1, steps 1 through 5 from 2-(difluoromethoxy)-5-methylbenzaldehyde (Preparation #27) and 6-bromo-1H-indazol-3(2H)-one; LC/MS (Table A, Method d) $R_t$=1.53 min; MS m/z: 409 and 411 (M+H)$^+$ Preparation #29: 6-Bromo-3-(2-(difluoromethoxy)-5-methylphenyl)-7-fluoro-2,3-dihydropyrazolo[1,2-a]indazol-9(1H)-one

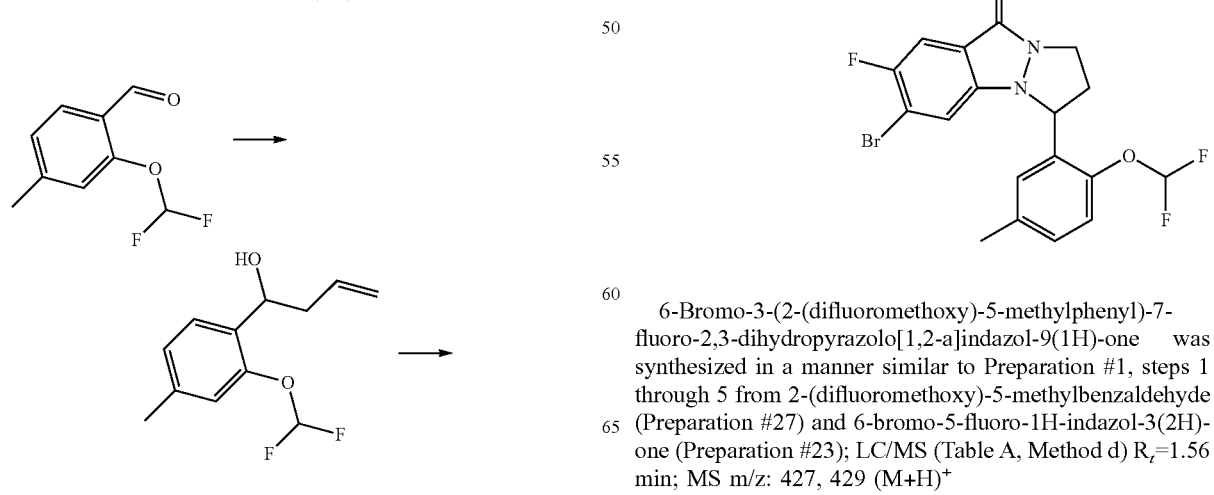

6-Bromo-3-(2-(difluoromethoxy)-5-methylphenyl)-7-fluoro-2,3-dihydropyrazolo[1,2-a]indazol-9(1H)-one was synthesized in a manner similar to Preparation #1, steps 1 through 5 from 2-(difluoromethoxy)-5-methylbenzaldehyde (Preparation #27) and 6-bromo-5-fluoro-1H-indazol-3(2H)-one (Preparation #23); LC/MS (Table A, Method d) $R_t$=1.56 min; MS m/z: 427, 429 (M+H)$^+$ Preparation #30: (S)-6-Bromo-3-(2-(difluoromethoxy)-5-methylphenyl)-2,3-dihydropyrazolo[1,2-a]indazol-9(1H)-one

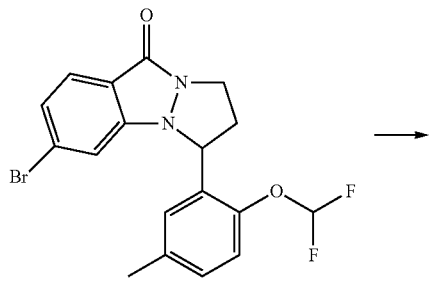

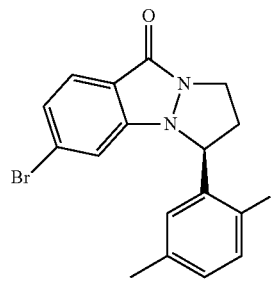

6-Bromo-3-(2-(difluoromethoxy)-5-methylphenyl)-2,3-dihydropyrazolo[1,2-a]indazol-9(1H)-one (0.322 g, 0.787 mmol) (Preparation #28) was submitted for chiral purification (Table B, Method 20). Fractions from the first eluting component were combined and concentrated under reduced pressure then taken into water, frozen and lyophilized to give the title compound (0.148 g, 22%) with an inconclusive optical rotation. LC/MS (Table A, Method a) R$_t$=2.34 min; MS m/z: 409, 411 (M+H)$^+$.

Preparation #31: (R)-6-Bromo-3-(2-(difluoromethoxy)-5-methylphenyl)-2,3-dihydropyrazolo[1,2-a]indazol-9(1H)-one

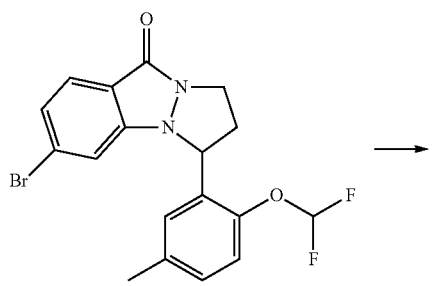

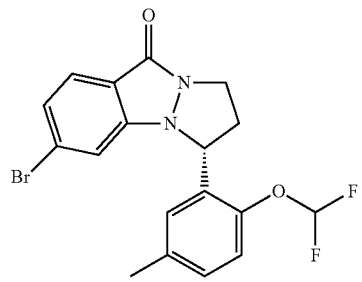

6-Bromo-3-(2-(difluoromethoxy)-5-methylphenyl)-2,3-dihydropyrazolo[1,2-a]indazol-9(1H)-one (0.322 g, 0.787 mmol) (Preparation #28) was submitted for chiral purification (Table B, Method 20). Fractions from the second eluting component were combined and concentrated under reduced pressure then taken into water, frozen and lyophilized to give the title compound (0.152 g, 22%) with an inconclusive optical rotation. LC/MS (Table A, Method a) R$_t$=2.34 min; MS m/z: 409, 411 (M+H)$^+$.

Example 1

3-(2-(Difluoromethoxy)phenyl)-6-(2-morpholinopyrimidin-5-yl)-2,3-dihydropyrazolo[1,2-a]indazol-9(1H)-one

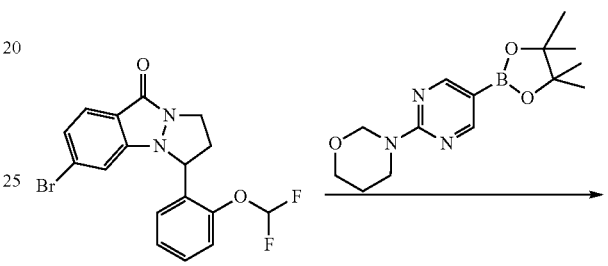

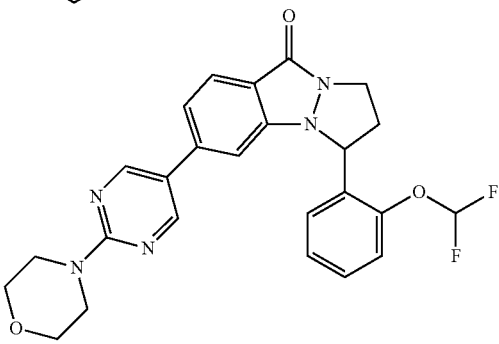

6-Bromo-3-(2-(difluoromethoxy)phenyl)-2,3-dihydropyrazolo[1,2-a]indazol-9(1H)-one (0.400 g, 1.012 mmol) (Preparation #1), 4-(5-(4,4,5,5-tetramethyl-1,3,2-dioxaborolan-2-yl)pyrimidin-2-yl)morpholine (0.442 g, 1.52 mmol) and cesium carbonate (0.989 g, 3.04 mmol) were added to a flask with 1,4-dioxane (3 mL) and water (0.75 mL). The flask was purged and flushed with N$_2$. Pd(Ph$_3$P)$_4$ (0.082 g, 0.071 mmol) was then added and mixture was purged again and then heated to 90° C. under N$_2$ for about 30 min. The mixture was cooled to rt and aqueous sodium bicarbonate solution (5 mL) and EtOAc (10 mL) were added. The aqueous layer was extracted with EtOAc (3×5 mL), then the organics were dried over MgSO$_4$ and concentrated under reduced pressure. The residue was purified via flash chromatography on silica gel (0-100% EtOAc/DCM then 0-10% MeOH/DCM). The fractions were concentrated then purified further via flash chromatography on silica gel (100% EtOAc) to give the title compound (0.335 g, 69%). LC/MS (Table A, Method a) R$_t$=2.07 min; MS m/z: 480 (M+H)$^+$. TNF IC$_{50}$=A The compounds shown in Table 1 were synthesized in a manner similar to Example #1 from 6-bromo-3-(2-(difluoromethoxy)phenyl)-2,3-dihydropyrazolo[1,2-a]indazol-9(1H)-one (Preparation #1) and the corresponding boronic acid/boronate. The corresponding enantiomers were separated by the chiral methods listed in Table B when applicable.

TABLE 1

| Boronic acid/boronate | Product | Example # | R$_t$ min (Table A, Method) | m/z ESI+ (M + H)$^+$ | Method for chiral separation/ Order of elution/Sign | TNF IC$_{50}$ |
|---|---|---|---|---|---|---|
| 4-(5-(4,4,5,5-Tetramethyl-1,3,2-dioxaborolan-2-yl)pyrimidin-2-yl)morpholine | | 1.1 | 2.07 (a) | 480 | 3/1$^{st}$/+ | A |
| 4-(5-(4,4,5,5-Tetramethyl-1,3,2-dioxaborolan-2-yl)pyrimidin-2-yl)morpholine | | 1.2 | 2.07 (a) | 480 | 3/2$^{nd}$/− | A |
| 1-(5-Boronopyrimidin-2-yl)piperidine-4-carboxylic acid (synthesized as described in WO2014009295A1) | | 1.3 | 1.86 (a) | 523 | NA | B |
| (R)-2-(2-(Methoxymethyl) pyrrolidin-1-yl)-5-(4,4,5,5-tetramethyl-1,3,2-dioxaborolan-2-yl)pyrimidine (Preparation #4) | | 1.4 | 2.31 (a) | 508 | 4/2$^{nd}$/NA | B |

TABLE 1-continued

| Boronic acid/boronate | Product | Example # | $R_t$ min (Table A, Method) | m/z ESI+ (M + H)+ | Method for chiral separation/ Order of elution/Sign | TNF IC$_{50}$ |
|---|---|---|---|---|---|---|
| (R)-2-(2-(Methoxymethyl)pyrrolidin-1-yl)-5-(4,4,5,5-tetramethyl-1,3,2-dioxaborolan-2-yl)pyrimidine (Preparation #4) | | 1.5 | 2.31 (a) | 508 | 4/1$^{st}$/NA | B |
| (R)-N-(Tetrahydrofuran-3-yl)-5-(4,4,5,5-tetramethyl-1,3,2-dioxaborolan-2-yl)pyrimidin-2-amine (Preparation #5) | | 1.6 | 1.80 (a) | 480 | 5/1$^{st}$/+ | B |
| (R)-N-(Tetrahydrofuran-3-yl)-5-(4,4,5,5-tetramethyl-1,3,2-dioxaborolan-2-yl)pyrimidin-2-amine (Preparation #5) | | 1.7 | 1.80 (a) | 480 | 5/2$^{nd}$/NA | B |

TABLE 1-continued

| Boronic acid/boronate | Product | Example # | R$_t$ min (Table A, Method) | m/z ESI+ (M + H)⁺ | Method for chiral separation/ Order of elution/Sign | TNF IC$_{50}$ |
|---|---|---|---|---|---|---|
| (R)-(2-(2-(Hydroxymethyl)morpholino)pyrimidin-5-yl)boronic acid (Preparation #6) | | 1.8 | 1.77 (a) | 510 | 1/1$^{st}$/+ | A |
| (R)-2-(2-(Hydroxymethyl)morpholino)pyrimidin-5-yl)boronic acid (Preparation #6) | | 1.9 | 1.77 (a) | 510 | 1/2$^{nd}$/− | A |

The compound shown in Table 2 were synthesized in a manner similar to Example #1 from (S)-6-bromo-3-(2-(difluoromethoxy)phenyl)-2,3-dihydropyrazolo[1,2-a]indazol-9(1H)-one (Preparation #2) and the corresponding boronic acid/boronate.

TABLE 2

| Boronic acid/boronate | Product | Example # | $R_t$ min (Table A, Method) | m/z ESI+ (M + H)+ | TNF IC$_{50}$ |
|---|---|---|---|---|---|
| (S)-(2-(2-(Hydroxymethyl)morpholino)pyrimidin-5-yl)boronic acid (synthesized from (S)-tert-butyl 2-(hydroxymethyl)morpholine-4-carboxylate using methods similar to Preparation #6) | | 2.1 | 1.77 (a) | 510 | A |

The compound shown in Table 3 were synthesized in a manner similar to Example #1 from (R)-6-bromo-3-(2-(difluoromethoxy)phenyl)-2,3-dihydropyrazolo[1,2-a]indazol-9(1H)-one (Preparation #3) and the corresponding boronic acid/boronate.

TABLE 3

| Boronic acid/boronate | Product | Example # | $R_t$ min (Table A, Method) | m/z ESI+ (M + H)+ | TNF IC$_{50}$ |
|---|---|---|---|---|---|
| (S)-(2-(2-(Hydroxymethyl)morpholino)pyrimidin-5-yl)boronic acid (synthesized from (S)-tert-butyl 2-(hydroxymethyl)morpholine-4-carboxylate using methods similar to Preparation #6) | | 3.1 | 1.77 (a) | 510 | A |

Example 4

(R)-3-(2-(Difluoromethoxy)phenyl)-6-(2-(2-hydroxypropan-2-yl)pyrimidin-5-yl)-2,3-dihydropyrazolo[1,2-a]indazol-9(1H)-one

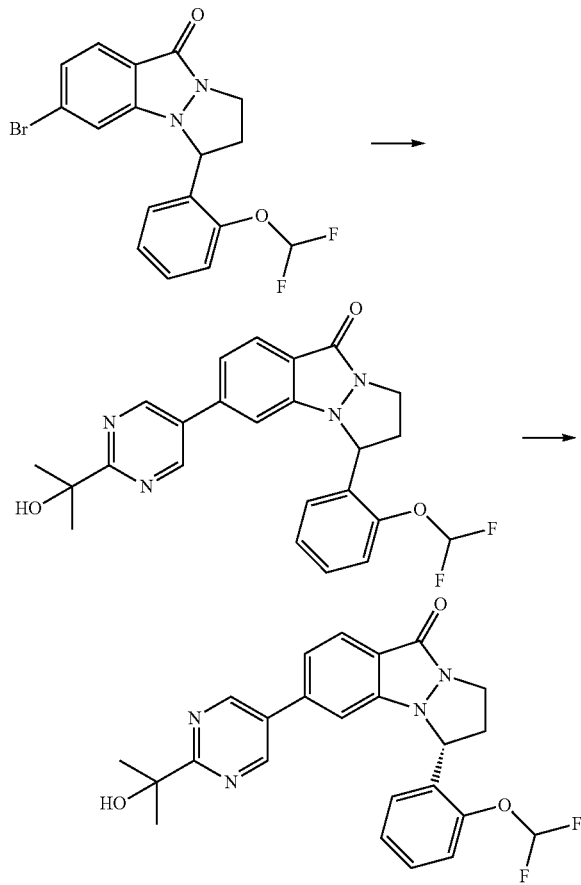

Step 1: 3-(2-(Difluoromethoxy)phenyl)-6-(2-(2-hydroxypropan-2-yl)pyrimidin-5-yl)-2,3-dihydropyrazolo[1,2-a]indazol-9(1H)-one 2-(5-Bromopyrimidin-2-yl)propan-2-ol (0.038 g, 0.177 mmol), 4,4,4',4',5,5,5',5'-octamethyl-2,2'-bi(1,3,2-dioxaborolane) (0.087 g, 0.342 mmol), potassium acetate (0.041 g, 0.418 mmol) and 1,4-dioxane (2 mL) were combined in a round flask under a $N_2$ atmosphere. The mixture was purged and flushed with $N_2$. $PdCl_2(dppf)$ (6.48 mg, 8.86 μmol) was added then the flask was once again purged and flushed with $N_2$ and then was heated to about 95° C. for about 90 min. The mixture was cooled to rt and then 6-bromo-3-(2-(difluoromethoxy)phenyl)-2,3-dihydropyrazolo[1,2-a]indazol-9(1H)-one (0.050 g, 0.127 mmol) (Preparation #1), water (0.500 mL), cesium carbonate (0.103 g, 0.316 mmol) and $Pd(Ph_3P)_4$ (0.0088 g, 0.0076 mmol) were added. After purging and flushing with $N_2$, the mixture was heated to about 100° C. for about 30 min. The mixture was cooled to rt, then water (10 mL) and DCM (10 mL) were added. The layers were separated then the aqueous portion was extracted with DCM (10 mL). The combined organics were dried over $MgSO_4$ filtered and concentrated under reduced pressure. The material was purified via flash chromatography on silica gel (0-100% EtOAc/DCM) to give the title compound (0.025, 44%); LC/MS (Table A, Method b) $R_t$=1.87 min; MS m/z: 453 $(M+H)^+$.

Step 2: (R)-3-(2-(Difluoromethoxy)phenyl)-6-(2-(2-hydroxypropan-2-yl)pyrimidin-5-yl)-2,3-dihydropyrazolo[1,2-a]indazol-9(1H)-one 3-(2-(Difluoromethoxy)phenyl)-6-(2-(2-hydroxypropan-2-yl)pyrimidin-5-yl)-2,3-dihydropyrazolo[1,2-a]indazol-9(1H)-one (0.051 g, 0.11 mmol) was submitted for chiral purification (Table B, Method 2). The first eluting fractions were concentrated to give the title compound (0.017 g, 30%) with undetermined optical rotation. LC/MS (Table A, Method a) $R_t$=1.85 min; MS m/z: 453 $(M+H)^+$.

The compounds shown in Table 4 were synthesized in a manner similar to Example #4 from 6-bromo-3-(2-(difluoromethoxy)phenyl)-2,3-dihydropyrazolo[1,2-a]indazol-9(1H)-one (Preparation #1) and the corresponding bromide. Enantiomers were separated by the chiral methods listed in Table B when applicable.

TABLE 4

| Bromide | Product | Example # | $R_t$ min (Table A, Method) | m/z ESI+ $(M + H)^+$ | Method for chiral separation/ Order of elution/Sign | TNF $IC_{50}$ |
|---|---|---|---|---|---|---|
| 2-(5-Bromopyrimidin-2-yl)propan-2-ol | (structure) | 4.1 | 1.85 (a) | 453 | 2/2$^{nd}$/− | B |

TABLE 4-continued

| Bromide | Product | Example # | R$_t$ min (Table A, Method) | m/z ESI+ (M + H)+ | Method for chiral separation/ Order of elution/Sign | TNF IC$_{50}$ |
|---|---|---|---|---|---|---|
| 1-(5-Bromopyrimidin-2-yl)piperidin-4-ol | | 4.2 | 1.82 (a) | 494 | NA | A |
| (S)-4-(((5-Bromo-pyrimidin-2-yl)amino)methyl)pyrrolidin-2-one (Preparation #12) | | 4.3 | 1.61 (b) | 507 | 9/2$^{nd}$/NA | B |
| (S)-4-(((5-Bromo-pyrimidin-2-yl)amino)methyl)pyrrolidin-2-one (Preparation #12) | | 4.4 | 1.61 (b) | 507 | 9/1$^{st}$/NA | A |
| (R)-4-(((5-Bromo-pyrimidin-2-yl)amino)methyl)pyrrolidin-2-one (Preparation #13) | | 4.5 | 1.62 (b) | 507 | 10/2$^{nd}$/NA | B |
| (R)-4-(((5-Bromo-pyrimidin-2-yl)amino)methyl)pyrrolidin-2-one (Preparation #13) | | 4.6 | 1.62 (b) | 507 | 10/1$^{st}$/NA | B |

TABLE 4-continued

| Bromide | Product | Example # | R$_t$ min (Table A, Method) | m/z ESI+ (M + H)+ | Method for chiral separation/ Order of elution/Sign | TNF IC$_{50}$ |
|---|---|---|---|---|---|---|
| 7-(5-Bromo-pyrimidin-2-yl)-7-azaspiro[3.5]nonan-2-ol (synthesized from 7-azaspiro[3.5]nonan-2-ol, Hydrochloric Acid and 5-bromo-2-chloropyrimidine using methods similar to Preparation #10) | | 4.7 | 2.09 (b) | 534 | 11/1$^{st}$/NA | A |
| 7-(5-Bromopyrimidin-2-yl)-7-azaspiro[3.5]nonan-2-ol (synthesized from 7-azaspiro[3.5]nonan-2-ol, Hydrochloric Acid and 5-bromo-2-chloropyrimidine using methods similar to Preparation #10) | | 4.8 | 2.09 (b) | 534 | 11/2$^{nd}$/NA | A |

The compounds shown in Table 5 were synthesized in a manner similar to Example #4 from (S)-6-bromo-3-(2-(difluoromethoxy)phenyl)-2,3-dihydropyrazolo[1,2-a]indazol-9(1H)-one (Preparation #2) and the corresponding bromide.

TABLE 5

| Bromide | Product | Example # | R$_t$ min (Table A, Method) | m/z ESI+ (M + H)+ | Optical Rotation | TNF IC$_{50}$ |
|---|---|---|---|---|---|---|
| (S)-7-(5-Bromopyrimidin-2-yl)hexahydroimidazo[1,5-a]pyrazin-3(2H)-one (Preparation #8) | | 5.1 | 1.72 (a) | 534 | — | A |

TABLE 5-continued

| Bromide | Product | Example # | R$_t$ min (Table A, Method) | m/z ESI+ (M + H)$^+$ | Optical Rotation | TNF IC$_{50}$ |
|---|---|---|---|---|---|---|
| (R)-7-(5-Bromopyrimidin-2-yl)hexahydroimidazo[1,5-a]pyrazin-3(2H)-one (Preparation #9) | | 5.2 | 1.72 (a) | 534 | — | A |

The compounds shown in Table 6 were synthesized in a manner similar to Example #4 from (R)-6-bromo-3-(2-(difluoromethoxy)phenyl)-2,3-dihydropyrazolo[1,2-a]indazol-9(1H)-one (Preparation #3) and the corresponding bromide.

TABLE 6

| Bromide | Product | Example # | R$_t$ min (Table A, Method) | m/z ESI+ (M + H)$^+$ | Optical Rotation | TNF IC$_{50}$ |
|---|---|---|---|---|---|---|
| (S)-7-(5-Bromopyrimidin-2-yl)hexahydroimidazo[1,5-a]pyrazin-3(2H)-one (Preparation #8) | | 6.1 | 1.72 (a) | 534 | + | A |
| (R)-7-(5-Bromopyrimidin-2-yl)hexahydroimidazo[1,5-a]pyrazin-3(2H)-one (Preparation #9) | | 6.2 | 1.72 (a) | 534 | NA | A |

TABLE 6-continued

| Bromide | Product | Example # | R$_t$ min (Table A, Method) | m/z ESI+ (M + H)$^+$ | Optical Rotation | TNF IC$_{50}$ |
|---|---|---|---|---|---|---|
| (R)-1-(4-(5-Bromopyrimidin-2-yl)-2-methylpiperazin-1-yl)ethanone (Preparation #25) | 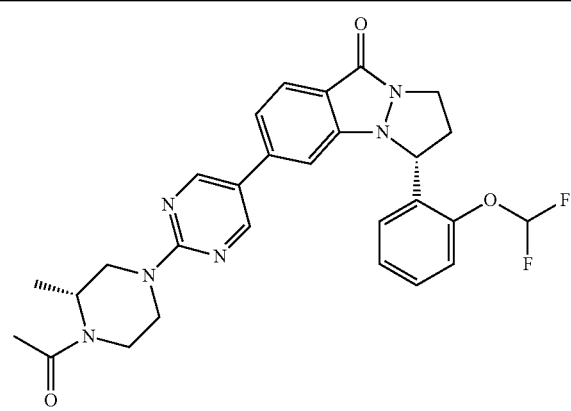 | 6.3 | 1.85 (a) | 535 | NA | A |
| (R)-1-(4-(5-Bromopyrimidin-2-yl)-2-methylpiperazin-1-yl)-2-hydroxyethanone (Preparation #26) | 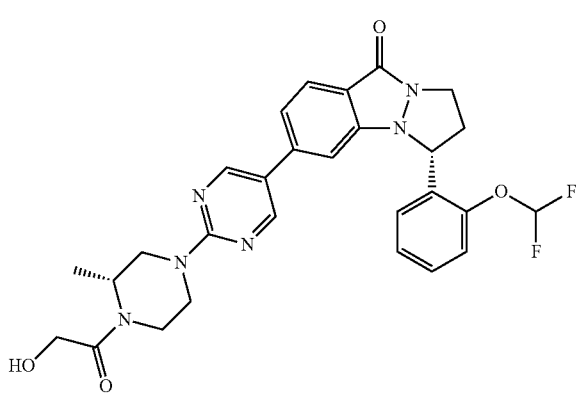 [SMILES: C[C@@H]1CN(c2ncc(-c3ccc4c(=O)n5n(c4c3)[C@@H](c3ccccc3OC(F)F)CC5)cn2)CCN1C(=O)CO] | 6.4 | 1.77 (a) | 551 | NA | A |
| (R)-1-(4-(5-Bromopyrimidin-2-yl)-3-methylpiperazin-1-yl)ethanone (synthesized in a manner similar to Preparation #25 from 5-bromo-2-chloropyrimidine and (R)-tert-butyl 3-methylpiperazine-1-carboxylate) | 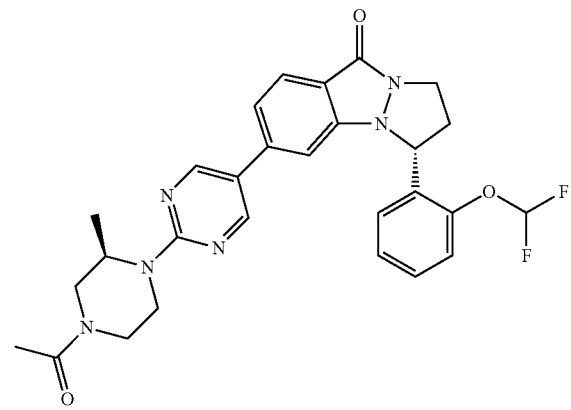 [SMILES: CC(=O)N1CCN(c2ncc(-c3ccc4c(=O)n5n(c4c3)[C@@H](c3ccccc3OC(F)F)CC5)cn2)[C@H](C)C1] | 6.5 | 2.00 (b) | 535 | NA | A |
| 2-(5-Bromo-4-methylpyrimidin-2-yl)propan-2-ol (synthesized as described in WO2015/86506A1) | 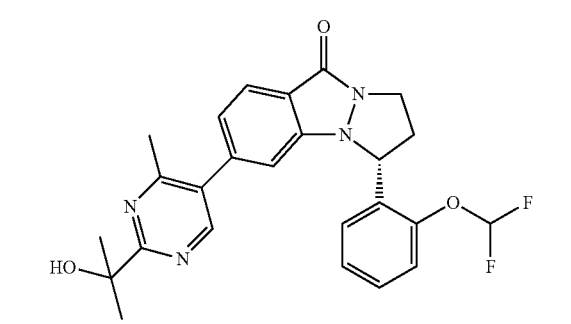 [SMILES: Cc1nc(C(C)(C)O)ncc1-c1ccc2c(=O)n3n(c2c1)[C@@H](c1ccccc1OC(F)F)CC3] | 6.6 | 1.92 (a) | 467 | NA | A |

Example 7

(R)-3-(2-(Difluoromethoxy)phenyl)-6-(2-((3-methoxypropyl)amino)pyrimidin-5-yl)-2,3-dihydropyrazolo[1,2-a]indazol-9(1H)-one

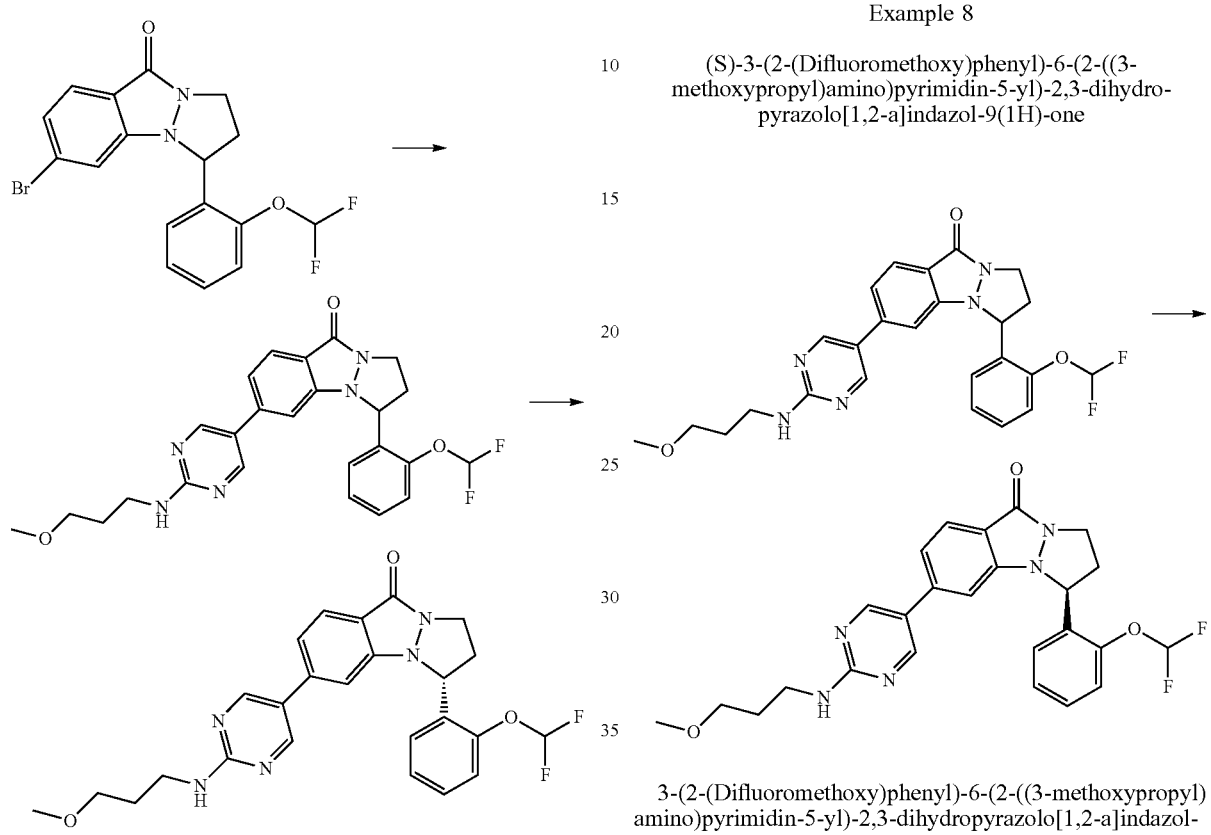

Step 1: 3-(2-(Difluoromethoxy)phenyl)-6-(2-((3-methoxypropyl)amino)pyrimidin-5-yl)-2,3-dihydropyrazolo[1,2-a]indazol-9(1H)-one To a solution of (2-((3-methoxypropyl)amino)pyrimidin-5-yl)boronic acid (0.187 g, 0.886 mmol) (synthesized from 3-methoxypropan-1-amine and 5-bromo-2-chloropyrimidine using methods similar to Preparation #6 step 2 in EtOH (2 mL) was added 6-bromo-3-(2-(difluoromethoxy)phenyl)-2,3-dihydropyrazolo[1,2-a]indazol-9(1H)-one (0.050 g, 0.127 mmol) (Preparation #1) followed by Cs₂CO₃ (0.124 g, 0.380 mmol) and SiliaCat® DPP-Pd (0.053 g, 0.013 mmol). Under an atmosphere of N₂, the mixture was heated to about 90° C. for about 45 min. The reaction mixture was cooled to rt and the catalyst was filtered off and rinsed with excess MeOH. The filtrate was concentrated under reduced pressure and the residue was purified via flash chromatography on silica gel (50-1000/% EtOAc/DCM then 0-7% MeOH/DCM) to give the title compound (0.053 g, 87%); LC/MS (Table A, Method b) R$_t$=1.95 min; MS m/z: 482 (M+H)$^+$.

Step 2: (R)-3-(2-(Difluoromethoxy)phenyl)-6-(2-((3-methoxypropyl)amino)pyrimidin-5-yl)-2,3-dihydropyrazolo[1,2-a]indazol-9(1H)-one 3-(2-(Difluoromethoxy)phenyl)-6-(2-((3-methoxypropyl)amino)pyrimidin-5-yl)-2,3-dihydropyrazolo[1,2-a]indazol-9(1H)-one (0.085 g, 0.177 mmol) was submitted for chiral purification (Table B, Method 6). Fractions from the first eluting component were combined and concentrated under reduced pressure then taken into water, frozen and lyophilized to give the title compound (0.029 g, 34%) with positive (+) optical rotation. LC/MS (Table A, Method a) R$_t$=1.92 min; MS m/z: 482 (M+H)$^+$.

Example 8

(S)-3-(2-(Difluoromethoxy)phenyl)-6-(2-((3-methoxypropyl)amino)pyrimidin-5-yl)-2,3-dihydropyrazolo[1,2-a]indazol-9(1H)-one 3-(2-(Difluoromethoxy)phenyl)-6-(2-((3-methoxypropyl)amino)pyrimidin-5-yl)-2,3-dihydropyrazolo[1,2-a]indazol-9(1H)-one (0.085 g, 0.177 mmol) (Example 7, step 1) was submitted for chiral purification (Table B, Method 6). Fractions from the second eluting component were combined and concentrated under reduced pressure then taken into water, frozen and lyophilized to give the title compound (0.028 g, 33%) with negative (−) optical rotation. LC/MS (Table A, Method a) R$_t$=1.92 min; MS m/z: 482 (M+H)$^+$.

Example 9

(S)-6-(2-(4-Acetylpiperazin-1-yl)pyrimidin-5-yl)-3-(2-(difluoromethoxy)phenyl)-2,3-dihydropyrazolo[1,2-a]indazol-9(1H)-one

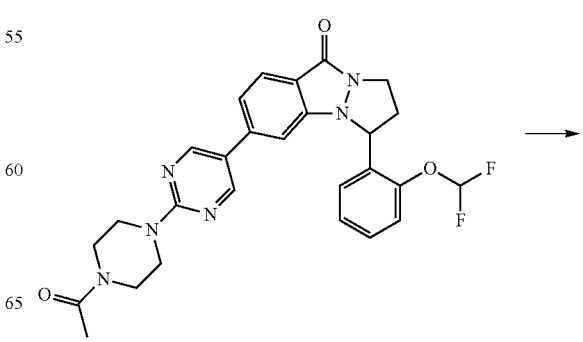

87

-continued

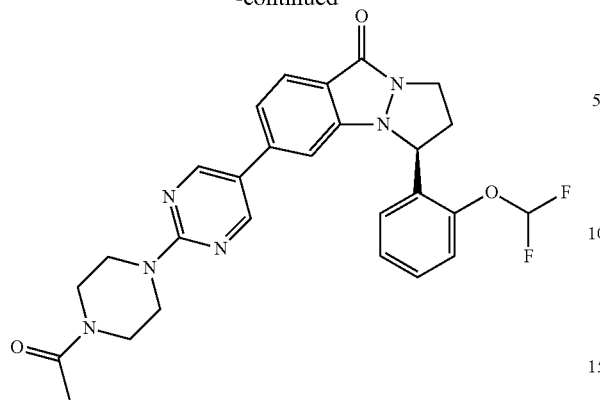

6-(2-(4-Acetylpiperazin-1-yl)pyrimidin-5-yl)-3-(2-(difluoromethoxy)phenyl)-2,3-dihydropyrazolo[1,2-a]indazol-9(1H)-one (0.095 g, 0.18 mmol) (Preparation #14) was submitted for chiral purification (Table B, Method 13). Fractions from the first eluting component were combined and concentrated under reduced pressure then dried in a vacuum oven at about 65° C. for about 24 h to give the title compound (0.038 g, 35%), optical rotation (NA); LC/MS (Table A, Method b) $R_t$=1.89 min; MS m/z: 521 (M+H)$^+$.

Example 10

(R)-6-(2-(4-Acetylpiperazin-1-yl)pyrimidin-5-yl)-3-(2-(difluoromethoxy)phenyl)-2,3-dihydropyrazolo[1,2-a]indazol-9(1H)-one

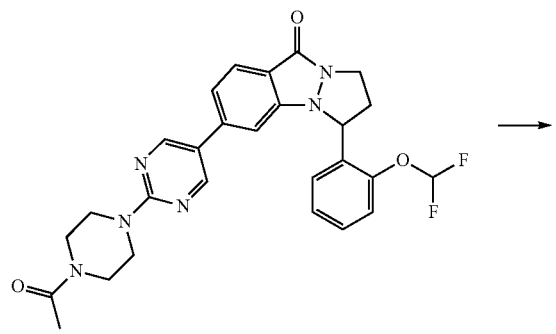

88

-continued

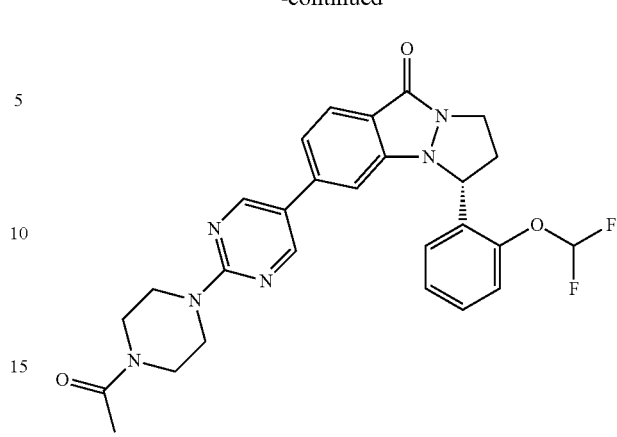

6-(2-(4-Acetylpiperazin-1-yl)pyrimidin-5-yl)-3-(2-(difluoromethoxy)phenyl)-2,3-dihydropyrazolo[1,2-a]indazol-9(1H)-one (Preparation #14) was submitted for chiral purification (Table B, Method 13). Fractions from the second eluting component were combined and concentrated under reduced pressure then dried in a vacuum oven at about 65° C. for about 24 h to give the title compound (0.032 g, 31%), optical rotation (NA); LC/MS (Table A, Method b) $R_t$=1.89 min; MS m/z: 521 (M+H)$^+$.

The compounds shown in Table 7 were synthesized in a manner similar to Example #1, step 1 from 3-bromo-6-(2-(difluoromethoxy)phenyl)-8,9-dihydro-6H-pyridazino[1,2-a]indazol-11(7H)-one (Preparation #15) and the corresponding boronic acid/boronate.

TABLE 7

| Boronic acid/boronate | Product | Example # | $R_t$ min (Table A, Method) | m/z ESI+ (M + H)$^+$ | TNF IC$_{50}$ |
|---|---|---|---|---|---|
| 2-(4-Morpholino)pyrimidine-5-boronic acid pinacol ester | 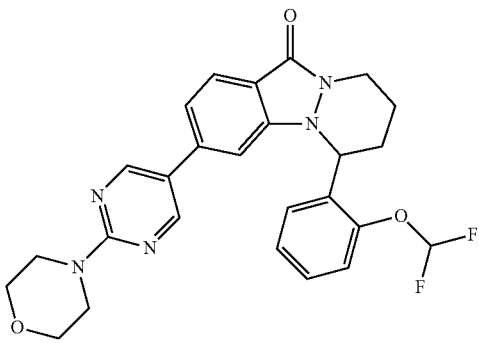 [SMILES: O=c1c2ccc(-c3cnc(N4CCOCC4)nc3)cc2n2n1CCCC2c1ccccc1OC(F)F] | 7.1 | 2.19 (a) | 494 | A |

TABLE 7-continued

| Boronic acid/boronate | Product | Example # | R, min (Table A, Method) | m/z ESI+ (M + H)+ | TNF IC50 |
|---|---|---|---|---|---|
| 1-(5-(4,4,5,5-Tetramethyl-1,3,2-dioxaborolan-2-yl)pyrimidin-2-yl)piperidin-4-ol (0.102 g, 0.334 mmol) (synthesized from 1-(5-bromopyrimidin-2-yl)piperidin-4-ol using methods similar to Preparation #4) | | 7.2 | 1.93 (a) | 508 | B |

Example 11

6-(2-(Difluoromethoxy)phenyl)-3-(2-(1,1-dioxidothiomorpholino)pyrimidin-5-yl)-8,9-dihydro-6H-pyridazino[1,2-a]indazol-11(7H)-one A mixture of 6-(2-(difluoromethoxy)phenyl)-3-(2-thiomorpholinopyrimidin-5-yl)-8,9-dihydro-6H-pyridazino[1,2-a]indazol-11(7H)-one (0.118 g, 0.208 mmol) (Preparation #16) in DCM (2 mL) was cooled in an ice water bath for about 5 min, after which m-CPBA (~77%) (0.085 g, 0.38 mmol) was added in one portion. The resulting solution was allowed to stir at about 0° C. for about 30 min. The reaction mixture was partitioned between DCM (20 mL) and saturated aqueous NaHCO3 (20 mL). After separating the layers, the aqueous phase was extracted with DCM (3×5 mL). The combined organic phases were washed with saturated aqueous NaCl (10 mL), dried over Na2SO4, filtered, and concentrated under reduced pressure. The resulting solid was triturated with DCM (3 mL), isolated by vacuum filtration and air dried to give the title compound (0.057 g, 50%); LC/MS (Table A, Method a) Rf=2.01 min; MS m/z: 542 (M+H)+.

Example 12

3-(2-Methoxyphenyl)-6-(2-morpholinopyrimidin-5-yl)-2,3-dihydropyrazolo[1,2-a]indazol-9(1H)-one

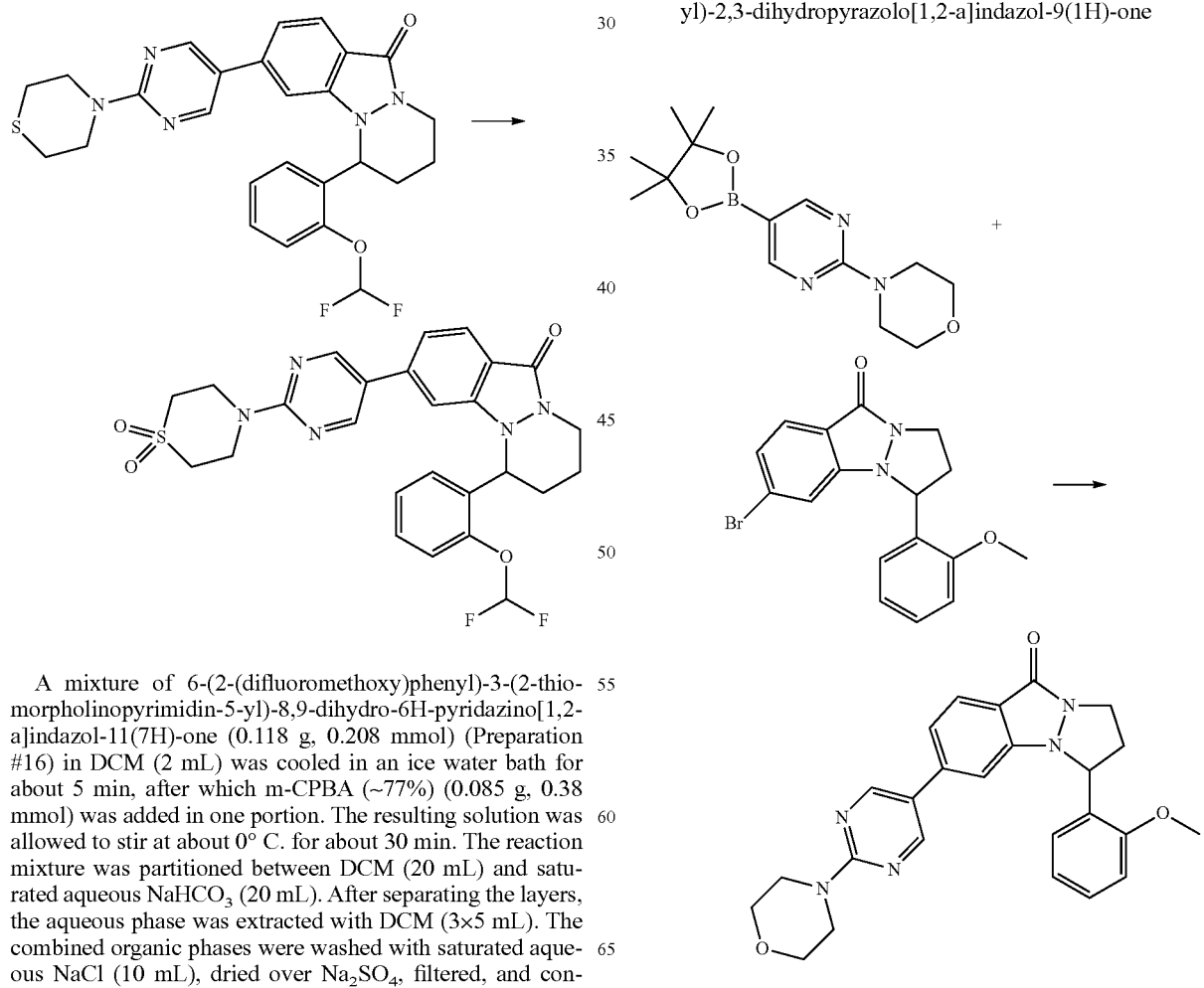

A mixture of 2-(4-morpholino)pyrimidine-5-boronic acid pinacol ester (0.063 g, 0.217 mmol), 6-bromo-3-(2-methoxyphenyl)-2,3-dihydropyrazolo[1,2-a]indazol-9(1H)-one (0.052 g, 0.145 mmol) (Preparation #17), Pd(Ph₃P)₄ (0.017 g, 0.014 mmol), and cesium carbonate (0.141 g, 0.434 mmol) in 1,4-dioxane (1.2 mL)/water (0.3 mL) was heated at reflux for about 12 min. After cooling, the reaction mixture was partitioned between EtOAc (5 mL) and water (5 mL). The layers were separated and the aqueous phase was extracted with EtOAc (2×2 mL). The combined organics were washed with saturated aqueous NaCl (5 mL), dried over Na₂SO₄, filtered, and concentrated under reduced pressure. The material was purified via flash chromatography on silica gel (0-50% of 1:9 MeOH:EtOAc/DCM) to give the title compound (0.056 g, 87%); LC/MS (Table A, Method a) $R_t$=2.03 min; MS m/z: 444 (M+H)⁺.

Example 13

(R)-6-(2-(2-Hydroxypropan-2-yl)pyrimidin-5-yl)-3-(2-methoxyphenyl)-2,3-dihydropyrazolo[1,2-a]indazol-9(1H)-one

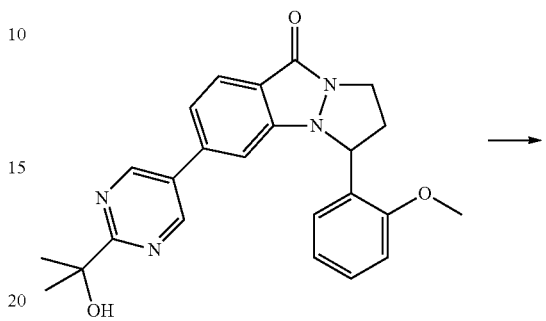

6-(2-(2-Hydroxypropan-2-yl)pyrimidin-5-yl)-3-(2-methoxyphenyl)-2,3-dihydropyrazolo[1,2-a]indazol-9(1H)-one (0.080 g, 0.19 mmol) (Preparation #14) was submitted for chiral purification (Table B, Method 18). Fractions from the first eluting component were combined and concentrated under reduced pressure to give the title compound (0.030 g, 34%) with positive (+) optical rotation. LC/MS (Table A, Method a) $R_t$=1.81 min; MS m/z: 417 (M+H)⁺.

Example #14

(S)-6-(2-(2-Hydroxypropan-2-yl)pyrimidin-5-yl)-3-(2-methoxyphenyl)-2,3-dihydropyrazolo[1,2-a]indazol-9(1H)-one

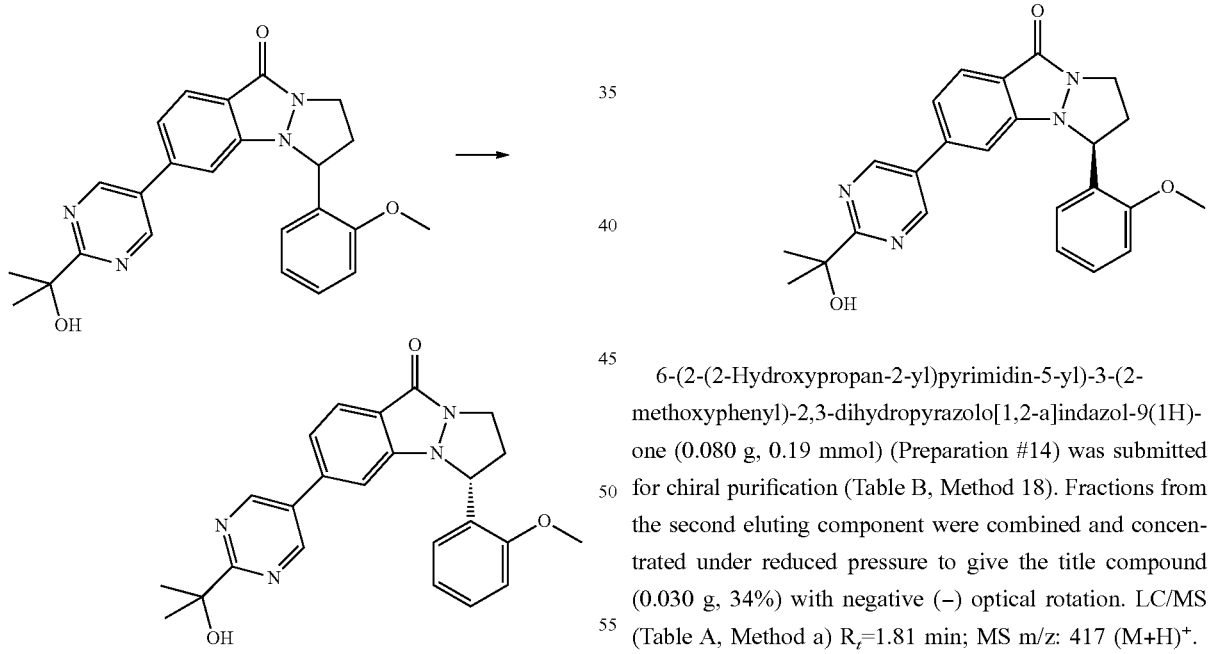

6-(2-(2-Hydroxypropan-2-yl)pyrimidin-5-yl)-3-(2-methoxyphenyl)-2,3-dihydropyrazolo[1,2-a]indazol-9(1H)-one (0.080 g, 0.19 mmol) (Preparation #14) was submitted for chiral purification (Table B, Method 18). Fractions from the second eluting component were combined and concentrated under reduced pressure to give the title compound (0.030 g, 34%) with negative (−) optical rotation. LC/MS (Table A, Method a) $R_t$=1.81 min; MS m/z: 417 (M+H)⁺.

The compounds shown in Table 8 were synthesized in a manner similar to Example #1, step 1 from a 3-bromo-6-(2-(aryl)-8,9-dihydro-6H-pyridazino[1,2-a]indazol-11(7H)-one or bromo-6-(2-(heteroaryl)-8,9-dihydro-6H-pyridazino[1,2-a]indazol-11(7H)-one (Prepared from the appropriate halide and 6-bromo-1H-indazol-3(2H)-one in a manner similar to Preparation 1, steps 3 through 5) and 2-(4-morpholino)pyrimidine-5-boronic acid pinacol ester.

TABLE 8

| Halide | Product | Example # | R$_t$ min (Table A, Method) | m/z ESI+ (M + H)$^+$ | TNF IC$_{50}$ |
| --- | --- | --- | --- | --- | --- |
| 2-(1-Chlorobut-3-en-1-yl)-6-methylbenzonitrile (synthesized from Preparation #19 using methods similar to Preparation #17, Step 2) | | 8.1 | 1.96 (a) | 453 | B |
| (1-Bromobut-3-en-1-yl)benzene (synthesized from benzaldehyde using methods similar to Preparation #1, Steps 1 and 2) | | 8.2 | 1.98 (a) | 414 | B |
| 3-(1-Bromobut-3-en-1-yl)-4-methoxybenzonitrile (synthesized from 3-formyl-4-methoxybenzonitrile (synthesized from 5-bromo-2-methoxybenzaldehyde as described in Tetrahedron Letters, 46(11), 1815-1818, 2005) using methods similar to Preparation #19, Step 4 and Preparation #1, Step 2) | | 8.3 | 1.85 (a) | 469 | B |
| 3-(1-Bromobut-3-en-1-yl)-2-methoxybenzonitrile (synthesized from 3-formyl-2-methoxybenzonitrile (synthesized from 3-bromo-2-methoxybenzaldehyde as described in Tetrahedron Letters, 46(11), 1815-1818, 2005) using methods similar to Preparation #19, Step 4 and Preparation #1, Step 2) | | 8.4 | 1.92 (a) | 469 | B |

TABLE 8-continued

| Halide | Product | Example # | R$_t$ min (Table A, Method) | m/z ESI+ (M + H)+ | TNF IC$_{50}$ |
|---|---|---|---|---|---|
| 5-(1-Bromobut-3-en-1-yl)-1-isopropyl-1H-pyrazole (synthesized from 1-isopropyl-1H-pyrazole-5-carbaldehyde using methods similar to Preparation #1, Steps 1 and 2) | | 8.5 | 1.68 (a) | 446 | C |

Example #15

2-Methyl-6-(6-(2-morpholinopyrimidin-5-yl)-9-oxo-1,2,3,9-tetrahydropyrazolo[1,2-a]indazol-3-yl)benzamide A flask was charged with 2-methyl-6-(6-(2-morpholinopyrimidin-5-yl)-9-oxo-1,2,3,9-tetrahydropyrazolo[1,2-a]indazol-3-yl)benzonitrile (0.050 g, 0.11 mmol) (Example #8.1), sodium hydroxide (32 wt % in water, 0.138 g, 1.11 mmol), MeOH (1.0 mL) and water (1.0 mL).

After about 20 h at about 90° C., the reaction mixture was cooled to ambient temperature and then partitioned between saturated aqueous NaHCO$_3$ (5 mL) and DCM (50 mL). The aqueous phase was extracted with EtOAc (30 mL). The combined organics were concentrated under reduced pressure. The residue was dissolved in 10% MeOH/DCM (50 mL). The solution was dried over MgSO$_4$, filtered, and concentrated under reduced pressure. The residue was purified via flash chromatography on silica gel (1-10% MeOH/DCM) to give the title compound (0.018 g, 34%); LC/MS (Table A, Method a) R$_t$=1.62 min; MS m/z: 471 (M+H)+.

Example 16 rac-(1R,9bR)-1-(2-(Difluoromethoxy)phenyl)-8-(2-morpholinopyrimidin-5-yl)-2,3-dihydro-1H-pyrrolo[2,1-a]isoindol-5(9bH)-one

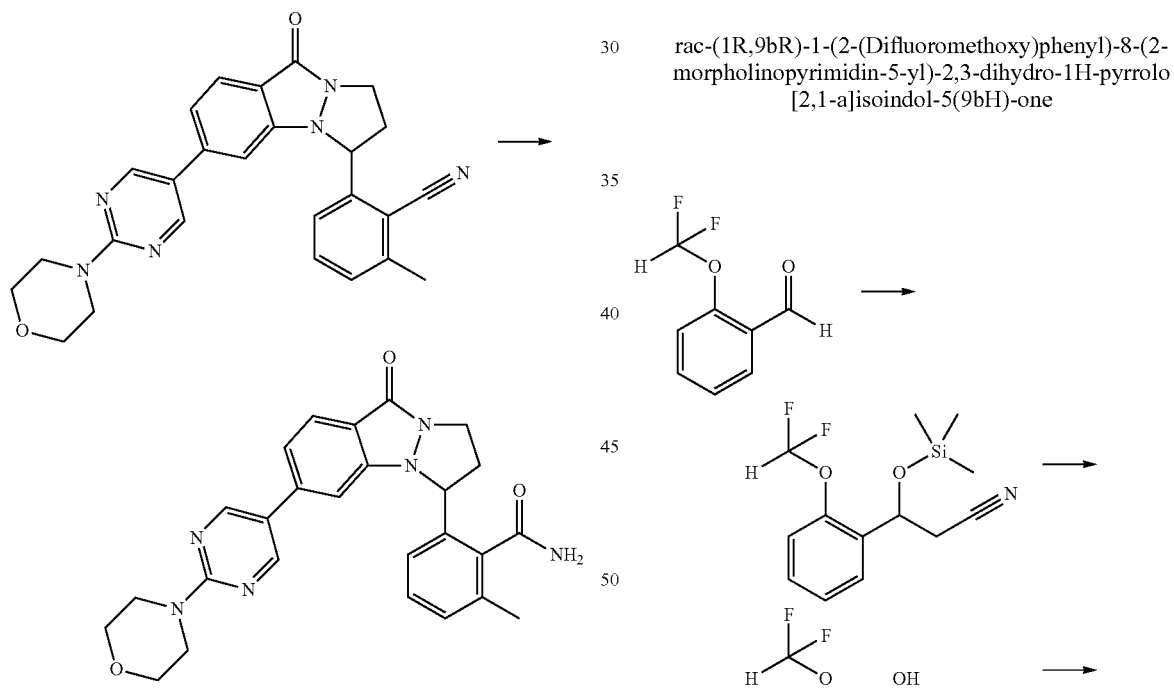

-continued

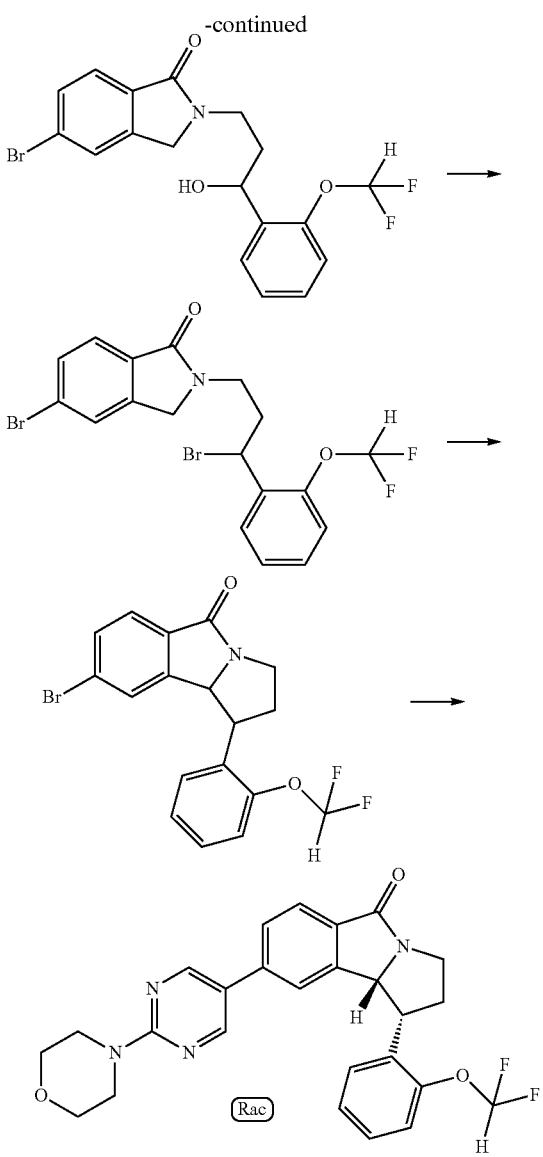

Step 1: 3-(2-(Difluoromethoxy)phenyl)-3-((trimethylsilyl)oxy)propanenitrile

A flask was charged with tris(2,4,6-trimethoxyphenyl) phosphine (0.310 g, 0.582 mmol), 2-(difluoromethoxy)benzaldehyde (1.00 g, 5.81 mmol) and 2-(trimethylsilyl)acetonitrile (0.905 g, 7.99 mmol). The mixture was warmed to about 60° C. for about 14 h. The mixture was cooled to rt then diluted with water (50 mL) and extracted with EtOAc (2×25 mL). The combined organics were washed with saturated aqueous NaCl, dried over MgSO$_4$, filtered and concentrated under reduced pressure. The material was purified via flash chromatography on silica gel 75:25 heptane/EtOAc) to give the title compound (1.48 g, 89%); LC/MS (Table A, Method b) R$_f$=2.63 min; MS m/z: 286 (M+H)$^+$ Step 2: 3-(2-(Difluoromethoxy)phenyl)-3-hydroxypropanenitrile A flask was charged with MeOH (25 mL) then hydrogen chloride gas was bubbled into the solution for about 5 min. The solution was added to 3-(2-(difluoromethoxy)phenyl)-3-((trimethylsilyl)oxy)propanenitrile (1.46 g, 5.12 mmol) then the mixture was stirred for about 30 min. The mixture was concentrated on under reduced pressure then the material was purified via flash chromatography on silica gel (0-40% EtOAc/DCM) to give the title compound (1.05 g, 96%); $^1$H NMR (400 MHz, DMSO-d$_6$) δ 7.61 (dd, J=7.7, 1.8 Hz, 1H), 7.42-6.99 (m, 4H), 6.02 (d, J=4.6 Hz, 1H), 5.14-5.09 (m, 1H), 2.92-2.72 (m, 2H).

Step 3:
3-Amino-1-(2-(difluoromethoxy)phenyl)propan-1-ol

A flask was charged with THF (12 mL) and lithium aluminum hydride (0.411 g, 10.8 mmol). The mixture was cooled to about 0° C. then 3-(2-(difluoromethoxy)phenyl)-3-hydroxypropanenitrile (1.05 g, 4.93 mmol) in THF (12 mL) was added over about 20 min keeping the internal temperature of the mixture between about 0° C. and 5° C. After complete addition the mixture was stirred at about 0° C. for about 15 min then the mixture was allowed to warm to rt. After about 1 h the mixture was diluted with THF (10 mL) then sodium sulfate decahydrate (3.0 g, 9.3 mmol) was added slowly. The mixture was stirred for about 6 h then sodium sulfate decahydrate (1.0 g, 3.1 mmol) was added. The mixture was stirred for about 12 h then filtered through a bed of Celite® and the pad was washed with EtOAc (25 mL). The filtrate was concentrated under reduced pressure to give the title compound (0.868 g, 81%); LC/MS (Table A, Method b) R$_f$=0.99 min; MS m/z: 218 (M+H)$^+$ Step 4: 5-Bromo-2-(3-(2-(difluoromethoxy)phenyl)-3-hydroxypropyl)isoindolin-1-one A flask was charged with 3-amino-1-(2-(difluoromethoxy)phenyl)propan-1-ol (0.77 g, 3.5 mmol), McOH (15 mL), methyl 4-bromo-2-(bromomethyl)benzoate (0.863 g, 2.80 mmol) and DIEA (0.538 mL, 3.08 mmol). The mixture was warmed to about 75° C. for about 3 h then cooled to rt and concentrated under reduced pressure. The material was partitioned between EtOAc (25 mL) water (25 mL). Hydrochloric acid (1 N) was added until the aqueous layer was acidic by pH paper. The organic layer was washed with saturated aqueous NaCl, dried over MgSO$_4$, filtered and the filtrate concentrated under reduced pressure. The residue was purified via flash chromatography on silica gel (0-30% EtOAc/DCM). The appropriate fractions were collected and concentrated under reduced pressure to give the title compound (0.807 g, 70%); LC/MS (Table A, Method b) R$_f$=2.24 min; MS m/z: 412, 414 (M+H)$^+$ Step 5: 5-Bromo-2-(3-bromo-3-(2-(difluoromethoxy)phenyl)propyl)isoindolin-1-one A flask was charged with 5-bromo-2-(3-(2-(difluoromethoxy)phenyl)-3-hydroxypropyl)isoindolin-1-one (0.375 g, 0.910 mmol), DCM (9 mL) and tribromophosphine (1 M in DCM) (1.0 mL, 1.0 mmol). The mixture was stirred for about 1 h then water (2 mL) was added and the mixture was then stirred for about 30 min. The mixture was diluted with DCM (25 mL) then cooled to about 0° C. and basified with saturated aqueous sodium bicarbonate. The organic layer was washed with saturated aqueous NaCl, dried over MgSO$_4$, filtered and the filtrate concentrated under reduced pressure to give the title compound (0.328 g, 76%); LC/MS (Table A, Method b) R$_f$=2.51 min; MS m/z: 474, 476, 478 (M+H)$^+$ Step 6: 8-Bromo-1-(2-(difluoromethoxy)phenyl)-2,3-dihydro-1H-pyrrolo[2,1-a]isoindol-5(9bH)-one A flask under nitrogen was charged with 5-bromo-2-(3-bromo-3-(2-(difluoromethoxy)phenyl)propyl)isoindolin-1-one (0.37 g, 0.78 mmol) and THF (8 mL). The mixture was cooled to about −70° C. then LiHMDS (1M in THF) (0.9 mL, 0.9 mmol) was added over about 5 min. After about 45 min acetic acid (0.2 mL) was added. The mixture was warmed to rt then concentrated under reduced pressure. The material was partitioned between EtOAc (20 mL) and water (10 mL) then the organic layer was washed with saturated aqueous NaCl, dried over MgSO$_4$, filtered and the filtrate concentrated under reduced pressure. The residue was purified via flash chromatography on silica gel (0-20% EtOAc/DCM). The appropriate fractions were collected and concentrated under reduced pressure to give the title compound as an approximately 1:1 mixture of diastereomers; (0.092 g, 30%); LC/MS (Table A, Method b) R$_t$=2.29, 2.38 min; MS m/z: 394, 396 (M+H)$^+$ Step 7: rac-(1R,9bR)-1-(2-(Difluoromethoxy)phenyl)-8-(2-morpholinopyrimidin-5-yl)-2,3-dihydro-1H-pyrrolo[2,1-a]isoindol-5(9bH)-one A flask under nitrogen was charged with 8-bromo-1-(2-(difluoromethoxy)phenyl)-2,3-dihydro-1H-pyrrolo[2,1-a]isoindol-5(9bH)-one (0.090 g, 0.228 mmol) as an approximately 1:1 mixture of diastereomers, 1,4-dioxane (4 mL) and water (1 mL), 4-(5-(4,4,5,5-tetramethyl-1,3,2-dioxaborolan-2-yl)pyrimidin-2-yl)morpholine (0.073 g, 0.251 mmol), cesium carbonate (0.149 g, 0.457 mmol) and PdCl$_2$(PPh$_3$)$_2$ (0.011 g, 0.016 mmol). The mixture was heated to about 85° C. for about 45 min. The mixture was cooled to rt then concentrated under reduced pressure. The material was purified by preparative reverse phase chromatography (Table C, Method 1). The shorter R$_t$ compound fraction was lyophilized to give the title compound (0.0206 g, 19%); LC/MS (Table A, Method a) R$_t$=2.20 min; MS m/z: 479 (M+H)$^+$ Example 17 rac-(1R,9bS)-1-(2-(Difluoromethoxy)phenyl)-8-(2-morpholinopyrimidin-5-yl)-2,3-dihydro-1H-pyrrolo[2,1-a]isoindol-5(9bH)-one

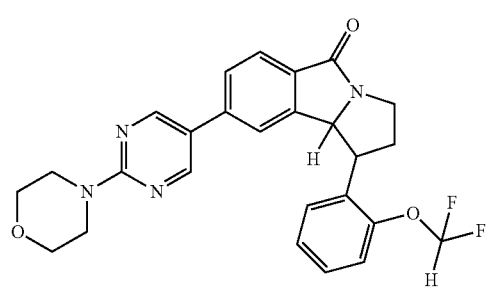

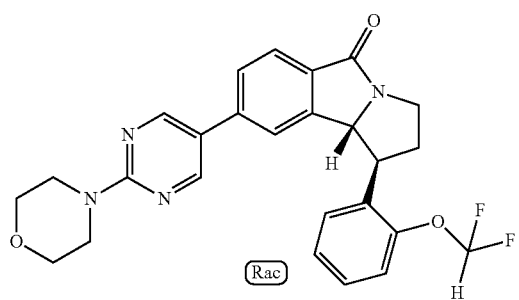

The material from Example 16, Step 7 was purified by preparative reverse phase chromatography (Table C, method 1). The longer R$_t$ compound fraction was lyophilized to give the title compound (0.0237 g, 22%); LC/MS (Table A, Method a) R$_t$=2.29 min; MS m/z: 479 (M+H)$^+$ Example #18 rac-(1R,10bR)-1-(2-(Difluoromethoxy)phenyl)-9-(2-morpholinopyrimidin-5-yl)-3,4-dihydro-1H-[1,4]oxazino[3,4-a]isoindol-6(10bH)-one

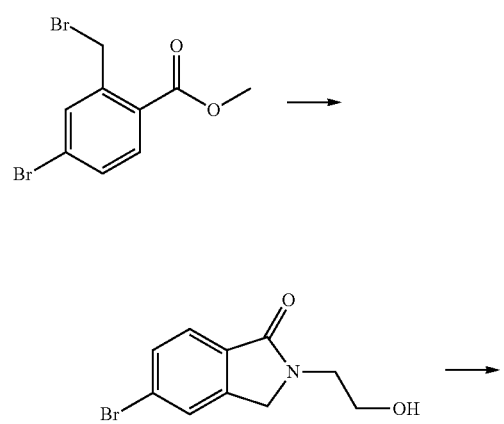

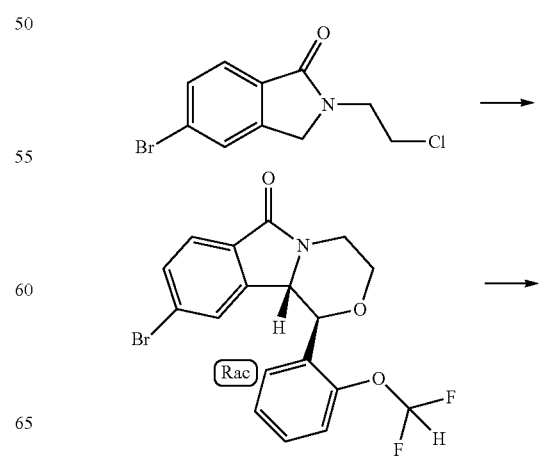

-continued

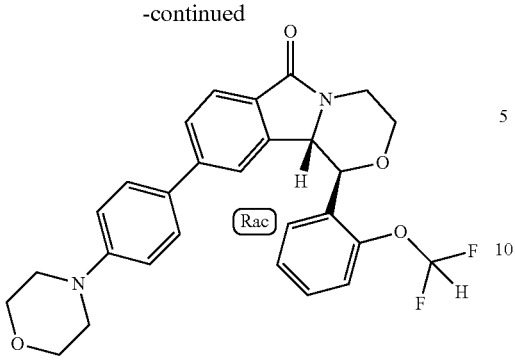

Step 1:
5-Bromo-2-(2-hydroxyethyl)isoindolin-1-one

A flask was charged with 2-aminoethanol (2.31 g, 37.8 mmol), MeOH (75 mL), DIEA (2.80 mL, 16.1 mmol) and methyl 4-bromo-2-(bromomethyl)benzoate (2.0 g, 6.5 mmol). The mixture was warmed in an oil bath heated to about 75° C. After about 90 min, the mixture was cooled to rt then concentrated under reduced pressure. Water (50 mL) was added then the mixture was concentrated at a pressure of about 50 mbar and a bath temperature of about 40° C. to remove volatiles. The solids formed were collected by filtration then washed with water (10 mL). The collected solids were dried to give the title compound (2.73 g, 85%); LC/MS (Table A, Method b) $R_t$=1.46 min; MS m/z: 256, 258 (M+H)$^+$

Step 2: 5-Bromo-2-(2-chloroethyl)isoindolin-1-one

A flask was charged with 5-bromo-2-(2-hydroxyethyl)isoindolin-1-one (2.73 g, 10.7 mmol), DCM (50 mL) and thionyl chloride (1.00 mL, 13.6 mmol). The mixture was stirred at rt for about 15 min then warmed to about 40° C. After about 15 min the mixture was cooled to rt then thionyl chloride (0.575 mL, 7.86 mmol) was added. The mixture was warmed to about 40° C. for about 8 h then cooled to rt and stirred for about 12 h. The mixture was concentrated under reduced pressure then triturated with heptane (15 mL). The solids were collected by filtration and washed with heptane (2×5 mL). The solids were dried under vacuum to give the title compound (2.51 g, 86%); LC/MS (Table A, Method b) $R_t$=1.96 min; MS m/z: 274, 276 (M+H)$^+$

Step 3: rac-(1R,10bR)-9-Bromo-1-(2-(difluoromethoxy)phenyl)-3,4-dihydro-1H-[1,4]oxazino[3,4-a]isoindol-6(10bH)-one A flask under nitrogen was charged with 5-bromo-2-(2-chloroethyl)isoindolin-1-one (1.0 g, 3.64 mmol) and THF (30 mL) then cooled to an internal temperature of about −70° C. Potassium bis(trimethylsilyl)amide (0.5 M in toluene) (8.0 mL, 4.0 mmol) was added keeping the temperature between about −65° C. and −70° C. The mixture was allowed to warm to about −50° C. over about 15 min. The mixture was cooled to about −60° C. then 2-(difluoromethoxy)benzaldehyde (0.69 g, 4.01 mmol) was added. The mixture was warmed to rt over about 45 min then added to a saturated aqueous ammonium chloride (25 mL) and water (25 mL) mixture. DCM (50 mL) was added then the layers were separated. The aqueous layer was extracted with DCM (25 mL) then the organic solutions were combined and washed with water (2×50 mL) then saturated aqueous NaCl (30 mL). The organic layer was dried over MgSO$_4$, filtered and the filtrate concentrated under reduced pressure. The residue was purified via flash chromatography on silica gel (50% EtOAc/heptane). The appropriate fractions were collected and concentrated under reduced pressure to give the title compound (1.35 g, 90%); LC/MS (Table A, Method b) $R_t$=2.29 min; MS m/z: 410, 412 (M+H)$^+$

Step 4: rac-(1R,10bR)-1-(2-(Difluoromethoxy)phenyl)-9-(2-morpholinopyrimidin-5-yl)-3,4-dihydro-1H-[1,4]oxazino[3,4-a]isoindol-6(10bH)-one A flask under nitrogen was charged with rac-(1R,10bR)-9-bromo-1-(2-(difluoromethoxy)phenyl)-3,4-dihydro-1H-[1,4]oxazino[3,4-a]isoindol-6(10bH)-one (0.200 g, 0.488 mmol), 4-(5-(4,4,5,5-tetramethyl-1,3,2-dioxaborolan-2-yl)pyrimidin-2-yl)morpholine (0.170 g, 0.585 mmol), 1,4-dioxane (8 mL), water (2 mL), cesium carbonate (0.238 g, 0.731 mmol) and PdCl$_2$(PPh$_3$)$_2$ (0.0342 g, 0.049 mmol). The mixture was warmed to about 80° C. for about 2.5 h then cooled to rt, diluted with EtOAc (70 mL) and washed with water (2×10 mL). The organic layer was dried over MgSO$_4$ then filtered and concentrated under reduced pressure. The residue was purified via flash chromatography on silica gel (5-80% EtOAc/heptane). The appropriate fractions were collected and concentrated under reduced pressure to give the title compound (0.150 g, 59%); LC/MS (Table A, Method a) $R_t$=2.13 min; MS m/z: 495 (M+H)$^+$

Example #19

3-(5-(Hydroxymethyl)-2-methoxyphenyl)-6-(2-morpholinopyrimidin-5-yl)-2,3-dihydropyrazolo[1,2-a]indazol-9(1H)-one

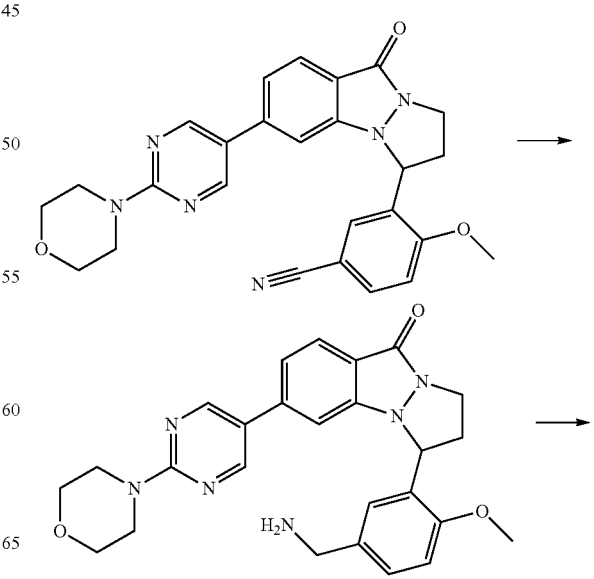

Step 1: 3-(5-(Aminomethyl)-2-methoxyphenyl)-6-(2-morpholinopyrimidin-5-yl)-2,3-dihydropyrazolo[1,2-a]indazol-9(1H)-one

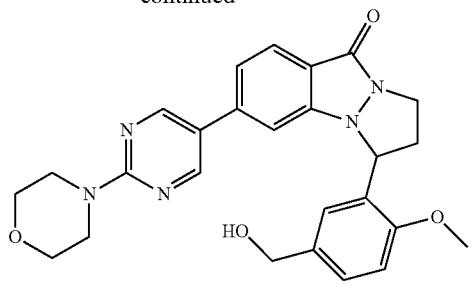

4-Methoxy-3-(6-(2-morpholinopyrimidin-5-yl)-9-oxo-1,2,3,9-tetrahydropyrazolo[1,2-a]indazol-3-yl)benzonitrile (Example #8.2) (0.19 g, 0.406 mmol) was dissolved in MeOH (10 mL). The material was cycled three times through a flow hydrogenation apparatus (H-Cube® Continuous-flow Hydrogenation Reactor, 70° C., 50 bar, 0.9 mL/min, Raney Nickel cartridge). The resulting mixture was concentrated under reduced pressure then purified by reverse phase HPLC (Table C, Method 3) to give the title compound after lyophilzation (0.065 g, 34%); LC/MS (Table A, Method a) $R_t$=1.32 min; MS m/z: 473 (M+H)$^+$.

Step 2: 3-(5-(Hydroxymethyl)-2-methoxyphenyl)-6-(2-morpholinopyrimidin-5-yl)-2,3-dihydropyrazolo[1,2-a]indazol-9(1H)-one 3-(5-(Aminomethyl)-2-methoxyphenyl)-6-(2-morpholinopyrimidin-5-yl)-2,3-dihydropyrazolo[1,2-a]indazol-9(1H)-one (0.025 g, 0.053 mmol) was dissolved in AcOH (0.5 mL). Water (0.5 mL) was added then the mixture was cooled to about 0° C. Sodium nitrite (0.015 g, 0.212 mmol) was added then the mixture was warmed to rt and stirred for about 1 h. A second portion of sodium nitrite (0.015 g, 0.212 mmol) was added then the mixture was stirred for about 4 h. The mixture was basified with saturated sodium bicarbonate then extracted with EtOAc (25 mL). The organic solution was dried over magnesium sulfated filtered and concentrated. The residue was dissolved in 1,4-dioxane (1 mL) and water (0.25 mL). Lithium hydroxide (6.3 mg, 0.265 mmol) was added then the mixture was heated to about 80° C. for about 1 hour. The mixture was cooled then partitioned between EtOAc (15 mL) and water (5 mL). The organic solution was dried over magnesium sulfate, filtered and concentrated. The residue was triturated with MeOH then dried to give the title compound (0.018 g, 71%); LC/MS (Table A, Method b) $R_t$=1.62 min; MS m/z: 474 (M+H)$^+$ (TNF IC$_{50}$=B).

The compounds shown in Table 9 were synthesized in a manner similar to Example #16, Step 7 from rac-(1R,9bR)-8-bromo-1-(2-(difluoromethoxy)phenyl)-2,3-dihydro-1H-pyrrolo[2,1-a]isoindol-5(9bH)-one (Preparation #20) and the corresponding boronic acid/boronate. Enantiomers were separated by the chiral methods listed in Table B when applicable.

TABLE 9

| Boronic acid/boronate | Product | Example # | $R_t$ min (Table A, Method) | m/z ESI+ (M + H)$^+$ | Method for chiral separation/ Order of elution/Sign | TNF IC$_{50}$ |
|---|---|---|---|---|---|---|
| 2-(4-Morpholono)pyrimidine-5-boronic acid pinacol ester | | 9.1 | 2.18 (a) | 479 | 16/1$^{st}$/− | C |
| 2-(4-Morpholino)pyrimidine-5-boronic acid pinacol ester | | 9.2 | 2.18 (a) | 479 | 16/2$^{nd}$/+ | A |

The compounds shown in Table 10 were synthesized in a manner similar to Example #4, Step 1 from rac-(1R,9bR)-8-bromo-1-(2-(difluoromethoxy)phenyl)-2,3-dihydro-1H-pyrrolo[2,1-a]isoindol-5(9bH)-one (Preparation #20) and the corresponding aryl halide. Enantiomers were separated by the chiral methods listed in Table B when applicable.

TABLE 10

| Aryl halide | Product | Example # | $R_t$ min (Table A, Method) | m/z ESI+ (M + H)⁺ | Method for chiral separation/ Order of elution/Sign | TNF IC$_{50}$ |
|---|---|---|---|---|---|---|
| 2-(5-Bromopyrimidin-2-yl)propan-2-ol | | 10.1 | 1.95 (a) | 452 | 17/1ˢᵗ/− | C |
| 2-(5-Bromopyrimidin-2-yl)propan-2-ol | | 10.2 | 1.95 (a) | 452 | 17/2ⁿᵈ/+ | B |
| (R)-5-Bromo-2-(2-(methoxymethyl)pyrrolidin-1-yl)pyrimidine (Preparation #10) | | 10.3 | 2.42 (a) | 507 | 18/1ˢᵗ/− | B |
| (R)-5-Bromo-2-(2-(methoxymethyl)pyrrolidin-1-yl)pyrimidine (Preparation #10) | | 10.4 | 2.42 (a) | 507 | 18/2ⁿᵈ/+ | C |

The compounds shown in Table 11 were synthesized in a manner similar to Example #4, Step 1 from (1R,9bR)-8-bromo-1-(2-(difluoromethoxy)phenyl)-2,3-dihydro-1H-pyrrolo[2,1-a]isoindol-5(9bH)-one (Preparation #22) and the corresponding aryl halide.

TABLE 11

| Aryl halide | Product | Example # | $R_t$ min (Table A, Method) | m/z ESI+ $(M + H)^+$ | TNF $IC_{50}$ |
|---|---|---|---|---|---|
| (R)-7-(5-Bromopyrimidin-2-yl)hexahydroimidazo[1,5-a]pyrazin-3(2H)-one (Preparation #9) | | 11.1 | 1.81 (a) | 533 | A |
| (S)-7-(5-Bromopyrimidin-2-yl)hexahydroimidazo[1,5-a]pyrazin-3(2H)-one (Preparation #8) | | 11.2 | 1.81 (a) | 533 | A |

The compounds shown in Table 12 were synthesized in a manner similar to Example #4 from 6-bromo-1-(1-(2-(difluoromethoxy)phenyl)-3-hydroxypropyl)-5-fluoro-1H-indazol-3(2H)-one (Preparation #24) and the corresponding bromide. Enantiomers were separated by the chiral methods listed in Table B when applicable.

TABLE 12

| Bromide | Product | Example # | $R_t$ min (Table A, Method) | m/z ESI+ $(M + H)^+$ | Method for chiral separation/ Order of elution/Sign | TNF $IC_{50}$ |
|---|---|---|---|---|---|---|
| 2-(5-Bromopyrimidin-2-yl)propan-2-ol | | 12.1 | 1.89 (a) | 471 | 19/1$^{st}$/+ | A |

TABLE 12-continued

| Bromide | Product | Example # | R$_t$ min (Table A, Method) | m/z ESI+ (M + H)+ | Method for chiral separation/ Order of elution/Sign | TNF IC$_{50}$ |
|---|---|---|---|---|---|---|
| 2-(5-Bromopyrimidin-2-yl)propan-2-ol | 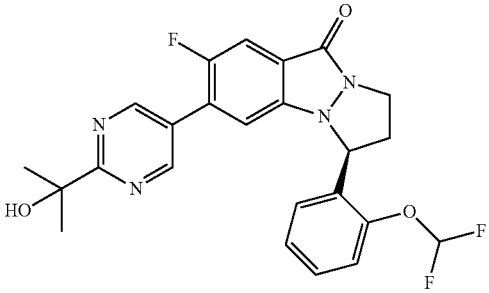 [SMILES: CC(C)(O)c1ncc(-c2cc3c(cc2F)c(=O)n2n3[C@H](c3ccccc3OC(F)F)CC2)cn1] | 12.2 | 1.89 (a) | 471 | 19/2$^{nd}$/− | A |

The compounds shown in Table 13 were synthesized in a manner similar to Example #4 from 6-bromo-3-(2-(difluoromethoxy)-5-methylphenyl)-7-fluoro-2,3-dihydropyrazolo[1,2-a]indazol-9(1H)-one (Preparation #29) and the corresponding bromide. Enantiomers were separated by the chiral methods listed in Table D when applicable.

TABLE 13

| Bromide | Product | Example # | R$_t$ min (Table A, Method) | m/z ESI+ (M + H)+ | Method for SFC separation/ Order of elution/Sign | TNF IC$_{50}$ |
|---|---|---|---|---|---|---|
| 2-(5-Bromopyrimidin-2-yl)propan-2-ol | 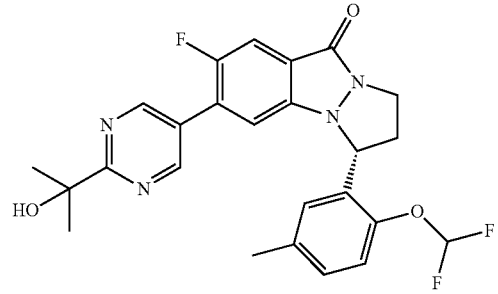 [SMILES: Cc1ccc(OC(F)F)c([C@H]2CCn3c(=O)c4cc(F)c(-c5cnc(C(C)(C)O)nc5)cc4n32)c1] | 13.1 | 1.31 (c) | 485 | 1/1$^{st}$/− | A |
| 2-(5-Bromopyrimidin-2-yl)propan-2-ol | 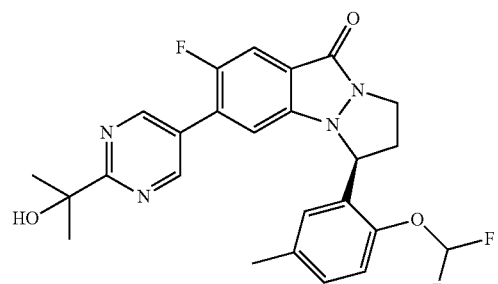 | 13.2 | 1.21 (c) | 485 | 1/2$^{nd}$/+ | A |

The compounds shown in Table 14 were synthesized in a manner similar to Example #4 from (S)-6-bromo-3-(2-(difluoromethoxy)-5-methylphenyl)-2,3-dihydropyrazolo[1,2-a]indazol-9(1H)-one (Preparation #30) and the corresponding bromide.

TABLE 14

| Bromide | Product | Example # | R$_t$ min (Table A, Method) | m/z ESI+ (M + H)$^+$ | Optical Rotation | TNF IC$_{50}$ |
|---|---|---|---|---|---|---|
| (S)-7-(5-Bromopyrimidin-2-yl)hexahydroimidazo[1,5-a]pyrazin-3(2H)-one (Preparation #8) | | 14.1 | 1.81 (a) | 548 | NA | A |
| 2-(5-Bromopyrimidin-2-yl)propan-2-ol | | 14.2 | 1.25 (c) | 467 | NA | A |

The compounds shown in Table 15 were synthesized in a manner similar to Example #4 from (R)-6-bromo-3-(2-(difluoromethoxy)-5-methylphenyl)-2,3-dihydropyrazolo[1,2-a]indazol-9(1H)-one (Preparation #31) and the corresponding bromide.

TABLE 15

| Bromide | Product | Example # | R$_t$ min (Table A, Method) | m/z ESI+ (M + H)$^+$ | Optical Rotation | TNF IC$_{50}$ |
|---|---|---|---|---|---|---|
| (S)-7-(5-Bromopyrimidin-2-yl)hexahydroimidazo[1,5-a]pyrazin-3(2H)-one (Preparation #8) | | 15.1 | 1.82 (a) | 548 | NA | A |

TABLE 15-continued

| Bromide | Product | Example # | R, min (Table A, Method) | m/z ESI+ (M + H)+ | Optical Rotation | TNF IC$_{50}$ |
|---|---|---|---|---|---|---|
| 2-(5-Bromopyrimidin-2-yl)propan-2-ol | 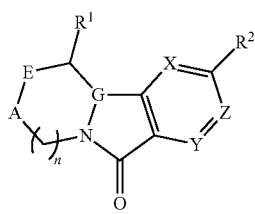 | 15.2 | 1.25 (c) | 467 | NA | A |

What is claimed:

1. A compound of Formula (I),

Formula (I)

or a pharmaceutically acceptable salt or stereoisomer thereof, wherein:
X, Y and Z are CR$^4$;
A is —C(R$^z$)$_2$—;
E is CH$_2$ or O and G is CH; or
E is CH$_2$ and G is CH or N;
R$^1$ is optionally substituted aryl or optionally substituted heteroaryl;
R$^2$ is —R$^{2a}$-R$^{2b}$, wherein:
 R$^{2a}$ is an optionally substituted saturated, unsaturated or partially saturated heterocyclyl, or optionally substituted heteroaryl; and
 R$^{2b}$ is —N(R$^a$)(R$^b$), —O(R$^a$), optionally substituted (C$_1$-C$_5$)alkyl, optionally substituted (C$_3$-C$_6$)cycloalkyl, —(CH$_2$)$_p$-optionally substituted heteroaryl, or —(CH$_2$)$_p$-optionally substituted heterocyclyl; wherein
  R$^a$ and R$^b$ are independently selected from the group consisting of H, optionally substituted (C$_1$-C$_5$) alkyl, and —(CH$_2$)$_n$-optionally substituted heterocyclyl;
each instance of R$^4$ is independently H, halo, CF$_3$, or (C$_1$-C$_3$)alkyl;
each instance of R$^z$ is independently H, halo, CF$_3$, or (C$_1$-C$_3$)alkyl;
n is 0; and
p is 0 or 1;
wherein heterocyclyl is:
 a non-aromatic monocyclic, bicyclic, tricyclic, or spirocyclic ring having 5 to 12 ring atoms which include at least one nitrogran, oxygen, or sulfur ring atom; or
 an azetidinyl ring.

2. The compound according to claim 1, or a pharmaceutically acceptable salt or stereoisomer thereof, wherein:
R$^{2b}$ is —N(R$^a$)(R$^b$), —O(R$^a$), optionally substituted (C$_1$-C$_5$)alkyl, optionally substituted (C$_3$-C$_6$)cycloalkyl, or —(CH$_2$)$_p$-optionally substituted heterocyclyl; and
R$^a$ and R$^b$ are independently selected from the group consisting of H, optionally substituted (C$_1$-C$_5$)alkyl, and —(CH$_2$)$_n$-optionally substituted heterocyclyl.

3. The compound according to claim 1, or a pharmaceutically acceptable salt or streoisomer thereof, wherein E is CH$_2$, and G is CH or N.

4. The compound according to claim 1, or a pharmaceutically acceptable salt or stereoisomer thereof, wherein X is CH, Y is CH, and Z is CR$^4$.

5. The compound according to claim 4, or a pharmaceutically acceptable salt or stereoisomer thereof, wherein R$^4$ is F.

6. The compound according to claim 1, or a pharmaceutically acceptable salt or stereoisomer thereof, wherein X is CH, Y is CH, and Z is CH.

7. The compound according to claim 1, or a pharmaceutically acceptable salt or stereoisomer thereof, wherein E is CH$_2$, and G is N.

8. The compound according to claim 1, or a pharmaceutically acceptable salt or stereoisomer thereof, wherein R$^1$ is optionally substituted phenyl, optionally substituted pyrazolyl, optionally substituted pyridyl, optionally substituted pyrimidinyl, or optionally substituted thiazolyl.

9. The compound according to claim 1, or a pharmaceutically acceptable salt or stereoisomer thereof, wherein R$^1$ is optionally substituted phenyl.

10. The compound according to claim 1, or a pharmaceutically acceptable salt or stereoisomer thereof, wherein R$^1$ is optionally substituted by one or more substituents independently selected from the group consisting of —CF$_3$, —CN, —C(O)NH$_2$, —OCHF$_2$, —OCH$_3$, and (C$_1$-C$_3$)alkyl.

11. The compound according to claim 1, or a pharmaceutically acceptable salt or stereoisomer thereof, wherein R$^1$ is optionally substituted by one or more substituents independently selected from the group consisting of —CH$_3$ and —OCHF$_2$.

12. The compound according to claim 1, or a pharmaceutically acceptable salt or stereoisomer thereof, wherein R$^{2a}$ is optionally substituted pyrimidinyl or optionally substituted dihydropyranyl.

13. The compound according to claim 1, or a pharmaceutically acceptable salt or stereoisomer thereof, wherein $R^{2a}$ is 1,2,4-oxadiazolyl, optionally substituted pyrazolyl, optionally substituted pyridinyl, optionally substituted pyrimidinyl, or optionally substituted 1,2,4-thiadiazolyl.

14. The compound according to claim 1, or a pharmaceutically acceptable salt or stereoisomer thereof, wherein $R^{2b}$ is $N(R^a)(R^b)$, optionally substituted $(C_1$-$C_4)$alkyl, optionally substituted morpholinyl, optionally substituted piperazinyl, optionally substituted piperidinyl, 1,1-dioxidothiomorpholinyl, optionally substituted hexahydroimidazo[1,5-a]pyrazin-3(2H)-one, optionally substituted 7-azaspiro[3.5]nonane, or optionally substituted pyrrolidinyl.

15. The compound according to claim 1, or a pharmaceutically acceptable salt or stereoisomer thereof, wherein:

$R^{2b}$ is —$N(R^a)(R^b)$, optionally substituted $(C_1$-$C_3)$alkyl, optionally substituted 7-azaspiro[3.5]nonanyl, optionally substituted morpholinyl, 1,1-dioxidothiomorpholinyl, optionally substituted piperazinyl, optionally substituted piperidinyl, optionally substituted hexahydroimidazo[1,5-a]pyrazin-3(2H)-one, or optionally substituted pyrrolidinyl; $R^a$ is H or $(C_1$-$C_3)$alkyl, and $R^b$ is optionally substituted $(C_1$-$C_3)$alkyl, methoxypropyl, -5-oxopyrrolidin-3-ylmethyl, or tetrahydrofuranyl.

16. The compound according to claim 1, or a pharmaceutically acceptable salt or stereoisomer thereof, wherein $R^{2b}$ is optionally substituted $(C_1$-$C_3)$alkyl, —$CH_2$-pyrazolyl, or —$CH_2$-triazolyl.

17. The compound according to claim 1, or a pharmaceutically acceptable salt or stereoisomer thereof, wherein $R^{2b}$ is optionally substituted $(C_1$-$C_3)$alkyl, optionally substituted 7-azaspiro[3.5]nonanyl, optionally substituted morpholinyl, or hexahydroimidazo[1,5-a]pyrazin-3(2H)-one.

18. The compound according to claim 1, or a pharmaceutically acceptable salt or stereoisomer thereof, wherein $R^{2b}$ is optionally substituted by —$CH_2OH$, —$C(OH)(CH_3)_2$, —$C(O)CH_3$, —$C(O)OH$, —OH, or alkoxyalkyl.

19. The compound according to claim 1, or a pharmaceutically acceptable salt or stereoisomer thereof, wherein $R^{2b}$ is optionally substituted by one or more substituents independently selected from the group consisting of $CH_3$, —$C(O)CH_2OH$, —$C(O)CH_3$.

20. The compound according to claim 1 wherein the compound is selected from the group consisting of:

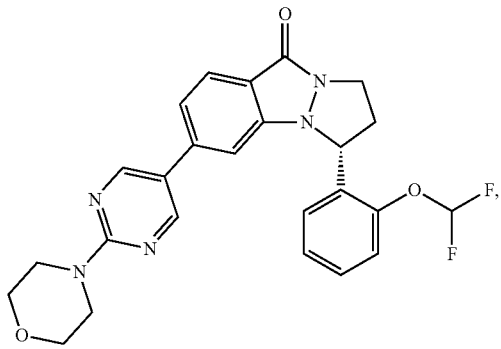

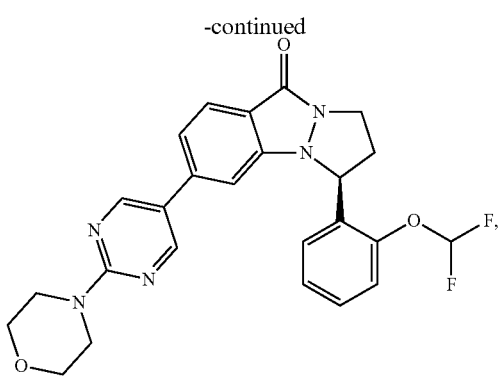

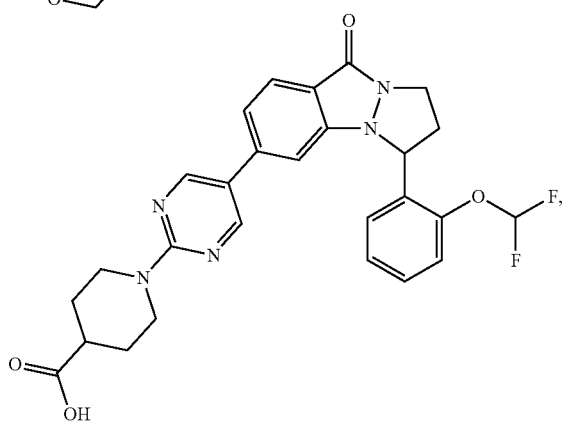

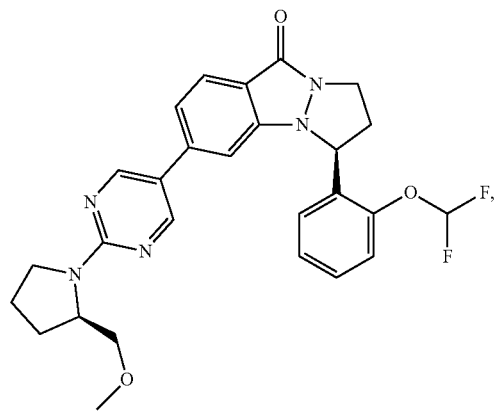

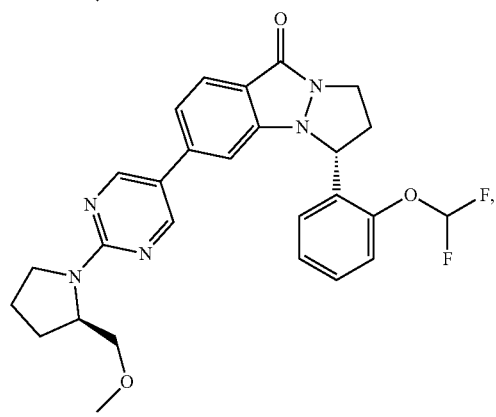

117
-continued
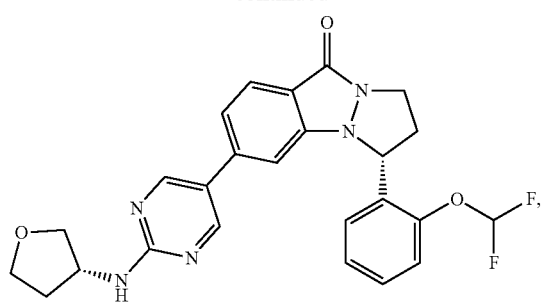
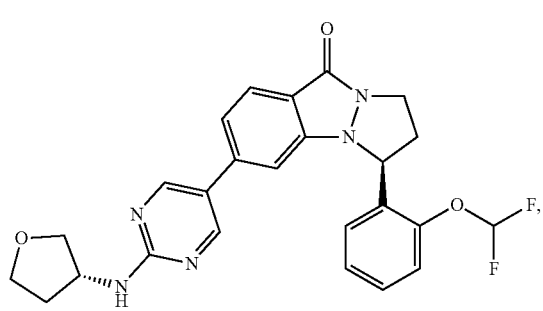
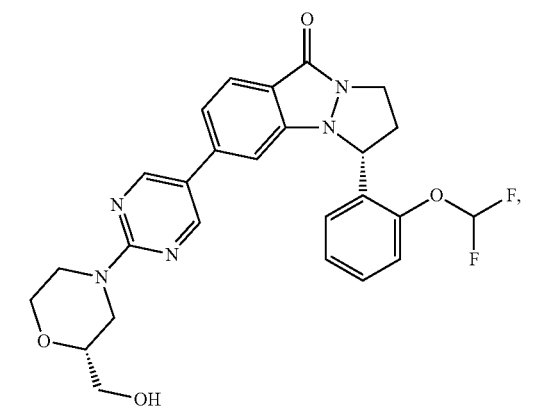
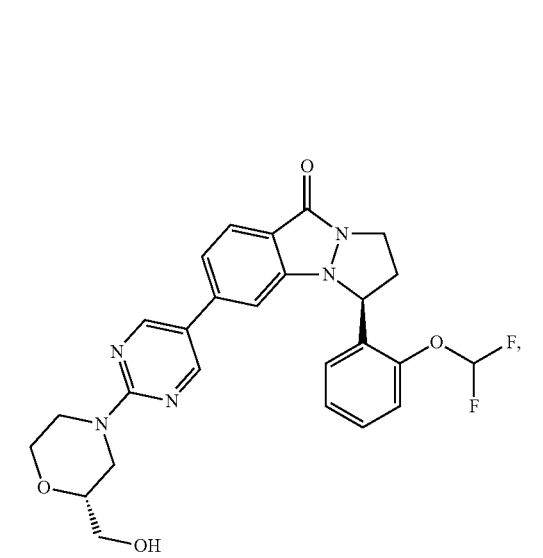
118
-continued
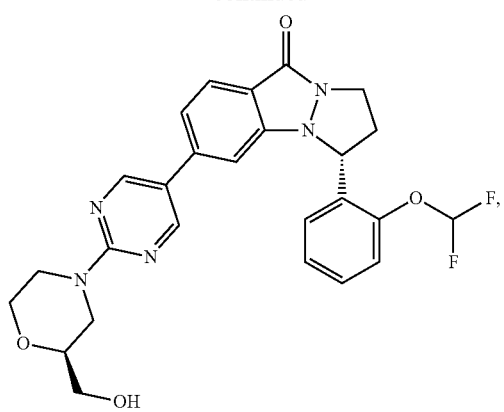
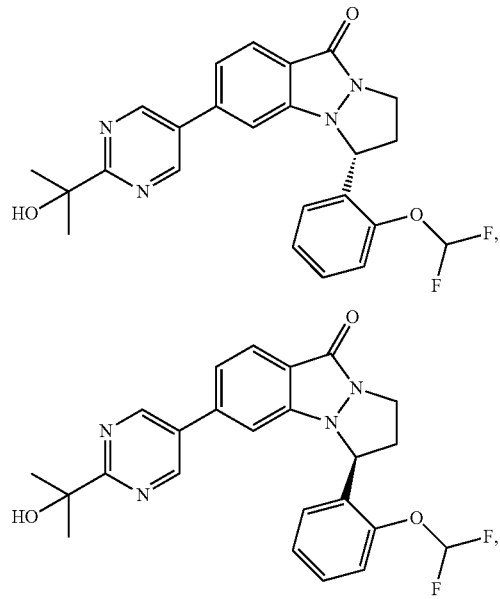
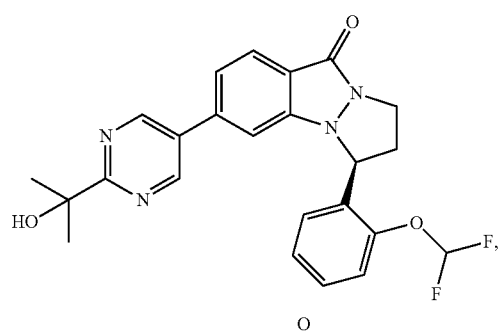
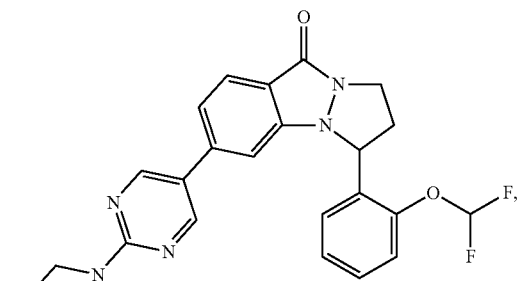
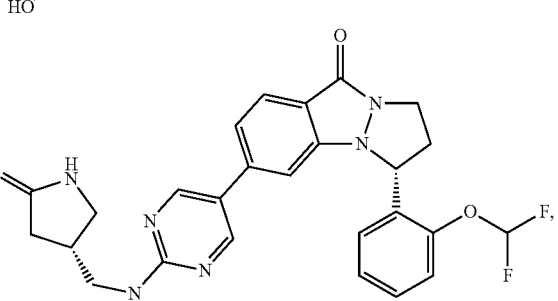

119
-continued
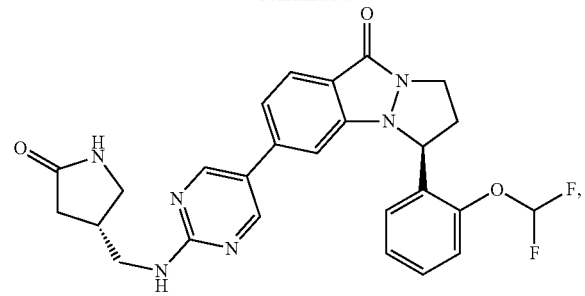
120
-continued
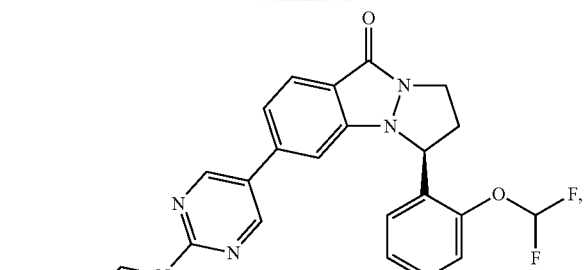
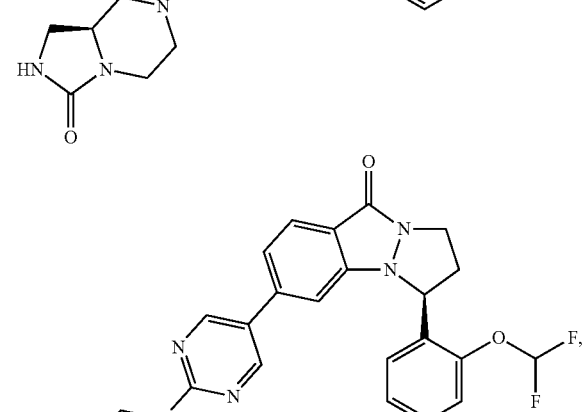
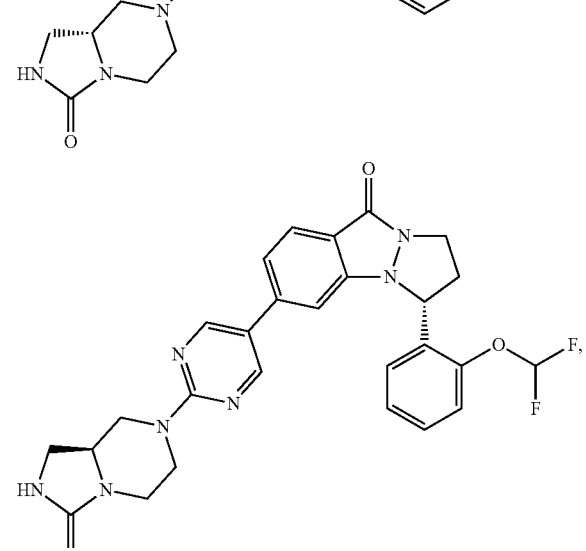
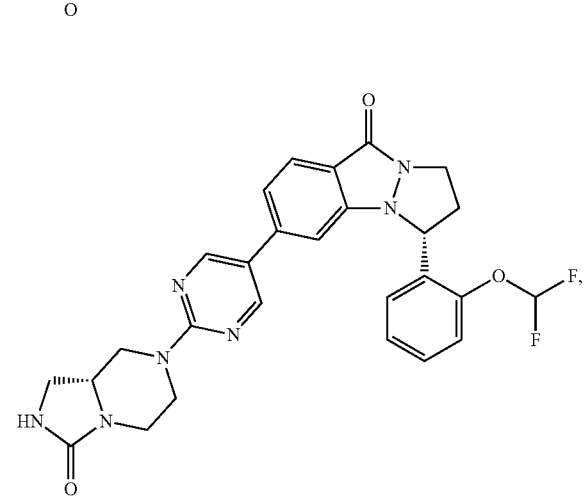

121
-continued
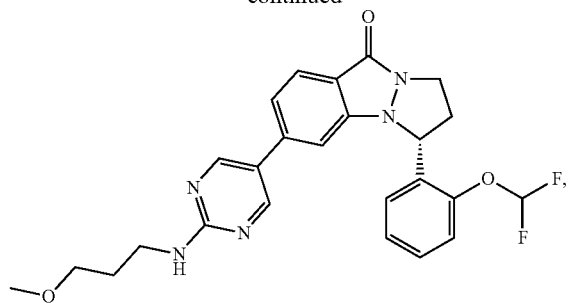
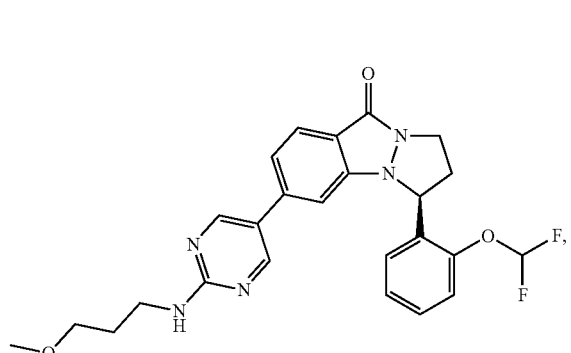
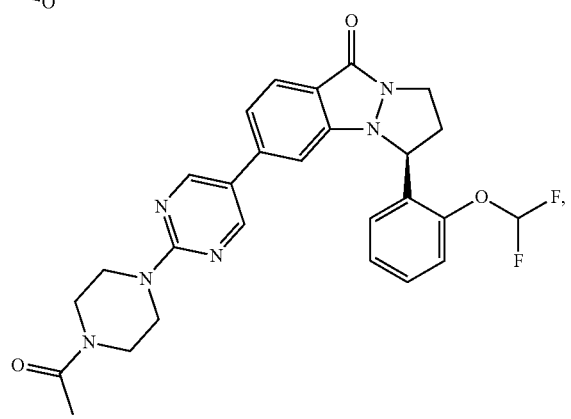
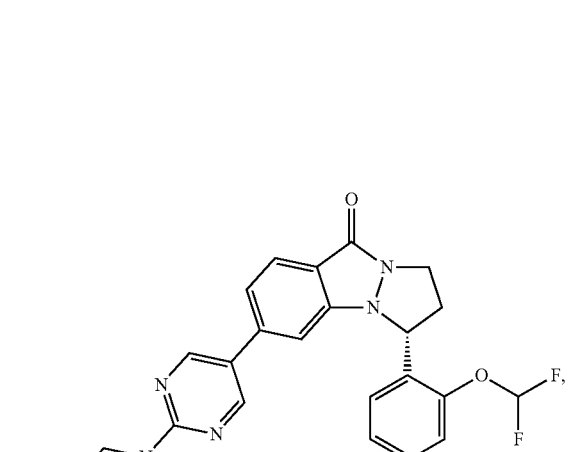
122
-continued
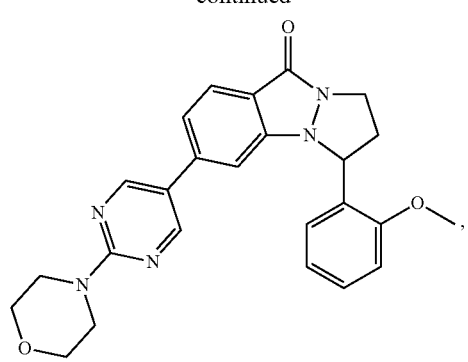
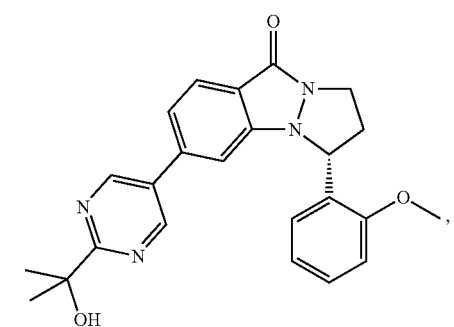
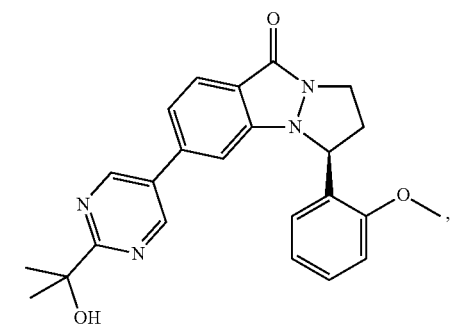
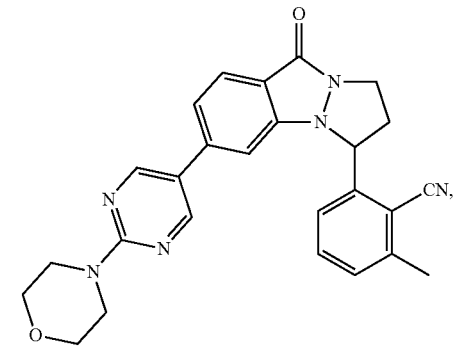
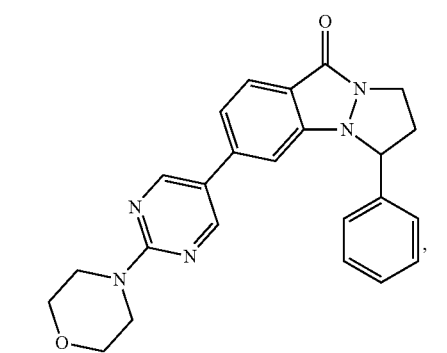

123
-continued
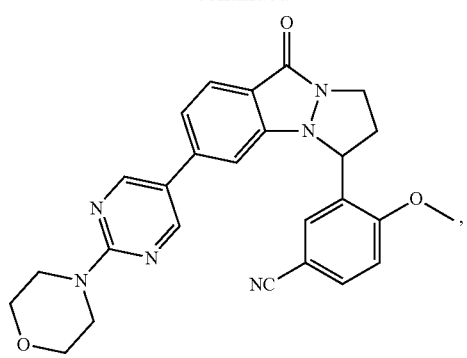
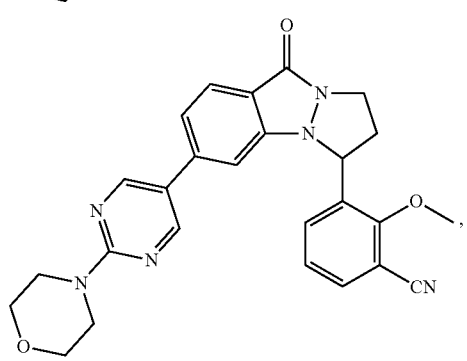
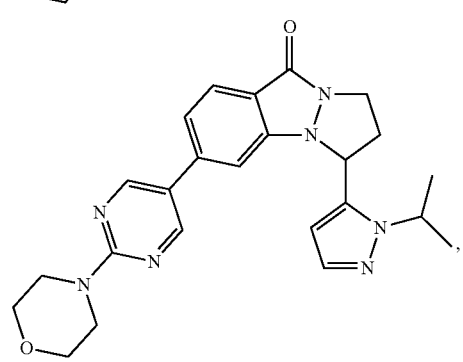
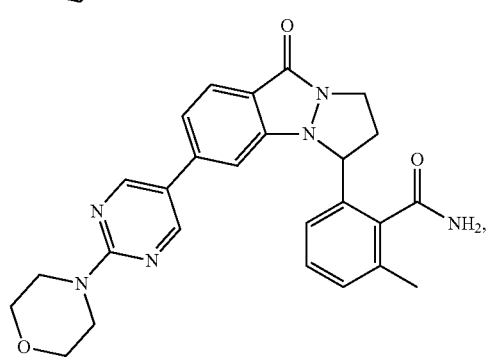
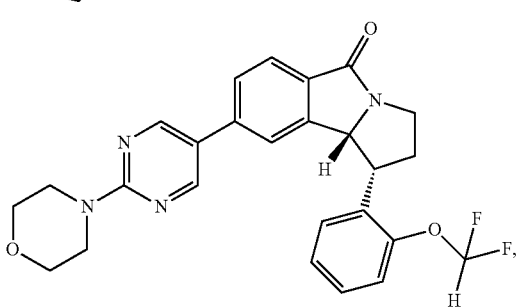
124
-continued
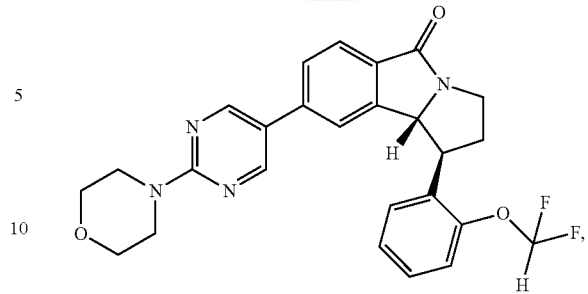
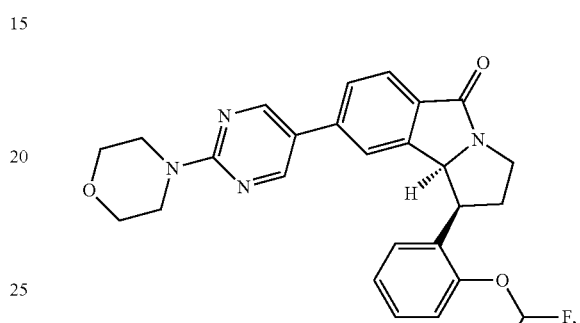
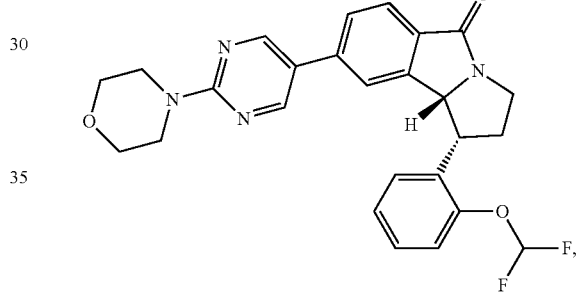
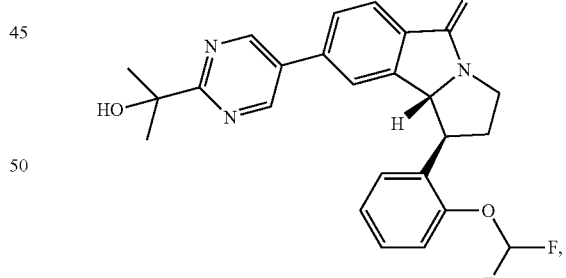
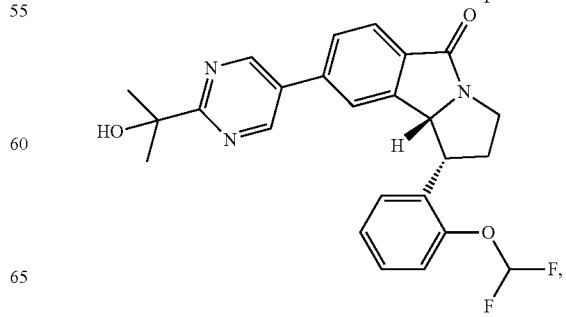

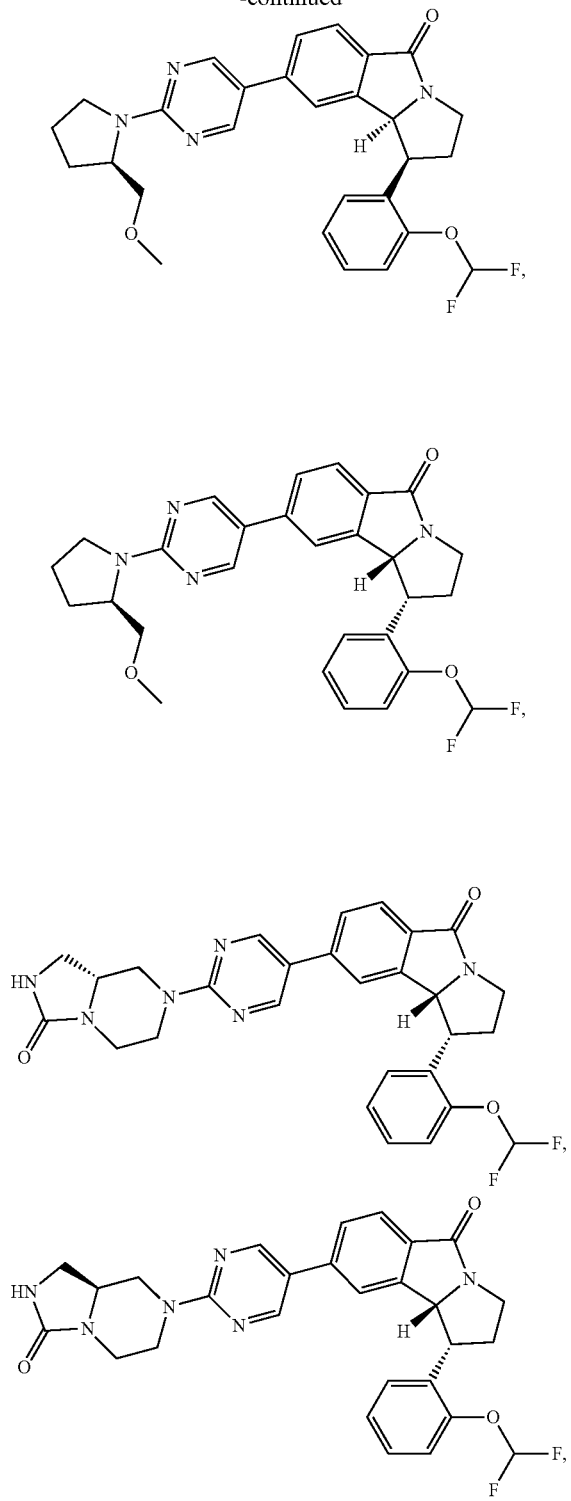
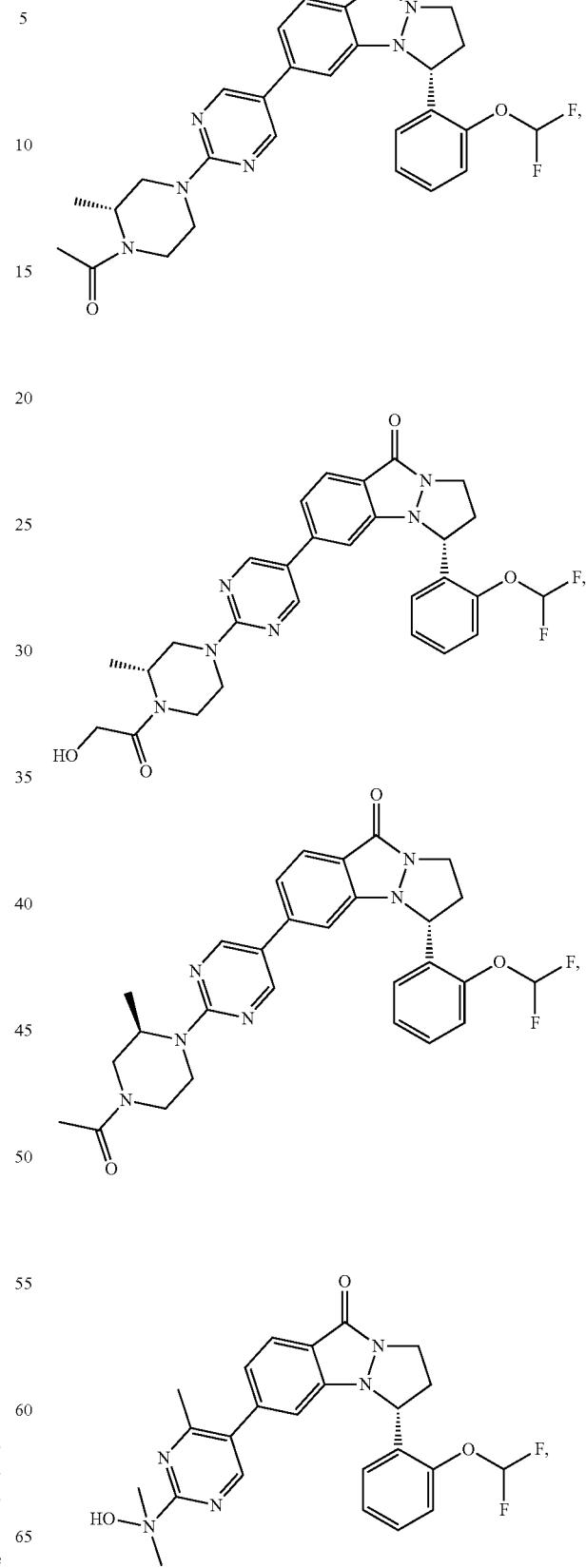
and pharmaceutically acceptable salts thereof.
21. A pharmaceutical composition comprising a compound according to claim 1, or a pharmaceutically acceptable salt or stereoisomer thereof; and one or more pharmaceutically acceptable excipients.
22. The compound according to claim 1, wherein the compound is selected from the group consisting of:

127
-continued
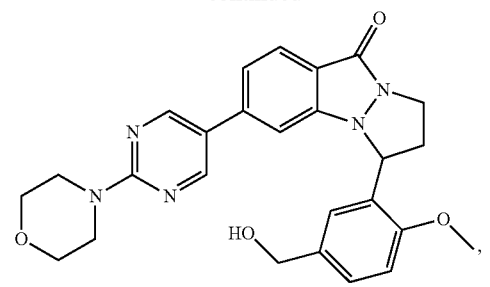
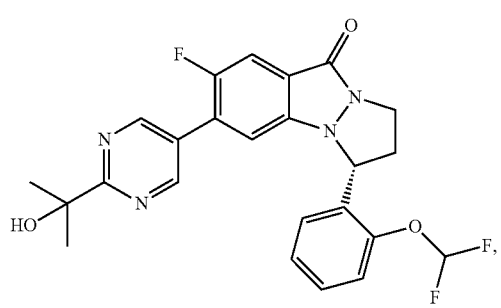
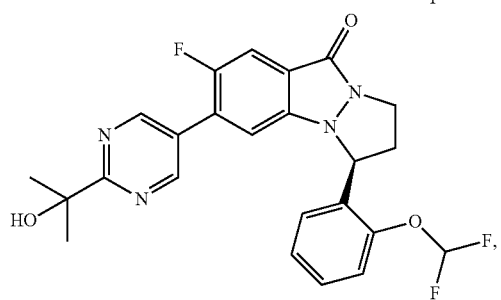
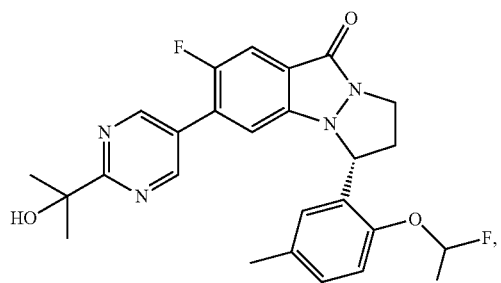
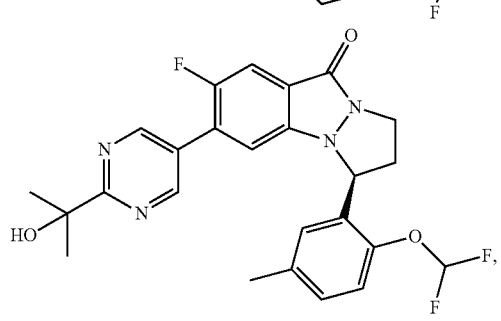
128
-continued
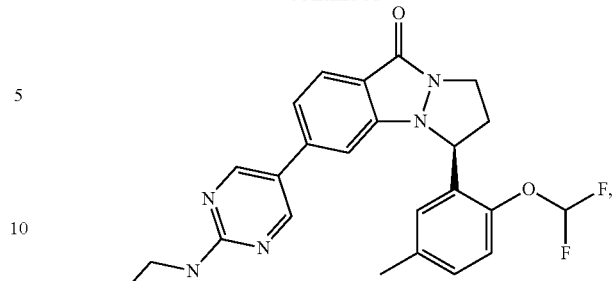
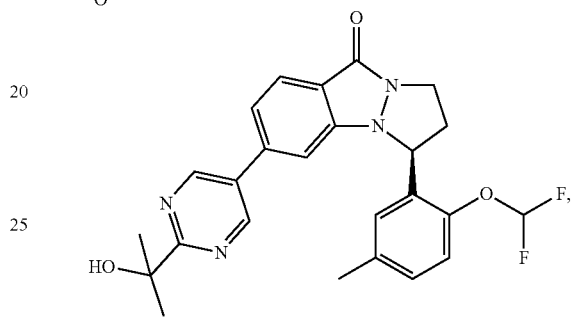
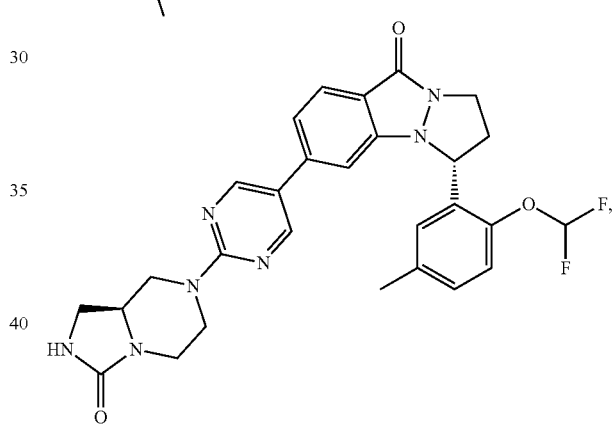
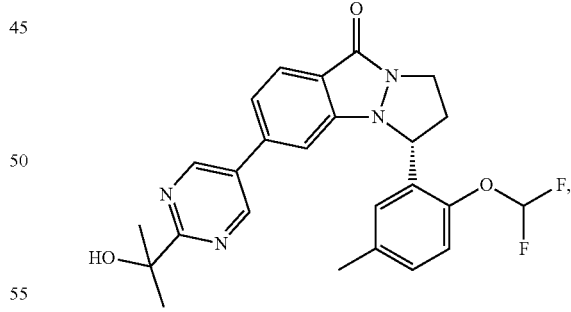
and pharmaceutically acceptable salts thereof.
23. The compound according to claim 1, or a pharmaceutically acceptable salt or stereoisomer thereof, wherein:
X is CH;
Y is CH;
Z is $CR^4$, wherein $R^4$ is H or F;
A is $-C(R^Z)_2-$ wherein $R^Z$ is H;
E is $CH_2$;
G is N;

R$^1$ is phenyl optionally substituted by one or more substituents independently selected from the group consisting of -CF$_3$, -CN, -C(O)NH$_2$, -OCHF$_2$, -OCH$_3$, and (C$_1$-C$_3$)alkyl;

R$^2$ is -R$^{2a}$-R$^{2b}$, wherein R$^{2a}$ is pyrimidinyl, and R$^{2b}$ is selected from the group consisting of: -N(R$^a$)(R$^b$) wherein R$^a$ is H or (C$_1$-C$_3$)alkyl, and R$^b$ is (C$_1$-C$_3$) alkyl, methoxypropyl, 5-oxopyrrolidin-3-ylmethyl, or tetrahydrofuranyl;

(C$_1$-C$_3$)alkyl optionally substituted by -CH$_2$OH, -C(OH)(CH$_3$)$_2$, -C(O)CH$_3$, -C(O)OH, -OH, or alkoxyalkyl;

7-azaspiro[3.5]nonanyl optionally substituted -CH$_2$OH, -C(OH)(CH$_3$)$_2$, -C(O)OH, -OH, or alkoxyalkyl;

morpholinyl optionally substituted by -CH$_2$OH, -C(OH)(CH$_3$)$_2$, -C(O)OH, -OH, or alkoxyalkyl;

piperazinyl optionally substituted by -CH$_2$OH, -C(OH)(CH$_3$)$_2$, -C(O)OH, -OH, or alkoxyalkyl;

piperidinyl optionally substituted by -CH$_2$OH, -C(OH)(CH$_3$)$_2$, -C(O)OH, -OH, or alkoxyalkyl;

hexahydroimidazo[1,5-a]pyrazin-3(2H)-one optionally substituted by -CH$_2$OH, -C(OH)(CH$_3$)$_2$, -C(O)OH, -OH, or alkoxyalkyl; and pyrrolidinyl optionally substituted by -CH$_2$OH, -C(OH)(CH$_3$)$_2$, -C(O)OH, -OH, or alkoxyalkyl.

24. The compound according to claim 1, or a pharmaceutically acceptable salt or stereoisomer thereof, Wherein optionally substituted refers to optional substitution with one or more substituents selected from the group consisting of (C$_1$-C$_8$)alkyl; (C$_2$-C$_8$)alkenyl; (C$_2$-C$_8$)alkynyl; (C$_3$-C$_{10}$)cycloalkyl; F; Cl; BR; I; halogenated (C$_1$-C$_8$)alkyl; -O-(C$_1$-C$_8$)alkyl; =O; =CH$_2$; -OH; -CH$_2$OH; -CH$_2$OCH$_3$; -CH$_2$NH$_2$; (C$_1$-C$_4$)alkyl-OH; -CH$_2$CH$_2$OCH$_2$CH$_3$;-S-(C$_1$-C$_8$)alkyl; -SH; -NH(C$_1$-C$_8$)alkyl; -NH((C$_1$-C$_8$)alkyl)$_2$; -NH$_2$; -C(O)NH$_2$; -CH$_2$NHC(O)(C$_1$-C$_8$)alkyl; -CH$_2$NCH(O)CH$_2$Cl; -CH$_2$NHC(O)CH$_2$CN; -CH$_2$NHC(O)CH$_2$CH$_2$N(CH$_3$)$_2$; -CH$_2$NHC(O)C(=CH$_2$)CH$_3$; -CH$_2$NHC(O)(C$_2$-C$_4$)alkynyl; -CH$_2$NHC(O)CH$_2$CH$_2$- piperidinyl; -(C$_1$-C$_4$)alkyl-morpholinyl; -CH$_2$NHC(O)CH$_2$)-phenyl wherein the phenyl is optionally substituted with halogen; (C$_1$-C$_4$)alkoxy; -C(O)(C$_1$-C$_4$)alkyl; -C(O)(C$_1$-C$_4$)alkoxy; -C(O)N(CH$_3$)$_2$; -N(CH$_3$)$_2$; -NHC(O)(C$_1$-C$_4$; )alkyl; -NHC(O)(C$_2$-C$_4$)alkenyl; -NHC(O)CH$_2$CN; -S(O)$_2$(C$_1$-C$_4$)alkyl; 4-methylpiperazinecarbonyl; -(C$_1$-C$_4$)alkylC(O)NH$_2$; -C(O)NH(C$_1$-C$_8$)alkyl; -C(O)N((C$_1$-C$_8$)alkyl)$_2$; -C(O)N(H)(C$_3$-C$_8$)cycloalkyl; -C(O)(C$_1$-C$_4$)alkyl -OH; -(C$_1$-C$_4$)alkyl(C$_1$-C$_4$)alkoxy; -NHC(O)H; -NHC(O)(C$_1$-C$_8$)alkyl; -NHC(O)(C$_3$-C$_8$)cycloalkyl; -N((C$_1$-C$_8$)alkyl)C(O)H; -N((C$_1$-C$_8$)alkyl)C(O)(C$_1$-C$_8$)alkyl; -NHC(O)NH$_2$; -NHC(O)NH(C$_1$-C$_8$)alkyl; -N((C$_1$-C$_8$)alkyl)C(O)NH$_2$; -NHC(O)N((C$_1$-C$_8$)alkyl)$_2$; -N((C$_1$-C$_8$)alkyl)C(O)N((C$_1$-C$_8$)alkyl)$_2$; N((C$_1$-C$_8$)alkyl)C(O)NH((C$_1$-C$_8$)alkyl; -NCHC$_2$-heteroaryl; benzyl; -OCH$_2$-heteroaryl; -C(O)H; -C(O)(C$_1$-C$_8$)alkyl; -CN; -NO$_2$; -S(O)(C$_1$-C$_8$)alkyl; S(O)$_2$(C$_1$-C$_8$)alkyl; S(O)$_2$N((C$_1$-C$_8$)alkyl)$_2$; -S(O)$_2$NH(C$_1$-C$_8$)alkyl; -S(O)$_2$NH(C$_2$-C$_8$)cycloalkyl; -S(O)$_2$NH$_2$; -NHS(O)$_2$(C$_1$-C$_8$)alkyl; N((C$_1$-C$_8$)alkyl)S(O)$_2$(C$_1$-C$_8$)alkyl; -(C$_1$-C$_8$)alkyl-O-(C$_1$-C$_8$)alkyl; -O-(C$_1$-C$_8$)alkyl-O-(C$_1$-C$_8$)alkyl; -C(O)OH; -C(O)O(C$_1$-C$_8$)alkyl; NHOH; NHO (C$_1$-C$_8$)alkyl; -O-halogenated (C$_1$-C$_8$)alkyl; -S(O)$_2$- halogenated (C$_1$-C$_8$)alkyl; -S-halogenated (C$_1$-C$_8$)alkyl; -NHC(O)O-(C$_1$-C$_6$)alkyl; -N((C$_1$-C$_6$)alkyl)C(O)O-(C$_1$-C$_6$)alkyl; -C(=NH)-(C$_1$-C$_6$)alkyl; -C(=NOH)-(C$_1$-C$_6$)alkyl; and -C(=N-O-(C$_1$-C$_6$)alkyl)-(C$_1$-C$_6$)alkyl.

25. A pharmaceutical composition comprising a compound according to claim 20, or a pharmaceutically acceptable salt thereof; and one or more pharmaceutically acceptable excipients.

26. A pharmaceutical composition comprising a compound according to claim 22, or a pharmaceutically acceptable salt thereof; and one or more pharmaceutically acceptable excipients.

* * * * *